US011266739B2

(12) United States Patent
Gilbert

(10) Patent No.: US 11,266,739 B2
(45) Date of Patent: Mar. 8, 2022

(54) METHODS AND COMPOSITIONS FOR ADOPTIVE CELL THERAPY

(71) Applicant: Juno Therapeutics, Inc., Seattle, WA (US)

(72) Inventor: Mark J. Gilbert, Seattle, WA (US)

(73) Assignee: Juno Therapeutics, Inc., Seattle, WA (US)

(*) Notice: Subject to any disclaimer, the term of this patent is extended or adjusted under 35 U.S.C. 154(b) by 335 days.

(21) Appl. No.: 14/958,919

(22) Filed: Dec. 3, 2015

(65) Prior Publication Data

US 2016/0158359 A1 Jun. 9, 2016

Related U.S. Application Data

(60) Provisional application No. 62/087,224, filed on Dec. 3, 2014.

(51) Int. Cl.
| | | |
|---|---|---|
| A61K 39/395 | (2006.01) | |
| C07K 14/725 | (2006.01) | |
| C07K 14/705 | (2006.01) | |
| C07K 16/28 | (2006.01) | |
| C07K 14/71 | (2006.01) | |

(52) U.S. Cl.
CPC .... *A61K 39/39558* (2013.01); *C07K 14/7051* (2013.01); *C07K 14/70521* (2013.01); *C07K 14/70578* (2013.01); *C07K 14/71* (2013.01); *C07K 16/2803* (2013.01); *C07K 2317/622* (2013.01); *C07K 2319/00* (2013.01); *C07K 2319/03* (2013.01); *C07K 2319/33* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen et al. |
| 5,087,616 | A | 2/1992 | Myers et al. |
| 5,200,084 | A | 4/1993 | Liberti et al. |
| 5,219,740 | A | 6/1993 | Miller et al. |
| 6,040,177 | A | 3/2000 | Riddell et al. |
| 6,207,453 | B1 | 3/2001 | Maass et al. |
| 6,410,319 | B1 | 6/2002 | Raubitschek et al. |
| 6,451,995 | B1 | 9/2002 | Cheung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 8,324,353 | B2 | 12/2012 | Jensen |
| 8,389,282 | B2 | 3/2013 | Sadelain et al. |
| 8,399,645 | B2 | 3/2013 | Campana et al. |
| 8,497,118 | B2 | 7/2013 | Jensen |
| 8,822,647 | B2 | 9/2014 | Jensen |
| 8,911,993 | B2 | 12/2014 | June et al. |
| 2002/0131960 | A1 | 9/2002 | Sadelain et al. |
| 2003/0170238 | A1 | 9/2003 | Gruenberg et al. |
| 2011/0003380 | A1 | 1/2011 | Mlltenyl et al. |
| 2012/0128586 | A1* | 5/2012 | Calissano ........ G01N 33/57426 424/1.65 |
| 2013/0149337 | A1 | 6/2013 | Cooper et al. |
| 2013/0287748 | A1* | 10/2013 | June ...................... A61K 35/17 424/93.21 |
| 2014/0271635 | A1 | 9/2014 | Brogdon et al. |
| 2014/0314795 | A1 | 10/2014 | Riddell |
| 2015/0139943 | A1 | 5/2015 | Campana et al. |
| 2015/0306141 | A1 | 10/2015 | Jensen |
| 2015/0376296 | A1 | 12/2015 | Fedorov |
| 2016/0206656 | A1 | 7/2016 | Gilbert |
| 2018/0355014 | A1 | 12/2018 | Thompson et al. |
| 2020/0297760 | A1 | 9/2020 | Bonyhadi et al. |

FOREIGN PATENT DOCUMENTS

| | | |
|---|---|---|
| CN | 103 483 453 | 1/2014 |
| CN | 104 583 230 | 4/2015 |
| CN | 104 910 279 | 9/2015 |
| CN | 106 163 547 | 11/2016 |
| EP | 0 452 342 | 10/1991 |
| EP | 2 537 416 | 12/2012 |
| JP | 2014-507118 | 3/2014 |
| JP | 2017-530694 | 10/2017 |
| WO | WO-1992/008796 | 5/1992 |
| WO | WO-1994/028143 | 12/1994 |

(Continued)

OTHER PUBLICATIONS

US 8,252,592 B2, 08/2012, Sadelain (withdrawn)
Long et al (OI, 2(4):e23641:1-2, 2013).*
Davila et al (a) (OI, 1(9): 1577-1583, 2012).*
Davila et al (b) (PLOS ONE, 8(4):e61388:1-14, 2013).*
Gill et al (EOBT, 14(1):37-49, 2014, published online Nov. 2013).*

(Continued)

*Primary Examiner* — Brad Duffy
(74) *Attorney, Agent, or Firm* — Morrison Foerster LLP

(57) ABSTRACT

Provided are methods for multiple administrations of cells for adoptive cell therapy, and for administering cells to subjects having received prior administrations, and compositions and articles of manufacture for use in the methods. The cells generally express recombinant molecules such as recombinant receptors, e.g., chimeric antigen receptors (CARs) and/or other transgenic receptors. The methods can involve administering cells expressing a first or prior receptor(s) and cells expressing a second or subsequent receptor(s), the second or subsequent receptor(s) being distinct from the first, and which generally do not express the first receptor, and/or administering the cells expressing the second receptor to a subject having received the first administration. The methods can provide various advantages, such as improved efficacy in the context an immune response in the subject against the first or prior receptor and/or in the context of antigen loss, downregulation, or modification, following a first or prior administration.

45 Claims, 6 Drawing Sheets

Specification includes a Sequence Listing.

(56) References Cited

FOREIGN PATENT DOCUMENTS

| | | |
|---|---|---|
| WO | WO-2000/014257 | 3/2000 |
| WO | WO 2003/027135 | 4/2003 |
| WO | WO-2009/072003 | 6/2009 |
| WO | WO 2009/124109 | 10/2009 |
| WO | WO-2010/033140 | 3/2010 |
| WO | WO 2010/095031 | 8/2010 |
| WO | WO 2012/079000 | 6/2012 |
| WO | WO-2012/129514 | 9/2012 |
| WO | WO 2013/059593 | 4/2013 |
| WO | WO-2013/071154 | 5/2013 |
| WO | WO-2013/123061 | 8/2013 |
| WO | WO-2013/126726 | 8/2013 |
| WO | WO-2013/166321 | 11/2013 |
| WO | WO 2014/011988 | 1/2014 |
| WO | WO-2014/031687 | 2/2014 |
| WO | WO-2014/055668 | 4/2014 |
| WO | WO 2014/065961 | 5/2014 |
| WO | WO 2014/153270 | 9/2014 |
| WO | WO-2015/157391 | 10/2015 |
| WO | WO 2015/142675 | 11/2015 |
| WO | WO 2016/028896 | 2/2016 |
| WO | WO-2017/096327 | 6/2017 |
| WO | WO-2017/096329 | 6/2017 |

OTHER PUBLICATIONS

Cheadle et al (JI, 184:1885-1896, 2010).*
Fred Hutchinson Cancer Research Center, "Laboratory Treated T Cells in Treating Patients With Relapsed or Refractory Chronic Lymphocytic Leukemia, Non-Hodgkin Lymphoma, or Acute Lymphoblastic Leukemia," ClinicalTrials.gov Identifier: NCT01865617, Retrieved from the Internet: URL:http://clinicaltrials.gov/show/NCT01865617 [retrieved on Aug. 26, 2014].
Han et al., "Chimeric antigen receptor-engineered T cells for cancer immunotherapy: progress and challenges," Journal of Hematology & Oncology (2013) 6:47.
Memorial Sloan-Kettering Cancer Center, "Precursor B Cell Acute Lymphoblastic Leukemia (B-ALL) Treated With Autologous T Cells Genetically Targeted to the B Cell Specific Antigen CD19," ClinicalTrials.gov Identifier: NCT01044069, Retrieved from the Internet: URL:http://clinicaltrials.gov/ct2/show/NCT01044069 [retrieved on Aug. 26, 2014].
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.
Berger et al., "Analysis of transgene-specific immune responses that limit the in vivo persistence of adoptively transferred HSV-TK-modified donor T cells after allogeneic hematopoietic cell transplantation," Blood. Mar. 15, 2006;107(6):2294-302.
Berger et al., "Cutaneous T-cell lymphoma: malignant proliferation of T-regulatory cells," Blood. Feb. 15, 2005;105(4):1640-7.
Berger et al., "Nonmyeloablative immunosuppressive regimen prolongs In vivo persistence of gene-modified autologous T cells in a nonhuman primate model," J Virol. Jan. 2001;75(2):799-808.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7:2031-2034.
Brentjens et al., "CD19-targeted T cells rapidly induce molecular remissions in adults with chemotherapy-refractory acute lymphoblastic leukemia," Sci Transl Med. (2013) 5(177).
Brentjens et al., "Safety and persistence of adoptively transferred autologous CD19-targeted T cells in patients with relapsed or chemotherapy refractory B-cell leukemias," Blood (2011) 118(18):4817-4828.

Brusic et al., "Prediction of MHC class II-binding peptides using an evolutionary algorithm and artificial neural network," Bioinformatics. (1998) 14:121-131.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10):1137-46.
Cavalieri et al., "Human T lymphocytes transduced by lentiviral vectors in the absence of TCR activation maintain an intact immune competence," Blood (2003) 102(2):497-505.
Chicaybam et al., "An efficient lowcost method for gene transfer to T lymphocytes," PLoS ONE (2013) 8(3):e60298.
Cho et al., "Human mammalian cell sorting using a highly integrated micro-fabricated fluorescence-activated cell sorter (microFACS)," Lab Chip (2010) 10:1567-1573.
Clarke and Davies in: Methods in Molecular Medicine, vol. 58: Metastasis Research Protocols, vol. 2: Cell Behavior In Vitro and In Vivo, Edited by: S. A. Brooks and U. Schumacher ©Humana Press Inc., Totowa, NJ (2001) pp. 17-25.
Cooper et al., "T-cell clones can be rendered specific for CD19: toward the selective augmentation of the graft-versus-B-lineage leukemia effect," Blood. (2003) 101:1637-1644.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
Davila et al., "Efficacy and toxicity management of 19-28z CAR T cell therapy in B cell acute lymphoblastic leukemia," Sci Transl Med (2014) 6:224ra25.
Davila et al., "How do CARs work?: Early insights from recent clinical studies targeting CD19," Oncoimmunoloqy (2012) 1(9):1577-1583.
De Jesus et al., "The role of tryptophan side chains in membrane protein anchoring and hydrophobic mismatch," Biochim Biophys Acta. Feb. 2013;1828(2):864-76.
Ettinger et al., "A peptide binding motif for HLA-DQA1*0102/DQB1*0602, the class II MHC molecule associated with dominant protection in insulin-dependent diabetes mellitus," J Immunol. Mar. 1, 1998;160(5):2365-73.
Fedorov et al., "PD-1—and CTLA-4-based inhibitory chimeric antigen receptors (iCARs) divert off-target immunotherapy responses," Sci. Transl. Medicine (2013) 5(215).
Fry et al., "Clinical Activity and Persistence of Anti-CD22 Chimeric Antigen Receptor in Children and Young Adults with Relapsed/Refractory Acute Lymphoblastic Leukemia (ALL)," ASH, Dec. 2015; Retrieved from the Internet: https://ash.confex.com/ash/2015/webprogram/Paper86307.html [retrieved Nov. 23, 2015].
Fry et al., "T-cell adoptive immunotherapy for acute lymphoblastic leukemia," Hematology Am Soc Hematol Educ Program. (2013);2013:348-53.
Godin et al., "Microfluidics and photonics for Bio-System-on-a-Chip: a review of advancements in technology towards a microfluidic flow cytometry chip," J Biophoton. (2008) 1(5):355-376.
Grupp et al., "Chimeric antigen receptor-modified T cells for acute lymphoid leukemia," N. Engl. J. Med. (2013) 368:1509-1518.
Hermans et al., "The VITAL assay: a versatile fluorometric technique for assessing CTL—and NKT-mediated cytotoxicity against multiple targets in vitro and in vivo," J. Immunological Methods (2004) 285(1):25-40.
Honeyman et al., "Neural network-based prediction of candidate T-cell epitopes," Nat Biotechnol. Oct. 1998;16(10):966-9.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin. Cancer Res. (2013) 19:3153.
International Search Report and Written Opinion for PCT/US2015/063839, dated Feb. 24, 2016, 14 pages.

(56) References Cited

OTHER PUBLICATIONS

Jensen et al., "Antitransgene rejection responses contribute to attenuated persistence of adoptively transferred CD20/CD19-specific chimeric antigen receptor redirected T cells in humans," Biol Blood Marrow Transplant. Sep. 2010; 16(9):1245-1256.
Johnston, et al., "Biolistic transformation: microbes to mice," Nature (1990) 346:776-777.
"Juno's Investigational CAR T Cell Product Candidates JCAR014 and JCAR018 Demonstrate Encouraging Clinical Responses in Patients with B-Cell Cancers" http://www.businesswire.com/news/home/20151206005065/en/Juno%E2%80%99s-Investigational-CAR-Cell-Product-Candidates-JCAR014.
Karosiene et al., "NetMHCIIpan—3.0, a common pan-specific MHC class II prediction method including all three human MHC class II isotypes, HLA-DR, HLA-DP and HLA-DQ," Immunogenetics. Oct. 2013;65(10):711-24.
Kim et al., "Immune epitope database analysis resource," Nucleic Acids Res. Jul. 2012;40(Web Server issue):W525-30.
Klebanoff et al., "Sorting through subsets: which T-cell populations mediate highly effective adoptive immunotherapy?," J Immunother. (2012) 35(9):651-660.
Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.
Kochenderfer et al., "Construction and preclinical evaluation of an anti-CD19 chimeric antigen receptor," J. Immunotherapy (2009) 32(7):689-702.
Kochenderfer et al., "Treating B-cell cancer with T cells expressing anti-CD19 chimeric antigen receptors," Nature Reviews Clinical Oncology (2013) 10, 267-276.
Koste et al., "T-cell receptor transfer into human T cells with ecotropic retroviral vectors," Gene Therapy (2014) 21:533-538.
Kutler et al., "An algorithm for the prediction of proteasomal cleavages," J Mol Biol. May 5, 2000;298(3):417-29.
Lafuente et al., "Prediction of MHC-peptide binding: a systematic and comprehensive overview," Curr Pharm Des. (2009);15(28):3209-20.
Lamers et al., "Immune responses to transgene and retroviral vector in patients treated with ex vivo-engineered T cells," Blood (2011) 117:72-82.
Lundegaard et al., "NetMHC—3.0: accurate web accessible predictions of human, mouse and monkey MHC class I affinities for peptides of length 8-11," Nucl. Acids Res. (2008);36(suppl 2):W509-W512.
Lupton S. D. et al., "Dominant positive and negative selection using a hygromycin phosphotransferase-thymidine kinase fusion gene," Mol. and Cell Biol. (1991) 11:6.
Manuri et al., "piggyBac transposon/transposase system to generate CD19-specific T cells for the treatment of B-lineage malignancies," Hum Gene Ther (2010) 21(4):427-437.
Miller et al., "Improved retroviral vectors for gene transfer and expression," BioTechniques (1989) 7:980-990.
Miller et al., "Retrovirus packaging cells," Human Gene Therapy (1990) 1:5-14.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Nielsen et al., "Quantitative predictions of peptide binding to any HLA-DR molecule of known sequence: NetMHCIIpan," PLoS Comput Biol. Jul. 4, 2008;4(7):e1000107.
Nielsen et al., "Reliable prediction of T-cell epitopes using neural networks with novel sequence representations," Protein Sci. (2003);12:1007-1017.
Nussbaum et al., "PAProC: a prediction algorithm for proteasomal cleavages available on the WWW," Immunogenetics. Mar. 2001;53(2):87-94.
Park et al., "Adoptive transfer of chimeric antigen receptor re-directed cytolytic T lymphocyte clones in patients with neuroblastoma," Molecular Therapy (2007) 15(4):825-833.
Park et al., "Treating cancer with genetically engineered T cells," Trends Biotechnol. (2011) 29(11):550-557.
Parker et al., "Scheme for ranking potential HLA-A2 binding peptides based on independent binding of individual peptide side-chains," J Immunol. Jan. 1, 1994;152(1):163-75.
Pegram et al., "CD28z CARs and armored CARs," Cancer J. Mar.-Apr. 2014;20(2):127-33.
Peters et al., "Generating quantitative models describing the sequence specificity of biological processes with the stabilized matrix method," BMC Bioinformatics. May 31, 2005;6:132.
Peters et al., "The immune epitope database and analysis resource: From vision to blueprint.," PLoS Biol (2005);3(3):379-381.
Rammensee et al., "SYFPEITHI: database for MHC ligands and peptide motifs," Immunogenetics. Nov. 1999;50(3-4):213-9.
Remington: The Science and Practice of Pharmacy, 21st Edition, Journal of Pharmacy Technology, Mar.-Apr. 2006;22:133-134.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Riddell et al., "T-cell mediated rejection of gene-modified HIV-specific cytotoxic T lymphocytes in HIV-infected patients," Nature Medicine (1996) 2, 216-223.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4):388-398.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloney-based vectors in ecotropic and amphotropic packaging cell lines," Virology (1991) 180:849-852.
Sette et al., "Peptide binding to the most frequent HLA-A class I alleles measured by quantitative molecular binding assays," Mol Immunol. Aug. 1994;31(11):813-22.
Sharma et al., "Efficient sleeping beauty DNA transposition from DNA minicircles," Molec Ther Nucl Acids (2013) 2, e74.
Sidney et al., "Quantitative peptide binding motifs for 19 human and mouse MHC class I molecules derived using positional scanning combinatorial peptide libraries," Immunome Res. Jan. 25, 2008;4:2.
Solberg et al., "Balancing selection and heterogeneity across the classical human leukocyte antigen loci: a meta-analytic review of 497 population studies," Hum Immunol. Jul. 2008;69(7):443-64.
Southwood et al., "Several common HLA-DR types share largely overlapping peptide binding repertoires," J Immunol. Apr. 1, 1998;160(7):3363-73.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10):928-933.
Tsukahara et al., "CD19 target-engineered T-cells accumulate at tumor lesions in human B-cell lymphoma xenograft mouse models," Biochem Biophys Res Commun (2013) 438(1):84-9.
Turtle et al., "Engineered T cells for anti-cancer therapy," Curr. Opin. Immunol. (2012) 24(5):633-39.
Van Tendeloo et al., "High-level transgene expression in primary human T lymphocytes and adult bone marrow CD34+ cells via electroporation-mediated gene delivery," Gene Therapy (2000) 7(16):1431-1437.
Verhoeyen et al., "Lentiviral vector gene transfer into human T cells," Methods Mol Biol. (2009) 506:97-114.
Wadhwa et al., "Receptor mediated glycotargeting," J. Drug Targeting (1995) 3:111.

(56) References Cited

OTHER PUBLICATIONS

Wang et al., "Phenotypic and functional attributes of lentivirus-modified CD19-specific human CD8+ central memory T cells manufactured at clinical scale," J Immunother. (2012) 35(9):689-701.

Wu et al., "Adoptive T-cell therapy using autologous tumor-infiltrating lymphocytes for metastatic melanoma: current status and future outlook," Cancer (2012) 18(2):160-75.

Xu et al., "Cytokine release syndrome in cancer immunotherapy with chimeric antigen receptor engineered T cells," Cancer Letters (2014) 343:172-78.

Zhang et al., "TEPITOPEpan: extending TEPITOPE for peptide binding prediction covering over 700 HLA-DR molecules," PLoS One. (2012);7(2):e30483. doi: 10.1371/journal.pone.0030483.

Geiger et al., "Human naive and memory CD4+ T cell repertoires specific for naturally processed antigens analyzed using libraries of amplified T cells," J Exp Med (2009) 206(7):1525-1534.

Haso et al., "Anti-CD22-chimeric antigen receptors targeting B-cell precursor acute Tymphoblastic leukemia," Blood. (2013) 121(7):1165-1174.

Jena et al., "Chimeric antigen receptor (CAR)-specific monoclonal antibody to detect CD19-specific T cells in clinical trials," PLoS One. (2013);8(3):e57838.

Makkouk et al., "Cancer Immunotherapy and Breaking Immune Tolerance: New Approaches to an Old Challenge," Cancer Res (2015) 75(1):5-1.

Shaffer et al., "Foreign or Domestic CARs: Receptor Ligands as Antigen-Binding Domains," Med. Sci. (2014), 2(1), 23-36.

Wu et al., "Remote control of therapeutic T cells through a small molecule-gated chimeric receptor," Science (2015) 350(6258):aab4077.

Lee et al., "T cells expressing CD19 chimeric antigen receptors for acute lymphoblastic leukaemia in children and young adults: a phase 1 dose-escalation trial," Lancet (2015) 385(9967): 517-528.

Lucienne, "CD3-specific antibodies as promising tools to aim at immune tolerance in the clinic," Int Rev Immunol. May-Aug. 2006; 25(3-4): 215-33.

Maude et al., "Chimeric antigen receptor T cells for sustained remissions in leukemia," N Engl J Med. (2014) 371(16): 1507-1517.

NCI Clinical Trial Identifier NCT02315612, dated Nov. 11, 2015. Retrieved from https://clinicaltrials.gov/ct2/history/NCT02315612?V_9=View#StudyPageTop.

"United States Securities and Exchange Commission, Annual Report Pursuant to Section 13 or 15(d) of the Securities Exchange Act of 1934,""signed Mar. 18, 2015".

Chmielewski et al., "Antigen-Specific T-Cell Activation Independently of the MHC: Chimeric Antigen Receptor-Redirected T Cells," Front Immunol. Nov. 11, 2013;4:371.

Gertel et al., "Immune tolerance induction with multipitope peptide derived from citrullinated autoantigens attenuates arthrirtis manifestations in adjuvant arthrtis rats," J Immunol (2015) 194(12):5674-5680.

* cited by examiner

☐ High affinity: 0 nM to 50 nM
▨ Low affinity: 51 nM to 1000 nM
▦ Rare affinity: 1000 nM to 5000 nM

Fig. 6

```
              CD28 transmembrane domain  ←·· — ·· — ·· — ·· — ·· — ·· — ·· — ·· Junction Region
              ←─────────────────────────────────
              FWVLVVVGGV  LACYSLLVTV  AFIIFWVKRG        30

─·· — ·· — ·· →            4-1BB costimulatory domain
              ─ ─ ─ ─ ─ ─ ─ ─ ─ ─ ─ ─ ─ ─ ─ ─ ─ ─ ─ ─ ─ ─ ─ ─ ─ ─ ─ ─ ─
              RKKLLYIFKQ  PFMRPVQTTQ  EEDGCSCRFP        60

─ ─ ─ ─ ─ ─ →
              EEEEGGCEL                                 69
```

SEQ ID NO: 5

METHODS AND COMPOSITIONS FOR ADOPTIVE CELL THERAPY

CROSS-REFERENCE TO RELATED APPLICATIONS

This application claims priority from U.S. provisional application No. 62/087,224 filed Dec. 3, 2014, entitled "Methods and Compositions for Adoptive Cell Therapy," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042001200SeqList.txt, created Dec. 3, 2015, which is 65,266 bytes in size. The information in electronic format of the Sequence Listing is incorporated by reference in its entirety.

FIELD

The present disclosure relates to adoptive cell therapy involving the administration of multiple doses of cells expressing genetically engineered (recombinant) receptors, e.g., via multiple administration steps and/or by administration to subjects having received a prior administration. In general, cells administered in connection with certain different administration steps express distinct receptors. The recombinant receptors may include chimeric receptors, e.g., chimeric antigen receptors (CARs), and/or other transgenic receptors such as transgenic T cell receptors (TCRs). Features of the methods provide various advantages, such as improved efficacy, for example, due to increased exposure of the treated subject to administered cells expressing receptors that target disease-associated antigens. A subsequent administration of cells expressing a receptor distinct from that expressed by cells in a first or prior administration can improve efficacy. For example, it can minimize the risk of reduced exposure to the cells, which can result from specific anti-receptor immune response in the subject, and/or allow for effective targeting in cases of antigen loss and/or downregulation or modification of the antigen or epitope targeted by the first or prior receptor.

BACKGROUND

Various methods are available for adoptive cell therapy using engineered cells expressing recombinant receptors, such as chimeric antigen receptor (CARs). Improved methods are needed, for example, to improve efficacy of such therapies, for example, by increasing exposure of the subject to the administered cells. Such methods are needed, for example, that improve expansion and/or persistence of the administered cells, provide the ability to treat refractory or relapsed subjects, and/or that reduce the risk of toxicity or other unwanted outcomes. Provided are methods, compositions, and articles of manufacture that meet such needs.

SUMMARY

Provided are methods for administering cells to subjects, such as for adoptive cell therapy, for example, in treating cancer and other diseases, conditions, or disorders, as well as cells, compositions, and articles of manufacture for use in such methods. The cells generally express one or more recombinant receptors, such as chimeric antigen receptor (CARs), other antigen receptors, and/or other chimeric receptors. In some embodiments, the methods increase exposure of the subject to the administered cells, such as by improving expansion and/or persistence of the administered cells, provide the ability to treat refractory or relapsed subjects and/or subjects displaying loss, downregulation, or modification of a targeted antigen or epitope thereof. In some embodiments, the methods reduce the risk of toxicity or other unwanted outcomes compared with other methods of cell therapy.

In some embodiments, provided are methods of treatment, carried out by administering cells to a subject, where the cells express a second (or subsequent) receptor, such as a second (or subsequent) chimeric antigen receptor (CAR) or transgenic TCR, where the subject has previously received an administration or dose of cells expressing a first (or prior) receptor, such as a first (or prior) CAR or TCR. The second or subsequent receptor is generally distinct from the first or prior receptor. In some embodiments, the methods further include administering the cells expressing the first or prior receptor prior to the administration of the cells expressing the second or subsequent receptor. For example, in some embodiments, the methods are carried out by (a) administering to the subject the cells expressing the first or prior receptor (e.g., first or prior CAR), and (b) administering to the subject cells expressing a first or prior receptor, e.g., CAR; and (b) administering to the subject cells expressing a second or subsequent receptor, e.g., CAR.

In some embodiments, the cells expressing the second or subsequent receptor, e.g., CAR, do not express the first or prior receptor, e.g., CAR. In some embodiments, the first (or prior) and/or second (or subsequent) receptor is an antigen receptor, such as a CAR or a transgenic TCR. In some such embodiments, the first or prior receptor, e.g., CAR, specifically binds to an antigen associated with a disease or condition or disorder in the subject. In some embodiments, the second or subsequent receptor, e.g., CAR, specifically binds to the antigen specifically bound by the first or prior receptor. In some embodiments, the first or prior receptor, e.g., CAR, and the second or subsequent receptor, e.g., CAR, specifically bind to the same epitope of the antigen. In some embodiments, the first or prior receptor competes for binding to the antigen with the second or subsequent receptor, or vice versa. In some embodiments, the first or prior receptor and the second or subsequent receptor specifically bind to distinct epitopes or portions of the antigen.

In some embodiments, the second or subsequent receptor specifically binds to a different antigen associated with the disease or condition or disorder in the subject. For example, in some embodiments, the antigen recognized or bound by the first receptor is CD19 and the antigen specifically bound or recognized by the second or subsequent receptor is a B-cell specific or B-cell associated antigen (or antigen associated with or specific for B cell disease(s), e.g., B cell malignancy), that is distinct from CD19, such as CD22 or CD20.

In some embodiments, the second or subsequent receptor, e.g., CAR, does not specifically bind to the antigen specifically bound by the first or prior receptor, e.g., CAR. In some embodiments, the cells expressing the second or subsequent receptor do not include a receptor that specifically binds to the antigen specifically bound by the first or prior receptor.

In some embodiments, at the time of, prior to, and/or immediately prior to, the administration of cells expressing the second or subsequent receptor, the subject exhibits a detectable humoral and/or cell-mediated immune response specific for the first or prior receptor. In some embodiments, the subject does not exhibit a detectable humoral or cell-mediated immune response against the second or subsequent receptor, e.g., CAR within about 30 days, within about 60 days, or within about 90 days, of the administration of the cells expressing the second or subsequent receptor, such as the administration in (b).

In some embodiments, at the time of, prior to, and/or immediately prior to, the administration of cells expressing the second or subsequent receptor, the disease or condition persists in the subject; and/or the disease or condition has relapsed in the subject.

In some embodiments, at the time of, prior to, and/or immediately prior to, the administration of cells expressing the second or subsequent receptor, the subject exhibits downregulation, loss, or modification of the antigen specifically bound by the first or prior receptor.

In some embodiments, the time between the administration of the cells expressing the first or prior receptor and the administration of the cells expressing the second or subsequent receptor is at least about 28 days; at least about 35 days; at least about 42 days; at least about 49 days; or at least about 60 days. In some embodiments, the time is at least about 14, 15, 16, 17, 18, 19, 20, 21, 22, 23, 24, 25, 26, or 27 days, such as at least 14 days or at least 21 days.

In some embodiments, the first or prior receptor, e.g., CAR, includes at least one immunoreactive epitope that is not present in the second or subsequent receptor, e.g., CAR. In some embodiments, the at least one immunoreactive epitope includes at least one B cell epitope or epitope recognized by the humoral immune system; and/or includes at least one T cell epitope or epitope recognized by a cell-mediated response such as one recognized by a cytotoxic and/or helper T cell.

In some embodiments, the subject has not received a dose of cells expressing the first or prior receptor prior to the administration in (a); and/or has not received a dose of cells expressing the second or subsequent receptor prior to the administration in (b) or prior to the initiation of the method.

In some embodiments, the disease or condition is a tumor. In some embodiments, it is or is associated with an infectious disease. In some embodiments, it is or is associated with an autoimmune disease or disorder.

The second or subsequent receptor, e.g., second or subsequent CAR, generally includes one or more differences in amino acid sequence compared to the first or prior receptor, e.g., the first or prior CAR. In some embodiments, the one or more differences includes at least one amino acid sequence difference compared to a region of the first or prior receptor, e.g., CAR, to which a detectable immune response is generated in the subject following the administration in (a) or the prior administration of cells expressing the first or prior receptor, e.g., CAR. In some embodiments, such one or more differences include at least one amino acid sequence difference compared to each region of the first or prior receptor to which a detectable immune response is generated in the subject following the administration in (a) or the prior administration. In some embodiments, such an immune response is detected in connection with the methods.

In some embodiments, the methods further include, prior to the administration of the cells expressing the second or subsequent receptor or prior to the administration in (b), detecting the presence of a receptor-specific, e.g., CAR-specific, immune response in the subject. In some embodiments, the detection comprises identifying at least a region of the first or prior receptor, e.g., CAR, to which the subject exhibits a specific immune response, such as a specific antibody- or cell-mediated immune response.

In some embodiments, the second or subsequent receptor, e.g., CAR contains one or more amino acid sequence differences compared to the region of the first or prior receptor, e.g., CAR, for which an immune response in the subject, such as a detectable immune response in the subject, is specific. In some such embodiments, such region of the first or prior receptor is or includes a junction between two endogenous sequences or domains. In some embodiments, it is or includes a region within one or more CAR portions selected from the group consisting of an scFv portion, a linker portion, an amino acid sequence not endogenous to the subject, a sequence derived from a difference species than that of the subject, and/or junction between two CAR domains. In some embodiments, it is or includes a framework region (FR) within the scFv portion, a heavy chain FR sequence, a heavy chain CDR sequence, a light chain FR sequence, and/or a light chain CDR sequence.

In some embodiments, the subsequent or second receptor, e.g., CAR, includes at least one region that is identical in amino acid sequence to a corresponding region of the first or prior receptor, e.g., CAR. In some embodiments, such corresponding region of the first or prior receptor, e.g., CAR, is a region to which the subject does not exhibit a detectable humoral or cell-mediated immune response, e.g., prior to or at the time of the administration of cells expressing the second receptor. In some embodiments, it is or includes an endogenous sequence. In some embodiments, it is or includes a region within a CAR portion selected from the group consisting of a costimulatory domain, an ITAM-containing domain, a transmembrane domain, a transduction or expression marker, a sequence endogenous to the host, and/or an antibody domain derived from the same species as the host.

In some embodiments, the methods result in an increase or enhancement of exposure of the subject to cells compared with other methods. In some embodiments, the maximum number of CAR-expressing cells, the area under the curve (AUC) for CAR-expressing cells over time, and/or the duration of detectable CAR-expressing cells in the subject following the administration of the cells expressing the second or subsequent receptor is greater as compared to that achieved via a method using an alternative dosing regimen involving administration of the cells expressing the first or prior receptor, e.g., the administration in (a), and a second or subsequent administration of cells expressing the first or prior receptor, which is carried out at the same point in time and/or otherwise under the same conditions as the administration in the provided method of the cells expressing the subsequent or second receptor, e.g., as the administration in (b).

In some embodiments, the method results in a maximum concentration or number of receptor-expressing, e.g., CAR-expressing, cells in the blood of the subject of at least at or about 10 receptor-expressing (e.g., CAR-expressing) cells per microliter, at least 50% of the total number of peripheral blood mononuclear cells (PBMCs), at least at least about $1\times10^5$ CAR-expressing cells, or at least 1,000, 2,000, 3,000, 4,000, or 5,000 copies of CAR-encoding DNA per micrograms DNA. In some embodiments, at day 30, at day 60, or at day 90 following the initiation of the administration of cells expressing the second or subsequent receptor, e.g., the administration in (b), receptor-expressing, e.g., CAR-expressing, cells are detectable in the blood or serum of the subject; and/or the blood of the subject contains at least 20% receptor-expressing (e.g., CAR-expressing) cells, at least 10 receptor-expressing (e.g., CAR-expressing) cells per microliter or at least 1×10⁴ receptor-expressing (e.g., CAR-expressing) cells.

In some embodiments, any of the above embodiments may involve multiple subsequent administrations. For example, in some embodiments, the methods are carried out in an iterative fashion, in which multiple administrations of cells, each expressing a further subsequent receptor (e.g., administrations of cells expressing third, fourth, fifth, sixth, and so-forth receptors, each distinct in some say from the first or prior receptor(s)).

BRIEF DESCRIPTION OF THE DRAWINGS

FIG. 6 depicts the amino acid sequence of an exemplary CD28-4-1BB sequence of SEQ ID NO: 5. Amino acids corresponding to the CD28 transmembrane domain are indicated by a solid line with arrows indicating the beginning and end positions; amino acids of the exemplary 4-1BB costimulatory domain are indicated by a dashed line with arrows indicating the beginning and end positions; amino acids of the exemplary junction region are indicated by a dashed and dotted line with arrows indicating the beginning and end positions and by italics. The two amino acids immediately flanking the junction site are indicated by a box. Exemplary amino acids that in some embodiments are targeted for modification, including K28, R31, and L34, are bolded and underlined. Regions of acidic residues that may be involved in 4-1BB-mediated TRAF-binding and signaling are indicated by a double underline.

DETAILED DESCRIPTION

Figure 1:
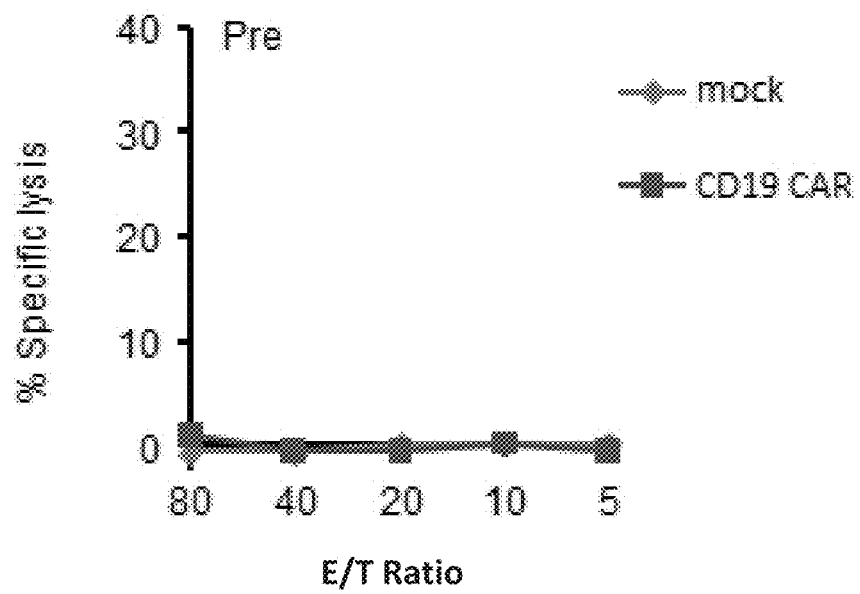
FIG. 1 shows results from an exemplary chromium release assay detecting the presence of a cytolytic immune response specific for CAR-expressing cells following administration of anti-CD19 CAR-expressing cells in a human subject. Results are shown for mixed-lymphocyte cultures containing peripheral blood mononuclear cells (PBMCs) derived from the subject pre-infusion (left panel) and post-infusion (right panel) with the CAR-expressing cells, in the presence of either CAR-expressing ("CD19-CAR") and non-CAR-expressing ("Mock"). "E/T"=effector to target cell ratio.
Figure 1:
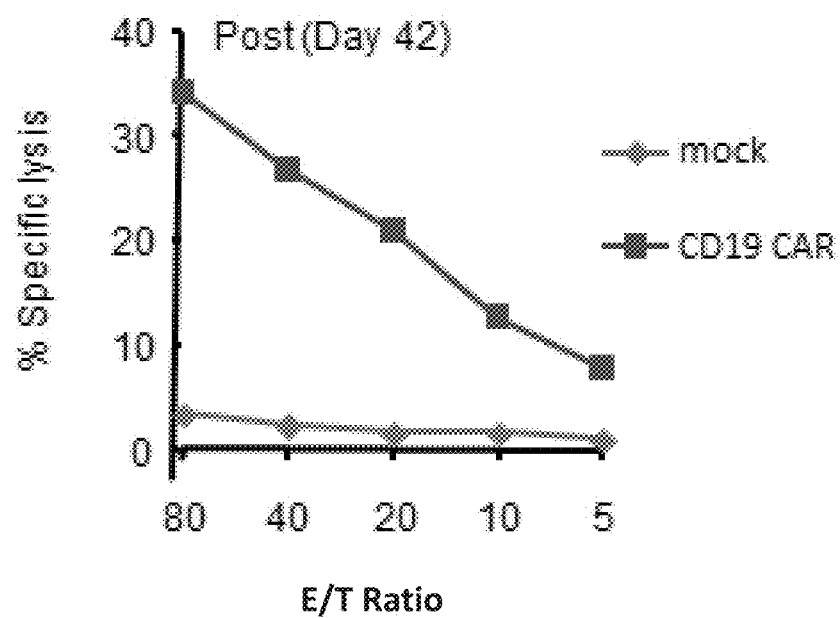

I. Methods of Treatment with Cells Expressing Recombinant Receptors

Provided are methods, compositions, and articles of manufacture for use in cell therapy, for example, for the treatment of various diseases and conditions such as tumors. The methods involve administering to a subject engineered cells expressing recombinant molecules, typically recombinant receptors designed to recognize and/or specifically bind to molecules associated with the disease or condition and/or to promote a particular therapeutic effect. Such binding can result in a response, such as an immune response targeting such molecules. The recombinant receptors may include chimeric receptors, e.g., chimeric antigen receptors (CARs), and/or other transgenic receptors, such as transgenic antigen receptors including transgenic T cell receptors (TCRs).

In particular, the methods involve multiple administrations of such cells or the administration of cells to a subject having received a prior administration or dose. Typically, the cells administered in a first or prior administration (e.g., in a first or prior dose) are distinct from those administered in the second or subsequent administration(s) or dose(s). Typically, the cells are distinct at least in part by way of their expression of distinct recombinant molecules, e.g., distinct recombinant receptors. In some embodiments, the cells of the second or subsequent administration or dose do not express the receptor expressed by those of the first dose or administration. In some embodiments, such cells express a receptor that is distinct from that of the first administration or dose. Thus, in some embodiments, the methods involve administering second (and/or third, fourth, fifth, and so forth) dose of cells to subjects having received a first dose, and/or administering to the subject the first and second (and/or third, fourth, fifth, and so forth) dose, in which the cells administered in the second dose express a receptor that is distinct from the receptor expressed by the cells administered in the first dose. The methods may be carried out in an iterative fashion.

In some aspects, the provided embodiments are based on observations herein that increased exposure of the subject to administered cells expressing the recombinant receptors (e.g., increased number of cells or duration over time) can improve efficacy and therapeutic outcomes in adoptive cell therapy. Preliminary analysis conducted following the administration of different CD19-targeting CAR-expressing T cells to subjects with various CD19-expressing cancers in multiple clinical trials revealed a correlation between greater and/or longer degree of exposure to the CAR-expressing cells and treatment outcomes.

Such outcomes included patient survival and remission, even in individuals with severe or significant tumor burden. Nonetheless, exposure may be limited by host immune responses against the recombinant receptors expressed by the administered cells, which may prematurely eliminate the cells. Once such a host immune response develops, either acquired or innate, it may not be feasible or effective to attempt to increase exposure or provide retreatment of subjects by administering a subsequent dose of cells expressing the same recombinant receptor. Once such an immune response has developed against the receptor, administration of such a second or subsequent dose of cells expressing the same receptor or one with similar immunogenic epitopes may result in rapid elimination of the cells before they have had a chance to expand and/or persist to an effective or substantial degree. Provided are embodiments that address these challenges.

In some embodiments, by providing a second (and/or other subsequent) dose of cells that expresses a second (and/or other subsequent) receptor (e.g., CAR) distinct from the first or prior receptor expressed by a first or prior dose, the provided methods address the problem of reduced exposure due to a host immune response against the first or prior receptor. In particular, because the cells of the second or subsequent dose do not express the same receptor expressed by the cells of the first or prior dose, the risk of the subject having mounted an immune response specific for a molecule present on the cells of the second or subsequent dose is reduced.

In some aspects, the provided embodiments are based on observations of antigen loss, mutation, modification, and/or downregulation in the context of immunotherapy, e.g., adoptive cellular immunotherapy. For example, CD19-negative disease has been observed in certain subjects having been administered CD19-targeted therapy, including anti-CD19 CAR-expressing T cells. In some embodiments, the provided methods offer advantages in such contexts of antigen downregulation or loss or modification. For example, administration of cells expressing a second or subsequent receptor which specifically binds to a different antigen as compared to the antigen or epitope targeted by a first or prior receptor—where the subject experiences or displays loss or modification of such epitope or antigen—can allow for continued treatment of the disease or condition and/or for improved efficacy. The different antigen in some embodiments is another antigen specific to or associated with the same disease or condition to or with which the first antigen is specific or associated. In some embodiments, it is a variant of the first antigen, such as a splice variant or mutated version expressed in the subject, e.g., during or subsequent to therapeutic intervention. Thus, also among the advantages of certain methods and compositions provided herein include the ability to provide continued, effective treatment in a subject experiencing antigen loss, downregulation, or modification which renders a first treatment approach less effective.

In some embodiments, the subject exhibits an immune response against the first or prior receptor following the first or prior administration, e.g., at the time of or immediately prior to the second or subsequent administration, such that further administration of cells expressing the first receptor or a method with similar immunogenicity, may not be efficacious. In some embodiments, the subject does not exhibit an immune response or a particular type or degree of immune response, against the second receptor following the administration of the cells expressing the second receptor, or does not exhibit such a response within a certain time period, such as within about 60 days of the administration of those cells. The type of immune response may be a detectable immune response, a humoral immune response, and/or a cell-mediated immune response. In some embodiments, the presence or absence of such an immune response after the first or prior administration is detected, and can inform which differences are designed to be present in the second or subsequent receptor as compared to the first or prior receptor. Such detection may include identifying at least a region of the first or otherwise prior receptor (e.g., CAR) to which the subject exhibits a specific immune response. Such an identified region may be varied in the second or otherwise subsequent receptor, e.g., a receptor selected in the second administration that differs in that one or more region.

In particular, the second molecule, e.g., second receptor (e.g., the second CAR), generally differs to some degree, e.g., in amino acid sequence and/or immunological epitope(s), from the first receptor (e.g. first CAR). Thus, the first or prior receptor generally includes at least one immunoreactive epitope that is not present in the second or subsequent receptor, such as at least one B cell epitope and/or at least one T cell epitope, which may be recognized by the immune system of the subject to which the cells are administered. In particular embodiments, the second (or subsequent) receptor, e.g., CAR, includes one or more differences in amino acid sequence compared to the first or prior receptor.

Such differences may include at least one difference compared to a region of the first or prior receptor to which a detectable immune response is exhibited in the subject following the first or prior administration, e.g., a difference in a region in the second or subsequent receptor that corresponds to such a region in the first or prior receptor. Regions including the difference(s) may include an antigen-binding portion, such as an scFv portion, including framework region(s) (FRs) within an scFv or variable region portion, such as FR1, FR2, FR3, e.g., of the VH, a heavy and/or light chain variable region portion, a linker portion, a hinge portion, a junction between two CAR domains, a transduction or expression marker, and/or a sequence of amino acids within the CAR that is non-endogenous, e.g., is not identical to a sequence present in an endogenous molecule of the host, such as a junctional region between two domains not naturally associated with one another in a single amino acid sequence in the natural setting, e.g., a junction between two endogenous sequences within a chimeric receptor or antibody/antibody fragment.

Although one or more differences is generally present in the second or other subsequent receptor as compared to the first or otherwise prior receptor, the receptors may also include regions of similarity, e.g., regions of amino acid sequence identity. In some embodiments, the region(s) of identity are ones to which the subject does not or is unlikely to exhibit an immune response following the first or prior administration. Such regions may include regions within a costimulatory domain, an ITAM-containing domain, a transmembrane domain, a CDR, and/or a transduction or expression marker. Where an scFv and/or variable region differs between the different receptors, it may be that the respective scFv or variable regions are derived from the same species (e.g., mouse or human), derived from different species, and/or combinations thereof.

In some embodiments, the noted differences are the only differences or substantially or essentially the only differences, between the recombinant molecule, e.g., receptor, in the cells of the first dose or administration as compared to the second dose or administration. In some embodiments, aside from differences in the receptor and/or other noted differences, the cells and/or cell populations administered in a prior and subsequent administration are identical or essentially or substantially identical. In some embodiments, the ratio of cells expressing detectable surface levels of one or more markers is the same or similar in one administration as compared to the subsequent administration. In some embodiments, the percentages of populations and/or subpopulations of cells in the different doses or administrations are the same or substantially or essentially the same. The different doses may contain the same percentage of T cells, CD8+ and/or CD4+ T cells, T cells of a particular lineage or activation state or experience, such as relative percentages of effector, naïve, and/or memory T cells, and/or sub-populations thereof such as $T_{CM}$, $T_{EM}$, $T_{SCM}$ cells and/or the cells may be derived from the same subject, sample, tissue, and/or fluid or compartment. In some embodiments, another portion of the same composition of cells used to engineer the cells of the first dose, e.g., by transduction with a vector encoding the recombinant receptor, is used to engineer the cells of the second administration. In some embodiments, the composition is preserved, e.g., by cryopreservation, prior to the second administration.

In some embodiments, the doses are administered in particular amounts and/or according to particular timing parameters. In some embodiments, the second or otherwise subsequent dose of cells expressing the second (or third, fourth, fifth, etc.) receptor is given at a time after an immune response has developed, had a chance to develop, and/or has been detected or otherwise confirmed to be present, against the receptor in the first or other prior dose, such as at or about or at least at or about 28 days or 35 days following the first or other prior dose.

The subsequent dose may be used for retreatment upon relapse, and/or to prevent recurrence of the targeted disease or disorder, and/or to address or prevent a reduction in exposure to cells expressing a recombinant receptor targeting the disease or condition or antigen of interest following a first or prior dose. For example, the subsequent dose in some embodiments is administered after or upon detection of a decline in persistence or expansion of such cells or in total or relative numbers of such cells in the subject or organ or fluid thereof. Thus, in some embodiments one or more of these parameters is measured, detected, or assessed in the time between the first or other prior dose and the second or other subsequent dose, and the timing or decision to administer the subsequent dose is made based on the outcome of such assessment. For example, the second dose may be administered at a time at which it is determined that the number or concentration of the receptor-expressing cells is below a desired level or has declined below a certain percentage of maximum or other measured concentration or number.

The recombinant receptors, e.g., CARs or transgenic TCRs, generally specifically bind to one or more antigen expressed by, associated with, and/or specific for a disease or condition in the subject and/or cell(s) or tissue(s) thereof. Such diseases may include tumors, cancers, other proliferative diseases, autoimmune diseases or disorders, and/or infectious agents or disease. In some embodiments, the first (or other prior) and the second (or other subsequent) receptors, although distinct, specifically bind to the same such antigen. The binding may be to a similar or the same epitope. In some embodiments, the binding of one receptor to antigen competes for binding to the antigen with the other. The binding in some embodiments is to an entirely different epitope, not competing with that of the other receptor, and/or to a completely different antigen. In this respect, the methods in some embodiments may be useful in treating subjects whose disease or condition has become resistant to treatments targeting a particular epitope or antigen, such as resulting from target downregulation or mutation by the disease or condition or cells thereof, and/or experiencing antigen loss. For example, in some embodiments, the antigen recognized or bound by the first receptor is CD19 and the antigen specifically bound or recognized by the second or subsequent receptor is a B-cell specific or B-cell associated antigen (or antigen associated with or specific for B cell disease(s), e.g., B cell malignancy), that is distinct from CD19, such as CD22 or CD20.

Thus, by offering the ability to target a similar but distinct disease-associated epitope or antigen, the methods in some embodiments improve efficacy not only by increasing overall persistence of engineered cells in the subject, but also by allowing the cells and/or form of therapy to function even in the context of downregulation or mutation of the original target. In some embodiments, the second receptor binds to the same antigen and a different antigen in the same disease, and/or the cell contains multiple receptors, each binding to a different antigen or epitope, one or more of which may be distinct from or the same as that recognized by the first receptor. In some embodiments, the second or subsequent receptor binds to a variant, e.g., a different splice variant or a modified version, of the antigen recognized by the first receptor.

In some embodiments, the different receptors have domain(s) (such as antigen-binding domains, e.g., sFvs, and/or or other domains of chimeric receptors, e.g., other CAR domains) having sequences with origins in the same species and/or those having sequences with origins in different species. For example, in some embodiments, the different receptors contain two distinct binding domains derived from the same species, such as two mouse-derived scFv domains or two scFv domains with framework region (FR) sequences derived from mouse, such as those derived from FMC63 and SJ25C1, respectively. In other embodiments, the different receptors contain two distinct binding domains for the same or different antigens derived from different species, such as a first receptor having an scFv or other binding domain derived from a murine sequence, such as FMC63 or SJ25C1 and another receptor with a domain derived in whole or in part from another species, such as a human or humanized sequence, such as one that binds to the same antigen, e.g., to a same or similar or distinct epitope, or to a distinct antigen.

In some embodiments, the receptor is a receptor other than an antigen receptor, such as one of a pair of binding partners and/or variant thereof, the other partner of which is specifically expressed in the context of a disease or condition or cells or tissues thereof, and/or expression of which is associated with the disease or condition. In some embodiments, such receptors are chimeric receptors. In some embodiments, such chimeric receptors contain extracellular binding portions that specifically interact with such a binding partner, and contain, for example, transmembrane and/or intracellular signaling domain(s) capable of potentiating an immunostimulatory signal or signals, such as an activating and/or costimulatory domains such as those present in certain chimeric antigen receptors.

In some embodiments, the provided methods are for long-term or continuous treatment or management of the disease or disorder in the subject, involving first, second, third, and/or multiple additional subsequent administrations of engineered cells, in which one or more of the doses includes cells expressing recombinant receptors distinct from those in other dose(s), but targeting the same disease or condition in the subject, such as distinct receptors targeting the same or different disease-specific or disease-associate antigen, at the same or different epitope(s). The long-term or chronic treatment or management in some embodiments is an iterative process, in which the subject is monitored for immunogenicity and/or drop in exposure, presence, persistence, numbers, and/or percentages of the cells, and a next subsequent administration (e.g., next subsequent receptor) is introduced if and when a particular indicator of loss of efficacy or risk thereof with respect to the first or prior receptor or cells is detected. In some embodiments, each subsequent administration is initiated upon detection of one or more indicators of a risk of loss of efficacy, such as reduced persistence of, expansion of, or exposure to the cells in the prior dose, an immune response specific thereto in the subject, relapse, resistance, and/or downregulation or change in the target antigen.

Exemplary Methods of Dosing with a Second Chimeric Receptor

In some embodiments, the methods include administration of a second chimeric receptor to a subject that has developed an immune response and/or is likely to be immunogenic to the first chimeric receptor. In some embodiments, the first chimeric receptor contains a junction region of a first and second domain that is immunogenic. In some embodiments, the immunogenic region includes one or more peptide epitopes (also called a T cell epitope). In some cases, a junction region that contains potential peptide epitopes spanning the junction of the two domains can be immunogenic and result in the generation of an immune response upon administration to a subject of a chimeric receptor containing the junction region. In some embodiments, the junction region can include a plurality of individual overlapping peptide fragments of contiguous sequence of about 8 to 24 amino (e.g. 8 to 15 amino acids or 8 to 13 amino acids, such as about or 8, 9, 10, 11, 12, 13, 14, 15 or more amino acids) directly C-terminal of the junction that joins a first domain and a second domain of the chimeric receptor and/or of about 8 to 24 amino acids (e.g. 8 to 15 amino acids or 8 to 13 amino acids, such as about or 8, 9, 10, 11, 12, 13, 14, 15 or more amino acids) directly N-terminal of the junction, which peptide fragments each can include or span the junction of the two domains. Thus, in some cases, the junction region can contain a plurality of potential peptide epitopes that may exhibit a binding affinity for an HLA molecule and/or be capable of inducing an immune response.

In some embodiments, an immunogenic region, such as a junction region, of a chimeric receptor can be identified. In some embodiments, the immunogenic region can be identified by its ability to bind to an MHC molecule or by its ability to elicit an immune response under certain conditions. In some embodiments, overlapping peptides of a chimeric receptor, such as overlapping 8mer to 20 mer peptides, such as 9mers, 10mers, 11mers, 12mers, 13mers, 14mers or 15mers can be assessed for MHC binding using algorithmic or other computational methods, such as described below. In some embodiments, a chimeric receptor can be assessed to determine if it is immunogenic by assessing an immune response in a subject to which it has been administered, such as a subject administered cells genetically engineered with the chimeric receptor (e.g. CAR). Exemplary methods of assessing immune responses are described below.

In some embodiments, the at least one peptide epitope is capable of binding to a major histocompatibility complex (MHC) molecule, such as a class I or class II protein, which are molecules that contain a polymorphic peptide binding site or binding groove that can, in some cases, complex with peptide fragments of polypeptides, including peptides processed by the cell machinery. In some embodiments, the peptide epitope is capable of binding to an MHC molecule that is a human MHC molecule. In some embodiments, the MHC molecule is a human leukocyte antigen (HLA) molecule. In some embodiments, the at least one peptide epitope exhibits a binding affinity (e.g. IC50) for an HLA molecule, such as an HLA class I molecule or an HLA class II molecule. In some embodiments, the junction region of the reference chimeric receptor contains a peptide epitope that exhibits a binding affinity of less than 1000 nM, less than 500 nM or less than 50 nM.

In some embodiments, at least one or more peptide epitopes of a junction region of a reference chimeric receptor is an MHC class II epitope. In some embodiments, peptides that bind to MHC class II molecules can be between 8 and 20 amino acids in length, including between 10 and 17 amino acids in length. In some embodiments, the peptides that bind to MHC class II molecules can be longer than 20 amino acids. In some embodiments, the peptide lies in an extended conformation along the MHC II peptide-binding groove. In some embodiments, the MHC II peptide-binding groove is open at both ends. In some embodiments, the peptide is held in place at least in part by main-chain atom contacts with conserved residues that line the peptide-binding groove. In some embodiments, the MHC class II allele can be any known to be present in a subject, such as a human subject. In some embodiments, the MHC allele can be, but is not limited to, DR1, DR3, DR4, DR7, DR52, DQ1, DQ2, DQ4, DQ8 and DP1. In some embodiments, the MHC class II allele can be any set forth in Tables 1B. In some embodiments, the MHC class II allele is an HLA-DRB1*0101, an HLA-DRB*0301, HLA-DRB*0701, HLA-DRB*0401 an HLA-DQB1*0201.

In some embodiments, the at least one peptide epitope of a junction region of a reference chimeric receptor is an MHC class I epitope. In some embodiments, peptides that bind to MHC class I molecules can be between 7 to 15 amino acids in length. In some embodiments, peptides that bind to MHC class I molecule can be between 8 to 13 amino acids in length. In some embodiments, the binding of the peptide is stabilized at its two ends by contacts between atoms in the main chain of the peptide and invariant sites in the peptide-binding groove of all MHC class I molecules. In some embodiments, there are invariant sites at both ends of the groove which bind the amino and carboxy termini of the peptide. In some embodiments, variations in peptide length can be accommodated by a kink in the peptide backbone. In some embodiments, the kink includes proline or glycine residues, which may allow flexibility. In some embodiments, the MHC class I allele can be any known to be present in a subject, such as a human subject. In some embodiments, the MHC class I allele is an HLA-A2, HLA-A1, HLA-A3, HLA-A24, HLA-A28, HLA-A31, HLA-A33, HLA-A34, HLA-B7, HLA-B45 or HLA-Cw8 allele. In some embodiments, the MHC class I allele can be any set forth in Tables 1A, which are among the most frequent MHC class I alleles (Solberg et al., (2008) Hum Immunol. 2008 July; 69(7):443-6). In some embodiments, the HLA class I allele is HLA-A*02:01, HLA-A*03:01, HLA-A*11:01 or HLA-B*08:01.

In some embodiments, the MHC class I allele is an HLA-A2 allele, which in some populations is expressed by approximately 50% of the population. In some embodiments, the HLA-A2 allele can be an HLA-A*0201, *0202, *0203, *0206, or *0207 gene product. In some cases, there can be differences in the frequency of subtypes between different populations. For example, in some embodiments, more than 95% of the HLA-A2 positive Caucasian population is HLA-A*0201, whereas in the Chinese population the frequency has been reported to be approximately 23%

HLA-A*0201, 45% HLA-A*0207, 8% HLA-A*0206 and 23% HLA-A*0203. In some embodiments, the MHC molecule is HLA-A*0201.

In some embodiments, the second chimeric receptor is a variant chimeric receptor containing a modified junction region compared to a junction region of reference chimeric receptor, which can be the first chimeric receptor, in which one or more amino acid residues at a position 8 to 24 amino acids (e.g. 8 to 15 amino acids or 8 to 13 amino acids, such as about or 8, 9, 10, 11, 12, 13, 14, 15 or more amino acids) directly C-terminal of the junction that joins a first domain and a second domain of the reference chimeric receptor and/or at a position 8 to 24 amino acids (e.g. 8 to 15 amino acids or 8 to 13 amino acids, such as about or 8, 9, 10, 11, 12, 13, 14, 15 or more amino acids) directly N-terminal of the junction are modified, such as by insertion, deletion or amino acid replacement. In some embodiments, the variant chimeric receptor contains up to 1, 2, 3, 4, 5, 6, 7, 8, 9, 10, 11, 12, 13, 14, 15, 16, 17, 18, 19 or 20 amino acid differences or modifications in the modified junction region compared to the junction region in the reference chimeric receptor.

In some embodiments, the variant chimeric receptor contains a domain of at least 85%, 86%, 87%, 88%, 89%, 90%, 91%, 92%, 93%, 94%, 95%, 96%, 97%, 98%, 99% or more sequence identity to the first domain of the reference chimeric receptor and/or contains a domain of at least 85%, 86%, 87%, 88%, 89%, 90%, 91%, 92%, 93%, 94%, 95%, 96%, 97%, 98%, 99% or more sequence identity to the second domain of the reference chimeric receptor. In some embodiments, the variant chimeric receptor contains a domain that is identical in sequence to the first domain of the reference chimeric receptor and contains a domain of at least 85%, 86%, 87%, 88%, 89%, 90%, 91%, 92%, 93%, 94%, 95%, 96%, 97%, 98%, 99% or more sequence identity to the second domain of the reference chimeric receptor. In some embodiments, the variant chimeric receptor contains a domain of at least 85%, 86%, 87%, 88%, 89%, 90%, 91%, 92%, 93%, 94%, 95%, 96%, 97%, 98%, 99% or more sequence identity to the first domain of the reference chimeric receptor and contains a domain that is identical in sequence to the second domain of the reference chimeric receptor. In some embodiments, at least one or both of the domains present in the variant chimeric receptor is modified compared to the first domain and/or the second domain of the reference chimeric receptor in the portion containing the modified junction region.

In some embodiments, the variant chimeric receptor has at least 85%, 86%, 87%, 88%, 89%, 90%, 91%, 92%, 93%, 94%, 95%, 96%, 97%, 98%, 99% or more sequence identity to the reference chimeric receptor. In some embodiments, the variant chimeric receptor contains up to 1, 2, 3, 4, 5, 6, 7, 8, 9, 10, 11, 12, 13, 14, 15, 16, 17, 18, 19 or 20 amino acid differences or modifications (e.g. amino acid insertions, deletions or replacements) compared to the reference chimeric receptor.

In some embodiments, the first and/or second domain of the reference chimeric receptor (e.g. reference CAR) is a domain of a natural endogenous human protein or a domain having 100% identity with a domain or function portion thereof of a natural or endogenous protein. In some embodiments, the first domain and second domain are not present in the same molecule in vivo in a human subject. In some embodiments, the first domain and second domain are not present in a single natural or endogenous human protein or polypeptide.

In some embodiments, the first and/or second domain is or comprises an extracellular binding domain, a hinge domain, a transmembrane domain, or an intracellular signaling domain or functional portions thereof. In some embodiments, the intracellular signaling domain is or comprises a costimulatory signaling domain, such as a CD28, 4-1BB, or ICOS co-stimulatory signaling domain. In some embodiments, the intracellular signaling domain is or comprises an activating cytoplasmic signaling domain, such as a domain that is or includes a T cell receptor (TCR) component and/or that contains an immunoreceptor tyrosine-based activation motif (ITAM). In some cases, the activating cytoplasmic domain is or comprises a cytoplasmic signaling domain of a zeta chain of a CD3-zeta (CD3) chain or a functional variant or signaling portion thereof.

In some embodiments, the reference chimeric receptor is a CAR. In some embodiments, the chimeric receptors, such as a CAR, contains from its N-terminus to C-terminus in order: an extracellular ligand-binding domain, a transmembrane domain and an intracellular signaling domain. In some embodiments, the intracellular signaling domain is or includes an activating signaling domain (e.g. a components of TCR and/or containing an ITAM, for example a CD3-zeta signaling domain). In some embodiments, the intracellular signaling domain is or includes a costimulatory signaling domain (e.g. a CD28, 4-1BB or ICOS signaling domain). In some embodiments, the intracellular signaling domain contains only one of the costimulatory signaling domain or activating signaling domain or contains both domains in either order. In some embodiments, the intracellular signaling domain contains both the costimulatory signaling domain and activating signaling domain.

In some embodiments, the variant chimeric receptor can contain from its N-terminus to C-terminus in order: an extracellular ligand-binding domain, a transmembrane domain and an intracellular signaling domain, which optionally can include a costimulatory signaling domain (e.g. CD28, 4-1BB or ICOS) and/or an activating signaling domain (e.g. a components of TCR and/or containing an ITAM, for example a CD3-zeta signaling domain) each alone as part of the intracellular signaling domain or in either order, in which the variant chimeric receptor contains a modification at one or more amino acid residues within a contiguous portion of 8 to 24 amino acids (e.g. 8 to 15 amino acids or 8 to 13 amino acids, such as about or 8, 9, 10, 11, 12, 13, 14, 15 or more amino acids) on either side (N-terminal and/or C-terminal) of the junction.

In some embodiments, the features of a reference chimeric receptor can be any described in subsection III below. In some embodiments, the features of a variant chimeric receptor also can be any as described in subsection III below, except that the variant chimeric receptor contains one or more modifications (e.g. insertions, deletions or replacements) in a modified junction region as described.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises an extracellular ligand binding domain or a portion thereof and a second domain that is or comprises a hinge domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a hinge domain or a portion thereof and a second domain that is or comprises a transmembrane domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a transmembrane domain or a portion thereof and a second domain that is or comprises a costimulatory signaling domain or a portion thereof, joined in contiguous sequence at a junction.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a costimulatory signaling domain or a portion thereof and a second domain that is or comprises an activating cytoplasmic signaling domain or a portion thereof, joined in contiguous sequence at a junction.

In some embodiments, the first domain of the reference chimeric receptor is or comprises a transmembrane domain or a portion thereof. In some embodiments, the transmembrane domain include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. In some embodiments, the second domain of the reference chimeric receptor is or comprises a costimulatory signaling domain, which is directly linked or joined to the transmembrane domain. In some embodiments, the costimulatory signaling domain is or comprises a signaling domain of CD28, 4-1BB, OX40, DAP10, and ICOS.

In some embodiments, the variant chimeric receptor contains a modified junction region containing one or more modifications (e.g. insertions, deletions or replacements) in a junction region of a reference chimeric receptor as described, wherein the reference chimeric receptor contains a first domain that is or comprises a CD28 transmembrane domain or a portion thereof and a second domain that is or comprises a 4-1BB costimulatory signaling domain or a portion thereof, joined in contiguous sequence at a junction. In some embodiments, the CD28 transmembrane domain is or comprises the sequence of amino acids set forth in SEQ ID NO:2, 103 or 104 or is a functional portion or variant thereof comprising a sequence that exhibits at least 85%, 86%, 87%, 88%, 89%, 90%, 91%, 92%, 93%, 94%, 95%, 96%, 97%, 98%, 99% or more sequence identity to SEQ ID NO:2, 103 or 104. In some embodiments the 4-1BB signaling domain is or comprises the sequence of amino acids set forth in SEQ ID NO:3 or a functional portion or variant thereof comprising a sequence that exhibits at least 85%, 86%, 87%, 88%, 89%, 90%, 91%, 92%, 93%, 94%, 95%, 96%, 97%, 98%, 99% sequence identity to SEQ ID NO:3. In some embodiments, the first domain and second domain together comprise or have the sequence of amino acids set forth in SEQ ID NO:5 or a functional portion or variant thereof comprising a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:5. In some embodiments, the first domain and second domain of the reference chimeric receptor together have or comprise the sequence of amino acids set forth in SEQ ID NO:5.

In some embodiments, the variant chimeric receptor comprises a modified junction region that is less than 100% sequence identity to SEQ ID NO:137 but greater than 85%, 86%, 87%, 88%, 89%, 90%, 91%, 92%, 93%, 94%, 95% or 96% to SEQ ID NO:137 and includes the modifications. In some embodiments, the variant chimeric receptor has or comprises a sequence of amino acids that is less than 100% sequence identity to SEQ ID NO:5 but greater than 85%, 86%, 87%, 88%, 89%, 90%, 91%, 92%, 93%, 94%, 95% or 96% to SEQ ID NO:5 and includes the modifications. In some embodiments, the variant chimeric receptor has or comprises a modified junction region comprising the sequence of amino acids set forth in any of SEQ ID NOS: 138-157, a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 138-157, or a functional portion thereof, each that include the modification(s).

In some embodiments, the variant chimeric receptor does not contain a modification at or of a hydrophobic amino acid residue or within a hydrophobic portion in the transmembrane domain, such as the CD28 transmembrane domain. In some embodiments, the variant chimeric receptor contains one or more modifications at or of a hydrophobic amino acid residues or within a hydrophobic portion in the transmembrane domain, such as the CD28 transmembrane domain. In some embodiments, the one or more modifications is or comprises a substitution of the hydrophobic amino acid with another different hydrophobic amino acid residue. In some embodiments, the one or more modifications is not or does not comprise a modification at or of a hydrophobic amino acid residue or within a hydrophobic portion in the transmembrane domain other than a substitution with another hydrophobic amino acid residue.

In some cases, transmembrane domains contain one or more tryptophan residues that interact with the lipid bilayers of a membrane. In some cases, the one or more tryptophan residues can be located near the lipid-water interface. In some cases, the one or more tryptophan residues anchor or assist in anchoring the transmembrane domain within the membrane. See e.g. de Jesus and Allen, *Biochim Biophys Acta.* 2013 February; 1828(2):864-76. In some embodiments, the variant chimeric receptor does not contain a modification at one or both of a tryptophan residue in the transmembrane domain, such as the CD28 transmembrane domain. In some embodiments, the chimeric receptor does not contain a modification at an amino acid position corresponding to position 2 and/or position 26 with reference to numbering of SEQ ID NO: 5, each of which corresponds to a tryptophan in the reference chimeric receptor.

In some embodiments, the domain in the variant chimeric receptor that corresponds to the transmembrane domain of the reference chimeric receptor has a substantially hydrophobic hydropathy profile and/or has a grand average of hydopathy (GRAVY) value of greater than 1.6, 1.7, 1.8, 1.9, 2.0, 2.1, 2.2 or greater.

In some embodiments, the variant chimeric receptor does not contain a modification at or of an amino acid residue involved in or necessary for the signaling of the costimulatory signaling domain, such as at or of an amino acid residue involved in or necessary for 4-1BB signaling. In general, costimulatory signaling involves interactions with TRAF molecules. In some embodiments, the variant chimeric receptor does not contain a modification at or of an amino acid residue that interacts with or is part of a binding motif for binding to a TRAF molecule. In some embodiments, the variant chimeric receptor does not contain a modification at or of an amino acid residue in the costimulatory signaling domain of the reference chimeric receptor that comprises the motif (P/S/A/T)X(Q/E)E. In some embodiments, the TRAF molecule is TRAF 1, TRAF2 and/or TRAF3. In some embodiments, the domain in the variant chimeric receptor that corresponds to the costimulatory signaling domain of the reference chimeric receptor is capable of inducing the activation or cellular localization of a TRAF and/or is capable of inducing TRAF-mediated signaling. In some embodiments, the variant chimeric receptor contains amino acids TTQE at positions corresponding to 49-52 and/or amino acids PEEE at positions corresponding to residues 60-63, each with reference to numbering set forth in SEQ ID NO:5.

In some embodiments, the variant chimeric receptor contains one or more amino acid modification within a portion between residue 13 and 42 or between amino acid residue 15 and 40, with reference to numbering set forth in SEQ ID NO:5.

In some embodiments, the modification is or includes insertion of one or more amino acid residues. In some embodiments, the one or more insertion is between amino acid residues adjacent to the junction between the domains. In some embodiments, the one or more amino acid insertions is between amino acid residues 27 and 28 with reference to numbering set forth in SEQ ID NO:5. In some embodiments, the one or more insertions can include insertion of up to 1, 2, 3, 4, 5, 6, 7, 8, 9, 10, 11, 12, 13, 14 or 15 amino acid residues. In some embodiments, the insertion is of 1, 2, 3, 4, or 5 amino acid residues. In some embodiments, the insertion is to any amino acid residues. In some embodiments, the insertion of is insertion of an asparagine (N).

In some embodiments, the modification is or includes one or more amino acid replacements at a residue corresponding to residue 28, 31 or 34 with reference to numbering set forth in SEQ ID NO:5. In some embodiments, the amino acid replacement can be to any other amino acid. In some embodiments, the amino acid replacement is to an amino acid residue that is leucine (L), asparagine (N), glutamine (Q), alanine (A), serine (S) or histidine (H). In some embodiments, the amino acid replacement is or corresponds to one or more of K28A, K28H, K28L, K28Q, K28S, R31A, R31H, R31L, R31N, L34A and L34S, with reference to numbering set forth in SEQ ID NO:5.

In some embodiments, the variant chimeric receptor contains a modified junction region with two or more, such as up to 2, 3, 4, 5, 6, 7, 8, 9, 10 or more amino acid modifications compared to a junction region of a reference chimeric receptor. In some embodiments, the amino acid replacements are or correspond to amino acid replacements selected from among K28Q/R31A, K28Q/R31N, K28Q/R31S, K28Q/L34A, K28Q/L34S, R31N/L34A, R31N/L34S, K28Q/R31N/L34A, K28Q/R31N/L34S.

In some embodiments, the variant chimeric receptor has or comprises a modified junction region that has the sequence of amino acids set forth in any of SEQ ID NOS: 138-157, a a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 138-157, or a functional portion thereof, each that includes the modification(s).

In some embodiments, the variant chimeric receptor has or comprises the sequence of amino acids set forth in any of SEQ ID NOS: 114-134, a functional variant thereof comprising a sequence of amino acids that exhibits at least 85%, 86%, 87%, 88%, 89%, 90%, 91%, 92%, 93%, 94%, 95% or 96% sequence identity to the sequence of amino acids set forth in any of SEQ ID NOS: 114-134, or a functional portion thereof, each that includes the modification(s).

In some embodiments, the variant chimeric receptor contains a modified junction region such that peptide fragments of such region exhibit a lower binding affinity for a human leukocyte antigen (HLA) and/or the region exhibits reduced immunogenicity, including following administration to a subject.

In some embodiments, a peptide fragment having the sequence of an 8-15 amino acid portion of the modified junction region has a binding affinity for a human leukocyte antigen (HLA) molecule that is lower than the binding affinity, for the same HLA molecule, of a peptide fragment having the sequence of the corresponding portion of the junction region of the reference chimeric receptor. In some embodiments, the peptide fragment of the corresponding portion of the junction region of the reference chimeric receptor has a binding affinity of less than 1000 nM, less than 500 nM or less than 50 nM.

In some embodiments, the average of the binding affinities of all 8-15 amino acid fragments, or of all 8, 9, 10, 11, 12, 13, 14, or 15 amino acid fragments, within the modified junction region for a human HLA molecule is lower than the average of the binding affinities of all 8-15 amino acid fragments, or of all 8, 9, 10, 11, 12, 13, 14, or 15 amino acid fragments, within the junction region of the reference chimeric receptor. In some embodiments, the binding affinity or average of binding affinities is more than 2-fold, more than 5-fold, more than 10-fold, more than 25-fold, more than 50-fold or more than 100-fold lower.

In some embodiments, the number of peptide fragments having the sequence of an 8-15 amino acid portion of the modified junction region that has a binding affinity for a human leukocyte antigen (HLA) of less than 1000 nM is reduced compared to the number of peptide fragments having the sequence of an 8-15 amino acid portion of the junction region of the reference chimeric receptor that has the same affinity for binding the same HLA. In some embodiments, the number of peptide fragments having the sequence of an 8-15 amino acid portion of the modified junction region that has a binding affinity for a human leukocyte antigen (HLA) of less than 500 nM is reduced compared to the number of peptide fragments having the sequence of an 8-15 amino acid portion of the junction region of the reference chimeric receptor that has the same affinity for binding the same HLA. In some embodiments, the number of peptide fragments having the sequence of an 8-15 amino acid portion of the modified junction region that has a binding affinity for a human leukocyte antigen (HLA) of less than 50 nM is reduced compared to the number of peptide fragments having the sequence of an 8-15 amino acid portion of the junction region of the reference chimeric receptor that has the same affinity for binding the same HLA.

In some embodiments, the binding affinity can be determined experimentally or algorithmically. In some embodiments, a peptide binding affinity for an MHC can be determined computationally, such as by using algorithms based on quantitative binding affinity models (Lafuente and Reche (2009) Current Pharmaceutical Design, 15:3209-3220). In some embodiments, the binding affinity can be determined in an in vitro assay.

In some embodiments, determining a peptide's binding affinity to an MHC molecule involves radioactivity or fluorescence competition binding assays. See, e.g. Ettinger et al., *J. Immunol.* 160:2365 (1998). In some embodiments, the competition assay yield a comparison of binding affinities of different peptides. Some MHC binding studies utilize detergent solubilized class I molecules from EBV transformed cell lines (see, e.g. Sette, A., et al., *Mol Immunol*, 31(11): 813-22 (1994). In some embodiments, the competitive assay involves naturally loaded MHC, and the MHC molecule of interest can be purified away from other MHC molecules in the detergent lysate or be used in a mixture with other MHC molecules. In some embodiments, radiolabeled peptides can be identified that have a high affinity for the MHC molecule in question. In some embodiments, the affinity of additional "test" peptides for the MHC molecule in question is then determined by their ability to compete with the high affinity radiolabeled peptide.

In some embodiments, determining peptide affinity can involve a reconstitution assay, e.g. using "T2" cells, in which cells expressing an appropriate MHC allele are "stripped" of a native binding peptide by incubating at pH 2-3 for a short period of time. In some embodiments, to determine the binding affinity of a putative MHC-binding peptide for the same MHC allele, the stripped MHC monomer can be combined in solution with the putative MHC-binding peptide, beta2-microglobulin and a conformation-dependent monoclonal antibody. In some embodiments, the difference in fluorescence intensity determined between cells incubated with and without the test binding peptide after labeling, for example, either directly with the labeled monoclonal antibody or a fluorescence-labeled secondary antibody, can be used to determine binding of the test peptide.

In some embodiments, the binding affinity for an MHC (e.g. HLA) molecule is represented by an IC50, which is the concentration of peptide in a binding assay at which 50% inhibition of binding of a reference peptide is observed. In some cases, such assays can be run under conditions in which IC50 values approximate $K_D$ values (i. e., limiting HLA proteins and labeled peptide concentrations). In some embodiments, binding can be expressed relative to a reference peptide.

In some embodiments, the binding affinity can be predicted using in silico methods. Exemplary in silico methods for predicting binding affinity for MHC binding using algorithmic or other computational methods are known in the art, See, for example, Marsh, et al., *The HLA Factsbook* (Academic Press, 2000). In some embodiments, an algorithm can be used to predict if a peptide of interest should bind to a given MHC molecule. See, e.g., Southwood, et al., *J. Immunol.* 160:3363 (1998); Honeyman, et al., *Nat. Biotechnol.* 16:966-969 (1998); Breisie, et al., *Bioinformatics* 14:121-131 (1998), as well as the "SYFPEITHI" algorithm (Hans-Georg Rammensee, et al., *Immunogenetics* (1999) 50: 213-219), Zhang et al., *PLoS ONE* 7(2): e30483. doi: 10.1371/journal.pone.0030483, the Immune Epitope and Analysis Resource (IEDB) (Peters B, et al. *PLoS Biology* 3: 379 (2005)), and the "BIMAS" algorithm (Parker, K. C., M. A. Bednarek, and J. E. Coligan. *J. Immunol.* 152:163 (1994).

In some embodiments, algorithm prediction tools, including those available from IEDB, use one or more predictions using ANN (Nielsen et al. (2003) Protein Sci., 12:1007-1017 and Lundegaard et al. (2008) NAR, 36:W509-512), SMM (Peters and Sette (2005) BMC Bioinformatics, 6:132) and comblib (Sidney et al. (2008) Immunome Res. 4:2), or the Consensus tool (see Kim, et al. (2012) Immune epitope database analysis resource, NAR, combining predictions from any of the foregoing).

In some embodiments, prediction of antigen processing can be accomplished using an algorithm for proteosomal cleavage (PaProC). See Kuttler et al., *J. Mol. Biol.* 298 (2000), 417-429 and Nussbaum et al., *Immunogenetics* 53 (2001), 87-94.

In some embodiments, the variant chimeric receptor, which can be the second chimeric receptor, exhibits a reduction in a detectable immune response compared to the reference chimeric receptor, which can be the first chimeric receptor. In some embodiments, the immune response is a humoral immune response. In some embodiments, the immune response is a cell-mediated immune response. In some embodiments, the immune response is reduced greater than 1.5-fold, 2-fold, 3-fold, 4-fold, 5-fold, 6-fold, 7-fold, 8-fold, 9-fold, 10-fold, 50-fold, 100-fold or more. In some embodiments, the immune response is assessed in vitro. In some embodiments, the immune response is assessed in vivo upon administration of a chimeric receptor to a subject, such as administration of cells expressing a chimeric receptor. In some embodiments, a host immune response to the chimeric receptor is assessed as described below.

II. Administration of Cells in Adoptive Cell Therapy

The provided methods generally involve administering multiple doses of cells expressing recombinant molecules such as recombinant receptors, such as CARs, other chimeric receptors, or other antigen receptors, such as transgenic TCRs, to subjects having a disease or condition, such as a disease or condition a component of which is specifically recognized by and/or treated by the recombinant molecules, e.g., receptors. The administrations generally effect an improvement in one or more symptoms of the disease or condition and/or treat or prevent the disease or condition or symptom thereof.

As used herein, a "subject" is a mammal, such as a human or other animal, and typically is human. In some embodiments, the subject has been treated with a therapeutic agent targeting the disease or condition prior to one or more of the administrations or doses. In some aspects, the subject is or becomes refractory or non-responsive to the other therapeutic agent. In some embodiments, the subject has not become refractory or non-responsive but the administration of the cells expressing the second or subsequent receptor is carried out prophylactically, for example, to prevent the subject from becoming refractory or resistant to treatment.

In some embodiments, the subject at the time or immediately prior to one or more of the administrations has persistent or relapsed disease. For example, disease may have relapsed following treatment with another therapeutic intervention, including chemotherapy, radiation, and/or hematopoietic stem cell transplantation (HSCT), e.g., allogeneic HSCT or become refractory to such treatment. The disease or condition may have relapsed or become refractory to the cells of the first administration or dose prior to or at the time of the second administration. In some embodiments, the administration effectively treats the subject despite the subject having become resistant to another therapy, such as a therapy other than adoptive cell therapy, or an adoptive cell therapy, such as the first administration of cells expressing a distinct receptor.

In some embodiments, the subject is responsive to the other therapeutic agent or cell administration and treatment with the therapeutic agent or administration reduces disease burden. In some aspects, the subject is initially responsive to the therapeutic agent or administration, but exhibits a relapse of the disease or condition over time, e.g., at which point administration of the cell therapy or second dose or administration is carried out. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse.

In some embodiments, the subject has not received prior treatment with another therapeutic agent. In some embodiments, the subject has not received a dose of cells expressing a receptor, e.g. CAR, prior to the administration of the first dose and/or has not received a dose of cells expressing the CAR or other receptor expressed by such cells or expressing any recombinant receptor targeting the same molecule or antigen. In some embodiments, the subject has not received a dose of cells expressing the receptor of the first dose prior to the administration of the first dose. In other embodiments, multiple doses of the cells of the first and/or second administration are given.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or condition is a tumor and the subject has a large tumor burden prior to the administration of the first dose, such as a large solid tumor or a large number or bulk of disease-associated, e.g., tumor, cells. In some aspects, the subject has a high number of metastases and/or widespread localization of metastases. In some aspects, the tumor burden in the subject is low and the subject has few metastases. In some embodiments, the size or timing of the doses is determined by the initial disease burden in the subject. For example, whereas in some aspects the subject may be administered a relatively low number of cells in the first dose, in context of lower disease burden the dose may be higher.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, OEPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply necessarily complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical or similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intrathoracic, intracranial, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or other agent, such as a cytotoxic or therapeutic agent. Thus, the cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2 or other cytokine, for example, to enhance persistence.

In some embodiments, the methods comprise administration of a chemotherapeutic agent, e.g., a conditioning chemotherapeutic agent, for example, to reduce tumor burden prior to the dose administrations.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In certain embodiments, engineered cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

III. Recombinant Receptors Expressed by the Cells

The cells generally express recombinant receptors. The receptors expressed by the cells of the different doses typically are distinct from one another, at least in part. The receptors may include antigen receptors, such as functional non-TCR antigen receptors, including chimeric antigen receptors (CARs), and other antigen-binding receptors such as transgenic T cell receptors (TCRs). The receptors may also include other chimeric receptors, such as receptors binding to particular ligands and having transmembrane and/or intracellular signaling domains similar to those present in a CAR.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 March 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, *Nature Reviews Clinical Oncology*, 10, 267-276 (2013); Wang et al. (2012) *J. Immunother.* 35(9): 689-701; and Brentjens et al., *Sci Transl Med.* 2013 5(177). See also International Patent Publication No.: WO2014031687, U.S. Pat. Nos. 8,339,645, 7,446,179, 7,446,190, and 8,389,282, and U.S. patent application Publication No. US 2013/0149337. Among the chimeric receptors are chimeric antigen receptors (CARs). The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the binding domain(s), e.g., the antibody, e.g., antibody fragment, portion of the recombinant receptor further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 158. In some embodiments, the spacer has the sequence set forth in SEQ ID NO: 107. In some embodiments, the spacer has the sequence set forth in SEQ ID NO: 108. In some embodiments, the constant region or portion is of IgD. In some embodiments, the spacer has the sequence set forth in SEQ ID NO: 109. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 107, 108 or 109.

This antigen recognition domain generally is linked to one or more intracellular signaling components, such as signaling components that mimic activation through an antigen receptor complex, such as a TCR complex, and/or signal via another cell surface receptor. The signal may be immunostimulatory and/or costimulatory in some embodiments. In some embodiments, it may be suppressive, e.g., immunosuppressive. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. The transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence derived from a signaling molecule or domain that promotes primary activation of a TCR complex in a natural setting. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from the CD3 zeta chain, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen, present on the same cell. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine*, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD 137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 111 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 111. An exemplary T2A linker sequence comprises the sequence of amino acids set forth in SEQ ID NO: 110 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 110.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antigen-binding domain, such as an antibody or antigen-binding antibody fragment, such as an scFv or Fv. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 2 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 2; in some embodiments, the transmembrane-domain containing portion of the recombinant receptor comprises the sequence of amino acids set forth in SEQ ID NO: 104 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 41BB.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 112 or 113 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 112 or 113. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 3 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 3.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. Nos. 7,446,190 or 8,911,993. For example, in some embodiments, the intracellular signaling domain comprises the sequence of amino acids as set forth in SEQ ID NO: 4, 105 or 159 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 4, 105 or 159.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 108. In some embodiments, the spacer is an Ig hinge, e.g., an IgG4 hinge, linked to a CH3 domain only, such as set forth in SEQ ID NO: 107. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 110, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 110. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO:111, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 111.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

The recombinant receptors, such as CARs, expressed by the cells administered to the subject in the various doses generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells in the first dose express a receptor, e.g., CAR, that specifically binds to an antigen expressed by a cell or tissue of the disease or condition or associated with the disease or condition.

In some embodiments, the cells in the subsequent dose express a receptor, e.g., CAR, that specifically binds to an antigen expressed by a cell or tissue of the disease or condition or associated with the disease or condition. In some aspects, the receptor expressed by the cells of the second dose specifically binds the same antigen as, or competes for binding with, the receptor of the first dose. In other embodiments, the receptor expressed by the cells of the second dose specifically binds to a different antigen than that bound by the receptor of the first dose.

Thus, in some embodiments, the second receptor (e.g., the second CAR) differs to some degree, e.g., in amino acid sequence and/or immunological epitope(s), from the first receptor (e.g. first CAR). For example, in some aspects, the receptor, e.g., the CAR, expressed by the cells administered in the first dose contains at least one immunoreactive epitope that is not expressed by the cells of the subsequent dose. In some embodiments, the receptor, e.g., CAR, expressed by the cells of the second dose, does not contain an immunoreactive epitope expressed by the cells of the first dose. Exemplary immunoreactive epitopes include B cell epitopes and T cell epitopes, which may be recognized by the immune system of the subject to which the cells are administered.

Thus, in some embodiments, one or more component of the CAR of the subsequent dose is distinct from the CAR of the first dose. In some embodiments, the second (or subsequent) receptor, e.g., CAR, includes one or more differences in amino acid sequence compared to the first or prior receptor. For example, in some aspects, the CAR expressed by the cells of the subsequent dose contains a distinct scFv, distinct signaling domains, and/or distinct junctions as compared to the CAR expressed by the cells of the first dose. In some embodiments, sequences in the first and/or second receptor or other molecule that are non-endogenous to the host, e.g., not present as such in a molecule present naturally in the host. Exemplary of such non-endogenous sequences are sequences spanning the junctions of non-naturally associated or fused domains within a chimeric molecule, such as a CAR. In some embodiments, the CAR expressed by the cells of the subsequent dose contains distinct costimulatory, stimulatory, transmembrane, and/or other domains from that of the first dose.

Such differences may include at least one difference compared to a region of the first or prior receptor to which a detectable immune response is exhibited in the subject following the first or prior administration, e.g., a difference in a region in the second or subsequent receptor that corresponds to such a region in the first or prior receptor. Regions including the difference(s) may include an antigen-binding portion, such as an scFv portion, including framework region(s) within an scFv or variable region portion, such as a heavy and/or light chain variable region portion, a linker portion, a hinge portion, a junction between two CAR domains, and/or a transduction or expression marker.

In some embodiments, the first or other prior and second or other subsequent receptors may include regions of similarity, e.g., regions of amino acid sequence identity. For example, in some embodiments, the CAR expressed by the cells of the subsequent dose contains the same scFv, the same signaling domains, and/or the same junctions as the CAR expressed by the cells of the first dose. In some embodiments, it further contains the same costimulatory, stimulatory, transmembrane, and/or other domains as that of the first dose.

In some aspects, the region(s) of identity are ones to which the subject does not or is unlikely to exhibit an immune response following the first or prior administration. Such regions may include regions within a costimulatory domain, an ITAM-containing domain, a transmembrane domain, a CDR, and/or a transduction or expression marker.

In some aspects, the antigen-binding domains, such as the antibody or antibody fragments and/or domains thereof, e.g., light and/or heavy chain variable regions, e.g., scFvs, of the second receptor, e.g., second CAR, is or are derived from a different species than that or those of the first receptor, e.g., first CAR. Exemplary species from which such domains or fragments may be derived include human and non-human species, such as mouse. For example, in some embodiments, an scFv of a first or prior CAR is derived from mouse antibody or antibody with a murine-derived portion, such as an FMC63 or SJ25C1 scFv, and the scFv of the second or subsequent CAR is derived from a human antibody or antibody fragment, or vice versa.

In some embodiments, the antigen-binding domain, e.g., antibody portion or fragment, e.g., scFv, of the first CAR and that of the second CAR are derived from the same species. In some such embodiments, the domain of the first and second receptors are derived from the same species but contain one or more differences in sequence. In some aspects, the scFv of the first CAR is derived from a mouse sequence, e.g., FMC63, and the scFv of the second CAR is derived from a distinct mouse sequence, e.g., SJ25C1, or vice versa.

In some aspects, the receptor, e.g., CAR, of the second dose contains the same antigen binding domain, e.g., antibody fragment or portion, e.g., scFv, as the receptor, e.g., CAR, of the first dose. In some embodiments, such a subsequent or second receptor contains one or more distinct junctional region as compared to the CAR of the first or prior dose.

In some such embodiments, administration of cells expressing the second or subsequent CAR results in reduced elimination of the cells of the second or subsequent dose as compared to a method in which the second CAR contains the same junction or junctions as the cells of the first dose and/or contains non-endogenous sequence(s) present in the receptor of the first dose.

In some aspects, the first and second receptor target the same antigen. In some embodiments, the first and second receptor target the same epitope of the antigen. For example, in some embodiments, the first and second receptor target the same or an overlapping epitope and/or compete for binding to the antigen with one another, but are derived from different species, such as mouse and human, respectively. In other embodiments, the first and second receptor target different epitopes on the same antigen.

In some embodiments, the second molecule, e.g., receptor, e.g., CAR, does not include one or more immunogenic portion(s) contained in the first; in some embodiments, the second receptor does not contain any immunogenic portions in the first receptor (or portions deemed to be immunogenic by a specified assay). In some such embodiments, the second receptor, e.g., CAR, is specifically chosen and/or designed so that it does not include an immunogenic portion(s) contained in the first receptor and/or does not contain a portion deemed to be immunogenic, e.g., in a particular subject and/or to which a specific immune response has been detected, e.g., in the subject being treated. In some aspects, the immunogenic portion(s) of the first receptor, e.g., CAR, has/have been replaced with a distinct sequence or distinct sequences.

In some embodiments, such as where the subject has become resistant to treatment targeting the antigen or other binding partner targeted by the first receptor or molecule, and/or where the antigen or binding partner is or has been down-regulated or mutated in the subject or disease tissue (e.g., tumor), the receptor (e.g., CAR) of the second dose is designed or chosen to target a distinct antigen as compared to that targeted by the receptor of the first dose. In some such aspects, administration of the second dose (i.e. the cells expressing the second molecule, e.g., second receptor) effects a larger reduction in disease burden in the subject, e.g., tumor burden, than administration of a subsequent dose of the same cells, cells expressing the same receptor, and/or containing cells expressing a receptor that targets the same antigen.

In this respect, the methods in some embodiments may be useful in treating subjects whose disease or condition has become resistant to treatments targeting a particular epitope or antigen or other disease target, such as resulting from down-regulation or mutation by the disease or condition or cells thereof. Thus, by offering the ability to target a similar but distinct disease-associated epitope or disease, the methods in some embodiments improve efficacy not only by increasing overall exposure of the subject to cells expressing the receptors or other recombinant molecules, e.g., via increased expansion or persistence of such engineered cells in the subject, but also by allowing the cells to function even in the context of downregulation or mutation of the original target.

IV. Host Immune Responses to Administered Cells

In some embodiments, the efficacy of adoptive cell therapy may be limited by the development of an immune response in the subject to the cells and/or construct administered. It is observed herein that even in certain subjects having B cell malignancies, who often are immunocompromised, immune responses can be detected that are specific for regions of receptors expressed by cells administered in adoptive cell therapy. Additionally, in some contexts, loss, downregulation, and/or modification, of a disease-specific or disease-associated antigen being targeted by cell therapy can occur in a subject, which can impair efficacy of therapy targeting that antigen or epitope. For example, CD19-negative disease have been observed in certain subjects having been treated with anti-CD19 immunotherapy. In some embodiments, the provided methods provide offer improved efficacy in one or more of such contexts.

In some embodiments of the provided methods, one or more of the doses or administrations, e.g., the subsequent dose(s) or administration of cells expressing the second receptor, is administered at a time at which an immune response, e.g., an adaptive or specific immune response to the first recombinant receptor and/or cells, in the subject is present, detectable, or detectable above a certain level. The presence or degree of a specific immune response to the recombinant molecule can be related to the immunogenic properties of the receptor, e.g., the CAR or transgenic TCR, expressed by the cells, and/or the time during which the subject has been exposed thereto. For example, in some embodiments, an immune response, e.g., a specific humoral and/or cell-mediated immune response against the receptor, is detected at or about 28 days, at or about 35 days, or at or about 42 days following the first exposure of the subject to the cells expressing the first receptor. Thus, in some embodiments, the subsequent dose of receptor-expressing cells that do not express the receptor expressed by the cells of the first dose, is administered after an immune response, an adaptive or specific immune response, a detectable immune response, and/or a memory response against the first recombinant receptor or cells of the first or prior dose has developed in the subject. In this regard, the ability of cells of the subsequent dose to expand and/or persist in the subject is improved in comparison to other methods in which the cells of the subsequent dose express the same receptor as the first dose. In some embodiments, the second or subsequent dose is administered at a point in time that is at least or is greater than at or about 28 days, 35 days, or 42 days. In some embodiments, it is administered at or about or at least at or about 14 or 21 days.

The methods may involve the detection of the presence or absence or level of such an immune response or indicator thereof, for example, following the administration of a first or second dose and before the administration of the subsequent or next subsequent dose.

In some embodiments, the decision of when and/or whether to administer the subsequent dose depends on whether the subject exhibits such an immune response or detectable readout thereof, e.g., a detectable specific or adaptive host immune response specific for the cells or recombinant receptor, e.g., CAR, expressed by the cells of the first dose, and/or whether such a response is detected above a certain level. In some embodiments, where such a response is detected, the subject is administered the subsequent dose.

In general, the subsequent dose is administered at a time at which the subject exhibits a specific or adaptive, e.g., humoral or cell-mediated, immune response against the receptor, e.g., CAR, expressed by the cells of the first dose, or exhibits such a response or indicator thereof at a detectable level or above an acceptable level. In some aspects, at the time of administration of the subsequent dose, the subject exhibits a humoral or cell-mediated immune response against the receptor, e.g., CAR, expressed by the cells of the first dose.

In some embodiments, the host immune response is or comprises a humoral immune response. The humoral immune response may be indicated by the presence of antibodies specific for the cells or receptors expressed thereby in the serum, other bodily fluid, and/or organ or tissue of the subject. In some embodiments, such antibodies of a particular isotype are present, such as IgM or IgG, e.g., IgG1, IgG2, IgG3, and/or IgG4; in some embodiments they include IgE.

In some embodiments, the immune response is or comprises a cell-mediated component. A cell-mediated response may be indicated by the presence of cells, e.g., T cells, e.g., helper or cytotoxic T cells, that specifically recognize one or more epitopes of the recombinant receptor or cells via a T cell receptor.

In some embodiments the immune response is a primary immune response; in some aspects, the immune response is a memory response.

In some of any of the above embodiments, a detectable immune response refers to an amount detectable by any of a number of known methods for assessing specific immune responses to particular antigens and cells. For example, in some embodiments, the immune response of the specified type is detectable by performing ELISpot, ELISAs, or cell-based antibody detection methods, for example, by flow cytometry, on serum from the subject to detect the presence of antibodies that specifically bind to and/or neutralize antigens present on the cells, e.g., binding to epitopes of the recombinant receptor, e.g., CAR. In some such assays, isotype of the detected antibody is determined and may indicate the type of response and/or whether the response is a memory response.

In some embodiments, the specified immune response is detectable by cytotoxic T-lymphocyte (CTL) assays for detection of CD8+ T cells that specifically bind to and induce cytotoxicity in response to epitopes in the recombinant receptor, and/or a mixed lymphocyte reaction, using cells, e.g., irradiated cells, expressing the recombinant receptor, as stimulator cells.

In some aspects, the detectable immune response is one that is detected by such a method above or significantly above the level of a control sample, such as a non-coated well or well coated with a control peptide or cells not expressing the recombinant receptor and/or levels detected based on pre-treatment serum or blood sample from the subject prior to treatment with the cells expressing the recombinant receptors.

In some aspects, the presence or absence of such a host immune response and/or quantity, degree, or extent thereof, is detected or measured, for example, following the administration of the first dose or subsequent dose(s).

Humoral immune responses may be detected by any of a number of well-known assays for detection of antibodies specific for particular antigens or cells, including binding assays, immunoassays, and including cell-based assays. The assays may include those designed to assess the presence or absence of particular functions of the antibodies, such as their ability to carry out a particular effector function upon binding to the antigen, such as neutralizing antibody assays. In some embodiments, outcomes of humoral immune responses, such as antigen-specific antibodies, e.g., neutralizing antibodies, are detected using cell-based assays, e.g., by incubating pre- and post-treatment cells from the subject with cells expressing the recombinant receptor (and control cells) and detecting antigen-specific binding and/or other outcomes, such as neutralizing outcomes, e.g., by flow cytometry or enzymatic assays. In some embodiments, ELISA, and/or ELISpot assays are used to detect and quantify antibodies specific for the recombinant receptors, such as CARs, and epitopes mapped using known techniques, such as those using individual peptides representing portions of the receptor. See, e.g., Berger et al. *Blood.* 2006 March; 107(6): 2294-2302, Berger et al. *J Virol.* 2001 January 75(2): 799-808, Riddell et al. *Nature Medicine.* 1996 February 2(2): 216-223, Berger et al. *Blood.* 2005 February 105(4): 1640-1647, Jensen et al. *Biol Blood Marrow Transplant.* 2010 September; 16(9): 1245-1256. In some embodiments isotype of the detected antibodies are assessed, for example by using detection antibodies specific for particular isotypes, e.g., human isotypes.

Cellular or cell-based immune response to the cells and/or receptors may be detected and/or measured using any of a number of well-known techniques. Such techniques may include cytotoxic T-lymphocyte (CTL) assays for detection of CD8+ T cells that specifically bind to and induce cytotoxicity in response to epitopes in the recombinant receptor, e.g., CAR, and/or cells administered. In some embodiments, the assay is a mixed lymphocyte reaction, such as those using PBMCs or other host-derived cells from blood or other organ or tissue as responder cells, and cells induced to express the recombinant receptor, e.g., irradiated T cells expressing the CAR, as stimulator cells. The stimulator cells generally are autologous and may be the same cells administered to the subject, and may be irradiated. Non-transduced cells or cells not expressing the transgene of interest may be used as negative controls in place of the stimulator cells in control samples. Likewise, responder cell samples from pre-treated time points or other subjects may be used in control samples. In some aspects, such assays assess the ability of host cells to carry out one or more effector functions, e.g., antigen-specific cell lysis, e.g., using a chromium release assay to detect cytotoxic T cells present in the subject which specifically recognize and antigens present on or in the administered cells and induce a cytotoxic response. In some embodiments, peripheral blood cells, e.g., PBMCs, are obtained from a subject before and after administration of the cells, and each used in an assay, such as a cell lysis assay, using autologous T cells modified to express the recombinant receptor, which generally are irradiated. Specific lysis indicates the presence of receptor-specific cell-mediated immune response. Epitope mapping may be carried out using panels of peptides representing portions of the recombinant receptor. See, e.g., Berger et al. *Blood.* 2006 March; 107(6): 2294-2302, Berger et al. *J Virol.* 2001 January 75(2): 799-808, Riddell et al. *Nature Medicine.* 1996 February 2(2): 216-223, Berger et al. *Blood.* 2005 February 105(4): 1640-1647, Lamers, *Blood* 2011 117: 72-82. HLA tetramer binding assays may be used for the enumeration of antigen-specific T cells. In some aspects, lymphoproliferative assays (LPAs) and/or assays to assess for secreted cytokines, such as ELISAs and/or intracellular staining and assessment by flow cytometry, are used for detection of transgene-specific CD4+ T cells.

In some embodiments, the presence or absence of a specific immune response against the cells or receptor in the subject is assessed, for example, by any of the assays described herein, e.g., epitope mapping. In some aspects, immunogenic epitopes and/or regions within the first receptor, e.g., to which an immune response has developed or is likely to have developed in the subject following the first administration, are determined and a second receptor chosen that does not contain such immunogenic epitopes or regions and/or that contains amino acid differences in such regions.

In some embodiments, the presence or absence of such an immune response after the first or prior administration is detected, and informs which differences are designed to be present in the second or subsequent receptor as compared to the first or prior receptor. Such detection may include identifying at least a region of the first or otherwise prior receptor (e.g., CAR) to which the subject exhibits a specific immune response.

Thus, in some embodiments, the cells of the second dose are selected based on the receptor that they express. In some embodiments, the second dose contains cells expressing a receptor (e.g., CAR) that does not contain a particular immunoreactive epitope for which the subject has developed an immune response following administration of the first or prior dose and/or does not contain any such immunoreactive epitope or any such epitope determined to be immunogenic. In some aspects, a subject may be administered a second or subsequent dose of cells expressing a receptor that is distinct from the receptor expressed by the cells of the first dose in one or more regions determined to be immunogenic. Thus, in some embodiments, the selection of the receptor-expressing cells to be administered in the second (or other subsequent) dose is patient-specific.

In some embodiments, administration of the second dose containing cells that express a receptor, e.g. CAR, that is distinct from the receptor expressed by the cells of the first dose, does not elicit a detectable humoral or cell-mediated immune response specific for the receptor of the first dose. In some aspects, the second dose does not elicit a detectable humoral or cell-mediated immune response against the receptor expressed by the cells of the second dose.

Thus, in some embodiments, the subject does not exhibit an immune response, such as a detectable immune response, e.g., a humoral or cell-mediated immune response, against the second receptor following the administration of the cells expressing the second receptor, or does not exhibit such a response within a certain time period, such as within about 60 days of the administration of those cells.

In some embodiments, the method prevents the induction of or reduces the level of antibodies against the receptor expressed by the cells of the second dose. For example, antibody titers of anti-receptor, e.g. anti-CAR, antibodies, for example, as measured in the serum of the subject by ELISA, are decreased following administration of the subsequent dose, as compared to methods in which a subsequent dose of cells expressing the same receptor as the cells of the first dose is administered. Thus, in some embodiments, the methods improve efficacy by increasing exposure of the subject to the administered cells by preventing or reducing host immune responses that would otherwise clear or prevent expansion of the administered cells.

V. Dosing

The methods generally are designed to improve efficacy of adoptive cell therapy, such as by providing increased exposure of the subject to the cells, e.g., over time. The methods involve administering a first dose, generally followed by a second and/or one or more additional subsequent doses, with particular time frames between certain different doses.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells are administered in a single pharmaceutical composition.

In some embodiments, the cells are administered in a plurality of compositions, collectively containing the cells of a single dose.

The term "split dose" refers to a dose that is split so that it is administered over more than one infusion, e.g., over more than one day. This type of dosing is encompassed by the present methods and is considered to be a single dose. The split dose is infused over a period of no more than three days.

Thus, one or more of the doses in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, multiple doses are given, in some aspects using the same timing guidelines as those with respect to the timing between the first and second doses, e.g., by administering a first and multiple subsequent doses, with each subsequent dose given at a point in time that is greater than about 28 days after the administration of the first or prior dose.

As used herein, "first dose" is used to describe the timing of a given dose being prior to the administration of a subsequent or second dose. The term does not necessarily imply that the subject has never before received a dose of cell therapy or even that the subject has not before received a dose of the same cells or cells expressing the same or different recombinant receptor or targeting the same or different antigen. For example, in some embodiments, the first dose as used herein represents the second or greater infusion of the cells to the subject.

As used herein, "second dose" is used to describe the timing of a given dose being subsequent to the administration of a prior, e.g., first, dose. The term does not necessarily imply that the subject has only before received one dose of cell therapy or that the subject has only before received doses of cells expressing the same recombinant receptor or targeting the same antigen. In some embodiments, multiple doses are administered between the first and second doses, and/or prior to the first or subsequent to the second dose. For example, multiple doses of cells of the first dose (or cells expressing the receptor of the first does) may be administered, followed by multiple doses of the cells or receptor of the second dose. The terms first and second are merely used to describe different doses relative in time to one another.

With reference to a prior dose, such as a first dose, the term "subsequent dose" refers to a dose that is administered to the same subject after the prior, e.g., first, dose. In some aspects, the subsequent dose is the second, third, fourth, and so forth, dose. Neither the term "subsequent" nor a particular numerical value (e.g., "second"), when describing a dose, implies the absence of intervening doses.

In some embodiments, one or more consecutive doses of cells expressing the same receptor, e.g., CAR, as the first dose, may be administered to the subject.

With reference to a prior dose, such as a first dose, the term "consecutive dose" refers to a dose that is administered to the same subject after the prior, e.g., first, dose without any intervening doses having been administered to the subject in the interim. Nonetheless, the term does not encompass the second, third, and/or so forth, injection or infusion in a series of infusions or injections comprised within a single split dose. Thus, unless otherwise specified, a second infusion within a one, two or three-day period is not considered to be a "consecutive" dose as used herein. Likewise, a second, third, and so-forth in the series of multiple doses within a split dose also is not considered to be an "intervening" dose in the context of the meaning of "consecutive" dose. Thus, unless otherwise specified, a dose administered a certain period of time, greater than three days, after the initiation of a first or prior dose, is considered to be a "consecutive" dose even if the subject received a second or subsequent injection or infusion of the cells following the initiation of the first dose, so long as the second or subsequent injection or infusion occurred within the three-day period following the initiation of the first or prior dose.

Thus, unless otherwise specified, multiple administrations of the same cells over a period of up to 3 days is considered to be a single dose, and administration of cells within 3 days of an initial administration is not considered a consecutive dose and is not considered to be an intervening dose for purposes of determining whether a second dose is "consecutive" to the first.

In some embodiments, multiple consecutive doses are given. The multiple consecutive doses may be administered, for example, using the same timing guidelines as those specified for the timing between a first and first consecutive dose, such as by administering a first and multiple consecutive doses, with each consecutive dose given within a period of time that is greater than about 14 and less than about 28 days, e.g., about 21 days, after the administration of the first or immediately prior dose. In some embodiments, with respect to the first dose, the consecutive doses each include the same cells as those administered in the first dose, and/or the same recombinant receptor expressed by those in the first dose. In some such embodiments, administration of such consecutive dose(s) is followed by administration of a second dose, and in some cases additional consecutive dose(s).

Thus, in some aspects, the subject may be administered multiple doses of cells expressing the same receptor. In some embodiments, multiple consecutive doses containing cells expressing a first receptor may be administered to the subject prior to the subsequent administration of cells expressing a distinct receptor, such as prior to the administration of the second dose, which may in some embodiments also be followed by a consecutive administration of cells of the second dose. In some aspects, the multiple consecutive doses of cells expressing the second (or third, fourth, fifth, and so forth) receptor may be administered to the subject.

In some embodiments, for example, in the context of multiple clinical trials, a subject may be administered a first dose of cells expressing a receptor being investigated in a first clinical trial and a second (or other subsequent) dose of cells expressing a receptor being investigated in a second clinical trial.

In some embodiments, the provided methods are for long-term or continuous treatment or management of the disease or disorder in the subject, involving first, second, third, and/or multiple additional subsequent administrations of engineered cells, each expressing distinct recombinant receptors targeting the same disease or condition in the subject. Such long-term treatment or management may involve an iterative process, in which the subject is monitored and a next subsequent administration (e.g., next subsequent receptor) is introduced if and when a particular indicator of loss of efficacy or risk thereof is detected. In some embodiments, each subsequent administration is initiated upon detection of one or more indicators of a risk of loss of efficacy, such as reduced persistence of, expansion of, or exposure to the cells in the prior dose, an immune response specific thereto in the subject, relapse, resistance, and/or downregulation or change in the target antigen.

In some embodiments, the subsequent dose is administered for retreatment upon relapse, and/or to prevent recurrence of the targeted disease or disorder, and/or to address or prevent a reduction in exposure to cells expressing the recombinant receptors following a first dose, for example, upon detection of a decline in persistence or expansion of such cells or in numbers of such cells. Thus, in some embodiments one or more of these parameters is measured, detected, or assessed in the time between the first or other prior dose and the second or other subsequent dose, and the timing or decision to administer the subsequent dose is made based on the outcome of such assessment. For example, the second dose may be administered at a time at which it is determined that the number or concentration of the receptor-expressing cells is below a desired level or has declined below a certain percentage of maximum or other measured concentration or number.

Dosage Amount or Size

In some embodiments, the first or subsequent dose contains a number of cells, number of recombinant receptor (e.g., CAR)-expressing cells, number of T cells, or number of peripheral blood mononuclear cells (PBMCs) in the range from about $10^5$ to about $10^6$ of such cells per kilogram body weight of the subject, and/or a number of such cells that is no more than about $10^5$ or about $10^6$ such cells per kilogram body weight of the subject. For example, in some embodiments, the first or subsequent dose includes less than or no more than at or about $1\times10^5$, at or about $2\times10^5$, at or about $5\times10^5$, or at or about $1\times10^6$ of such cells per kilogram body weight of the subject. In some embodiments, the first dose includes at or about $1\times10^5$, at or about $2\times10^5$, at or about $5\times10^5$, or at or about $1\times10^6$ of such cells per kilogram body weight of the subject, or a value within the range between any two of the foregoing values. In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some embodiments, for example, where the subject is a human, the first or subsequent dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some embodiments, the first or subsequent dose contains fewer than about $1\times10^8$ total recombinant receptor (e.g., CAR)-expressing cells, T cells, or peripheral blood mononuclear cells (PBMCs) cells per $m^2$ of the subject, e.g., in the range of about $1\times10^6$ to $1\times10^8$ such cells per $m^2$ of the subject, such as $2\times10^6$, $5\times10^6$, $1\times10^7$, $5\times10^7$, or $1\times10^8$ such cells per $m^2$ of the subject, or the range between any two of the foregoing values.

In certain embodiments, the number of cells, recombinant receptor (e.g., CAR)-expressing cells, T cells, or peripheral blood mononuclear cells (PBMCs) in the first or subsequent dose is greater than about $1\times10^6$ such cells per kilogram body weight of the subject, e.g., $2\times10^6$, $3\times10^6$, $5\times10^6$, $1\times10^7$, $5\times10^7$, $1\times10^8$, $1\times10^9$, or $1\times10^{10}$ such cells per kilogram of body weight and/or, $1\times10^8$, or $1\times10^9$, $1\times10^{10}$ such cells per $m^2$ of the subject or total, or the range between any two of the foregoing values.

In some embodiments, the number of cells administered in the subsequent dose is the same as or similar to the number of cells administered in the first dose in any of the embodiments herein, such as less than or no more than at or about $1\times10^5$, at or about $2\times10^5$, at or about $5\times10^5$, or at or about $1\times10^6$ of such cells per kilogram body weight of the subject. In some embodiments, the subsequent dose(s) contains at or about $1\times10^5$, at or about $2\times10^5$, at or about $5\times10^5$, or at or about $1\times10^6$ of such cells per kilogram body weight of the subject, or a value within the range between any two of the foregoing values. In some embodiments, such values refer to numbers of recombinant receptor-expressing cells; in other embodiments, they refer to number of T cells or PBMCs or total cells administered. In some aspects, the subsequent dose is larger than the first dose. For example, in some embodiments, the subsequent dose contains more than about $1\times10^6$ cells, recombinant receptor (e.g. CAR)-expressing cells, T cells, and/or PBMCs per kilogram body weight of the subject, such as about $3\times10^6$, $5\times10^6$, $1\times10^7$, $1\times10^8$, or $1\times10^9$ such cells per kilogram body weight of the subject. In some embodiments, the amount or size of the subsequent dose is sufficient to reduce disease burden or an indicator thereof, and/or one or more symptoms of the disease or condition. In some embodiments, the second (or other subsequent) dose is of a size effective to improve survival of the subject, for example, to induce survival, relapse-free survival, or event-free survival of the subject for at least 6 months, or at least 1, 2, 3, 4, or 5 years. In some embodiments, the number of cells, recombinant receptor (e.g. CAR)-expressing cells, T cells, and/or PBMCs administered and/or number of such cells administered per body weight of the subject in the subsequent dose is at least 2-fold, 5-fold, 10-fold, 50-fold, or 100-fold or more greater than the number administered in the first dose. In some embodiments, disease burden, tumor size, tumor volume, tumor mass, and/or tumor load or bulk is reduced following the subsequent dose by at least at or about 50, 60, 70, 80, 90% or more compared to that immediately prior to the administration of the first dose or of the second (or other subsequent) dose.

In other embodiments, the number of cells administered in the subsequent dose is lower than the number of cells administered in the first dose.

In some embodiments, multiple subsequent doses are administered following the first dose, such that an additional dose or doses are administered following administration of the second (or other subsequent) dose. In some aspects, the number of cells administered to the subject in the additional subsequent dose or doses (i.e., the third, fourth, fifth, and so forth) is the same as or similar to the first dose, the second dose, and/or other subsequent dose. In some embodiments, the additional dose or doses are larger than prior doses.

In some aspects, the size of the first and/or subsequent dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the first and/or subsequent dose is determined by the burden of the disease or condition in the subject. For example, in some aspects, the number of cells administered in the first dose is determined based on the tumor burden that is present in the subject immediately prior to administration of the first dose. In some embodiments, the size of the first and/or subsequent dose is inversely correlated with disease burden. In some aspects, as in the context of a large disease burden, the subject is administered a low number of cells, for example less than about $1\times10^6$ cells per kilogram of body weight of the subject. In other embodiments, as in the context of a lower disease burden, the subject is administered a larger number of cells, such as more than about $1\times10^6$ cells per kilogram body weight of the subject.

In some aspects, the number of cells administered in the subsequent dose is determined based on the tumor burden that is present in the subject following administration of the first dose. In some embodiments, e.g. where the first dose has decreased disease burden or has done so below a particular threshold amount or level, e.g., one above which there is an increased risk of toxic outcome, the subsequent dose is large, e.g. more than $1 \times 10^6$ cells (e.g., total cells, receptor-expressing cells, T cells, or PBMCs) per kilogram body weight, and/or is larger than the first dose. In other aspects, the number of cells administered in the subsequent dose is low, e.g. less than about $1 \times 10^6$, e.g. the same as or lower than the first dose, where the first dose has reduced tumor burden to a small extent or where the first dose has not led to a detectable reduction in tumor burden.

In some embodiments, the number of cells administered in the first dose is lower than the number of cells administered in other methods, such as those in which a large single dose of cells is administered, such as to administer the cells in before an immune response develops. Thus, in some embodiments, the methods reduce toxicity or toxic outcomes as compared to other methods that involve administration of a larger dose.

In some embodiments, the first dose includes the cells in an amount that does not cause or reduces the likelihood of toxicity or toxic outcomes, such as cytokine release syndrome (CRS), severe CRS (sCRS), macrophage activation syndrome, tumor lysis syndrome, fever of at least at or about 38 degrees Celsius for three or more days and a plasma level of CRP of at least at or about 20 mg/dL, and/or neurotoxicity. In some aspects, the number of cells administered in the first dose is determined based on the likelihood that the subject will exhibit toxicity or toxic outcomes, such as CRS, sCRS, and/or CRS-related outcomes following administration of the cells. For example, in some embodiments, the likelihood for the development of toxic outcomes in a subject is predicted based on tumor burden. In some embodiments, the methods include detecting or assessing the toxic outcome and/or disease burden prior to the administration of the dose.

In some embodiments, the second (or other subsequent) dose is administered at a time point at which a clinical risk for developing cytokine-release syndrome (CRS), macrophage activation syndrome, or tumor lysis syndrome, or neurotoxicity is not present or has passed or has subsided following the first administration, such as after a critical window after which such events generally have subsided and/or are less likely to occur, e.g., in 60, 70, 80, 90, or 95% of subjects with a particular disease or condition.

Timing of Doses

In some aspects, the timing of the second or subsequent dose is measured from the initiation of the first dose to the initiation of the subsequent dose. In other embodiments, the timing of the subsequent dose is measured from the completion of the first dose, or from the median day of administration of the first dose, e.g. in the context of split dosing, described herein, where a dose is administered over more than one day, e.g. over 2 days or over 3 days.

In some embodiments, whether a subsequent dose of cells expressing a receptor, e.g. CAR, that is distinct from that expressed by the cells of the first dose is administered, is determined based on the presence or degree of an immune response or detectable immune response in the subject to the cells of the first dose or recombinant receptor expressed thereby. In some aspects, a subsequent dose containing cells expressing a different receptor than the cells of the first dose will be administered to a subject with a detectable host adaptive immune response, or an immune response that has become established or reached a certain level, stage, or degree.

In some embodiments, the second (or other subsequent) dose is administered at a point in time at which a second administration of cells expressing the first receptor (e.g., CAR) is likely to be or is predicted to be eliminated by the host immune system. The likeliness of developing an immune response may be determined by measuring receptor-specific immune responses in the subject following administration of the first dose, as described herein.

For example, in some embodiments, subjects may be tested following the first (or other prior) dose and prior to the second (or other subsequent) dose to determine whether an immune response is detectable in the subject after the first dose. In some such embodiments, the detection of an immune response to the first dose may trigger the need to administer the second dose.

In some aspects, samples from the subjects may be tested as described herein to determine if there is a decline in or lower than desired exposure, for example, less than a certain number or concentration of cells, as described herein, in the subject after the first or prior dose. In some such aspects, the detection of a decline in the exposure of the subject to the cells may trigger the need to administer the second dose.

In some embodiments, the subsequent dose is administered at a point in time at which the disease or condition in the subject has not relapsed following the reduction in disease burden in response to the first or prior dose. In some embodiments, the disease burden reduction is indicated by a reduction in one or more factors, such as load or number of disease cells in the subject or fluid or organ or tissue thereof, the mass or volume of a tumor, or the degree or extent of metastases. Such a factor is deemed to have relapsed if after reduction in the factor in response to an initial treatment or administration, the factor subsequently increases.

In some embodiments, the second dose is administered at a point in time at which the disease has relapsed. In some embodiments, the relapse is in one or one or more factors, or in the disease burden generally. In some aspects, the subsequent dose is administered at a point in time at which the subject, disease burden, or factor thereof has relapsed as compared to the lowest point measured or reached following the first or prior administration, but still is lower compared to the time immediately prior to the first dose. In some embodiments, the subject is administered the subsequent dose at a point in time at which disease burden or factor indicative thereof has not changed, e.g. at a time when an increase in disease burden has been prevented.

In some embodiments, the subsequent dose is administered at a time when a host adaptive immune response is detected, has become established, or has reached a certain level, degree, or stage. In some aspects, the subsequent dose is administered following the development of a memory immune response in the subject.

In some aspects, the time between the administration of the first dose and the administration of the subsequent dose is about 28 to about 35 days, about 29 to about 35 days, or more than about 35 days. In some embodiments, the administration of the second dose is at a time point more than about 28 days after the administration of the first dose. In some aspects, the time between the first and subsequent dose is about 28 days.

In some embodiments, an additional dose or doses, e.g. subsequent doses, are administered following administration of the second dose. In some aspects, the additional dose or doses are administered at least about 28 days following administration of a prior dose. In some embodiments, no dose is administered less than about 28 days following the prior dose.

In some aspects, the present methods are advantageous in that they allow administration of receptor-expressing cells at time points that extend beyond the time range that other methods may administer a second dose containing cells that express the receptor of the first dose, e.g., after an immune response to the cells of the first dose is detected.

In some embodiments, the methods reduce toxicity or toxic outcomes as compared to other methods, for example, by allowing the second administration to occur after toxic outcomes following the first dose have cleared, e.g., which may be at a point in time at which a second administration of cells expressing the first receptor would be cleared by an immune response to the first receptor.

In some aspects, the methods allow for administration of a second dose at a point in time at which a relapse has occurred, for example, when the subject has initially responded to treatment but develops relapse, for example, at a point in time at which a second administration of cells expressing the first receptor would be cleared by an immune response to the first receptor.

In some embodiments, e.g. where one or more consecutive doses expressing the receptor expressed by the cells of the first dose are administered to the subject, the consecutive doses may be separated by about 14, about 15, about 21, about 27, or about 28 days. In some aspects, the consecutive dose is administered 21 days following a prior dose. In some embodiments, the consecutive dose is administered between 14 and 28 days following administration of a prior dose.

In any of the embodiments, the methods in some cases include the administration of the first or prior dose and the subsequent dose(s), and in other cases include the administration of the subsequent dose(s) to a subject who has previously received the first or prior dose but do not include the administration of the first or prior dose itself. Thus, the methods in some cases involve the administration of consolidating treatment, such as by administering a consolidating subsequent dose to a subject that has previously received a dose of recombinant receptor-expressing, e.g., CAR-expressing, cells.

In some embodiments, disease burden, tumor size, tumor volume, tumor mass, and/or tumor load or bulk is reduced following the subsequent dose by at least at or about 50, 60, 70, 80, 90% or more compared to that immediately prior to the administration of the first or prior dose or of the second or subsequent dose.

VI. Cell Exposure and Persistence

In some embodiments, the provided methods increase exposure of the subject to the administered cells (e.g., increased number of cells or duration over time) and/or improve efficacy and therapeutic outcomes in adoptive cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the presence and/or amount of cells expressing the recombinant receptor (e.g., CAR-expressing cells) in the subject following the first dose and/or following the subsequent dose is detected. In some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the second (or other subsequent) dose. In some aspects, the cells are detected at or at least at 2, 4, or 6 weeks following, or 3, 6, or 12, 18, or 24, or 30 or 36 months, or 1, 2, 3, 4, 5, or more years, following administration of the second (or other subsequent) dose.

In some embodiments, the persistence of receptor, e.g., CAR, -expressing cells in the subject by the methods, following administration of the subsequent dose, is greater as compared to that which would be achieved by alternative methods such as those involving the administration of a single dose or administration of a subsequent dose of cells expressing the same receptor, e.g. CAR, as the cells of the first (or other prior) dose.

In some embodiments, the persistence and/or expansion and/or presence of recombinant receptor-expressing, e.g., CAR-expressing, cells in the subject following administration of the second dose is greater as compared to that achieved via a method using an alternative dosing regimen, such as one involving the administration of a single dose of receptor-expressing cells or one involving a second dose or multiple doses of cells expressing the same receptor as expressed by the cells of the first dose.

The exposure, e.g., number of cells, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood or serum, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor-(e.g., CAR-)expressing cells expand in the subject following administration of the first dose and/or following administration of the subsequent dose. In some aspects, the methods result in greater expansion of the cells compared with other methods, such as those involving the administration a single dose of cells or a subsequent dose or doses of cells expressing the same receptor as the first dose.

In some aspects, the method results in high in vivo proliferation of the administered cells, for example, as measured by flow cytometry. In some aspects, high peak proportions of the cells are detected. For example, in some embodiments, at a peak or maximum level following the first or subsequent administration, in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR per microgram of DNA, or at least 0.1, 0.2, 0.3, 0.4, 0.5, 0.6, 0.7, 0.8, or 0.9 receptor-expressing, e.g., CAR-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the first or subsequent administration or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum of the subject.

In some embodiments, cells expressing the receptor are detectable in the blood or serum of the subject, e.g., by a specified method, such as qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the first dose or after administration of the second (or other subsequent) dose, or for at least at or about 2, 3, 4, 5, 6, 7, 8, 9, 10, 11, 12, 13, 14, 15, 16, 17, 18, 19, 20, 21, 22, 23, or 24 or more weeks following the administration of the first dose or subsequent dose(s).

In some aspects, at least about $1\times10^2$, at least about $1\times10^3$, at least about $1\times10^4$, at least about $1\times10^5$, or at least about $1\times10^6$ or at least about $5\times10^6$ or at least about $1\times10^7$ or at least about $5\times10^7$ or at least about $1\times10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, tissue, or compartment thereof, such as in the blood, e.g., peripheral blood, or disease site thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the first dose or following the administration of the subsequent dose(s). Such cell numbers may be as detected by flow cytometry-based or quantitative PCR-based methods and extrapolation to total cell numbers using known methods. See, e.g., Brentjens et al., *Sci Transl Med.* 2013 5(177), Park et al, Molecular Therapy 15(4):825-833 (2007), Savoldo et al., *JCI* 121(5):1822-1826 (2011), Davila et al. (2013) *PLoS ONE* 8(4):e61338, Davila et al., *Oncoimmunology* 1(9):1577-1583 (2012), Lamers, *Blood* 2011 117:72-82, Jensen et al. *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8. 9, 10, 11, or 12 months or at least 2 or 3 years following administration of the cells, e.g., the first or subsequent dose(s). In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the first dose or subsequent dose(s) of receptor-expressing, e.g. CAR-expressing, cells, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, blood thereof, and/or disease site thereof, at a time that is at least about 3 months, at least about 6 months, at least about 12 months, at least about 1 year, at least about 2 years, at least about 3 years, or more than 3 years, following the administration of the cells, e.g., following the initiation of the administration of the first dose or the second or subsequent dose.

In some embodiments, the area under the curve (AUC) for concentration of receptor-(e.g., CAR-)expressing cells in a fluid, tissue, or organ, e.g., blood, of the subject over time following the administration of the first dose is greater as compared to that achieved via an alternative dosing regimen where the subject is administered a single dose of cells or multiple doses of cells expressing the same receptor.

In some aspects, the area under the curve (AUC) for concentration of receptor-(e.g., CAR-)expressing cells in a fluid, tissue, or organ, e.g., blood, of the subject over time over time following the administration of the subsequent dose is greater as compared to that achieved via an alternative dosing regimen where the subject is administered a single dose of cells or multiple doses of cells expressing the same receptor.

VII. Disease Burden

The administration of the doses generally reduces or prevents the expansion or burden of the disease or condition in the subject. For example, where the disease or condition is a tumor, the methods generally reduce tumor size, bulk, or metastasis, and/or improve prognosis or survival or other symptom associated with tumor burden. In some embodiments, administration of the second or subsequent dose is timed with respect to the development of a transgene-specific immune response and/or relapse following the first or prior dose.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor and/or the number or extent of metastases.

In some embodiments, the administration of the two or more doses effects a reduction in disease burden. In some aspects, administration of the doses may prevent an increase in disease burden, and this may be evidenced by no change in disease burden.

In some aspects, the disease or condition persists following administration of the first dose and/or administration of the first dose is not sufficient to eradicate the disease or condition in the subject.

In some aspects, administration of the second dose reduces disease burden as compared to disease burden at a time immediately prior to the first dose, or at a time immediately prior to the second dose. In some aspects, for example in the context of relapse, administration of the second dose effects a reduction in disease burden as compared to the peak level of disease burden following administration of the first dose.

In some embodiments, the method reduces the burden of the disease or condition, e.g., number of tumor cells, size of tumor, duration of patient survival or event-free survival, to a greater degree and/or for a greater period of time as compared to the reduction that would be observed with a method using an alternative dosing regimen, such as one in which the subject receives a single dose of cells or multiple doses of cells expressing the same receptor, e.g., CAR. In some embodiments, disease burden is reduced to a greater extent or for a greater duration following the second dose compared to the reduction that would be effected by administering a second dose of cells expressing the same receptor, e.g., CAR.

In some embodiments, the burden of disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some aspects, disease burden is measured or detected prior to administration of the first dose, following the administration of the first dose but prior to administration of the second dose, and/or following administration of the second or subsequent dose. In the context of multiple subsequent doses, disease burden in some embodiments may be measured prior to or following any of the subsequent doses, or at a time between administration of subsequent doses.

In some aspects, administration of the doses effects a reduction in disease burden, e.g. tumor burden, such as a at or about 10, 20, 30, 40, 50, 60, 70, 90, or 100 percent decrease in burden compared to immediately prior to the administration of the second dose or overall compared to immediately prior to the first dose. In some embodiments, disease burden, tumor size, tumor volume, tumor mass, and/or tumor load or bulk is reduced following the second dose by at least at or about 50, 60, 70, 80, 90% or more compared to that immediately prior to the administration of the first dose or of the subsequent dose.

In some embodiments, reduction of disease burden by the method comprises an induction in morphologic complete remission, for example, as assessed at 1 month, 2 months, 3 months, or more than 3 months, after administration of, e.g., initiation of, the first or any subsequent dose. In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the first dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the first dose is less than about 80%, less than about 70%, less than about 60%, less than about 50%, less than about 40%, less than about 30%, less than about 20%, or less than about 10%.

VIII. Toxicity and Toxic Outcomes

In some embodiments, the methods reduce or prevent toxicity or an outcome or symptom thereof, for example, compared to administration of cells as a single dose, administration of a subsequent dose of cells that express the same receptor as the first dose, and/or administration of the subsequent dose at a time which is earlier than the time between the first and subsequent doses specified by the method.

Administration of adoptive T cell therapy, such as treatment with T cells expressing chimeric antigen receptors, can induce toxic effects or outcomes such as cytokine release syndrome and neurotoxicity. In some examples, such effects or outcomes parallel high levels of circulating cytokines, which may underlie the observed toxicity.

In some aspects, the present methods may reduce toxicity or toxic outcomes as compared to other methods by allowing administration of a smaller first dose than other methods, for example, where a single large dose is administered, for example, where multiple smaller doses of cells expressing the same receptor may be eliminated by a host immune response.

In some embodiments, the present methods may reduce toxicity or toxic outcomes as compared to other methods by allowing administration of a subsequent dose more than 28 days after the administration of the first dose, for example, at a time point at which an immune response to the first receptor has developed such that cells expressing the first receptor would be eliminated if administered again. Thus, in some aspects, the methods reduce toxicity as compared to methods that administer multiple doses at a point in time at which the subject is at risk for developing CRS.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

CRS may be treated using anti-inflammatory therapy such as an anti-IL-6 therapy, e.g., anti-IL-6 antibody, e.g., tocilizumab, or antibiotics. In some embodiments, the subject is treated with such a therapy following the first administration and the subsequent dose is administered only if and when the CRS-associated symptom(s) are reduced or declining or declined below an acceptable level following such treatment.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

The method of measuring or detecting the various outcomes may be specified.

In some aspects, prior to the administration of the first dose, subsequent to the administration of the first dose and before administration of the subsequent dose, or following the administration of the subsequent dose, a CRS-associated outcome is assessed in the subject. In some embodiments, the level of the toxic outcome, e.g. the CRS-related outcome, e.g. the serum level of an indicator of CRS, is measured by ELISA.

In some aspects, the toxic outcome is or is associated with neurotoxicity. In some embodiments, the methods reduce symptoms associated with neurotoxicity compared to other methods. For example, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, subjects administered doses according to the methods have reduced symptoms, outcomes, or factors associated with neurotoxicity compared to administration of a single dose, administration of a subsequent dose of cells that expresses the same receptor, e.g., CAR, as the first dose, and/or administration of the subsequent dose at a time which is earlier than the time between the first and subsequent doses specified by the method.

IX. Cells

The cells generally are eukaryotic cells, such as mammalian cells, and typically are human cells, e.g., those derived from human subjects and engineered, for example, to express the recombinant receptors. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Vectors and Methods for Genetic Engineering

Also provided are methods, compositions, and kits, for producing the genetically engineered cells expressing recombinant receptors. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Preparation of Cells for Engineering

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some aspects, the cells of the second dose are derived from the same apheresis product as the cells of the first dose. In some embodiments, the cells of multiple doses, e.g., first, second, third, and so forth, are derived from the same apheresis product.

In other embodiments, the cells of the second (or other subsequent) dose are derived from an apheresis product that is distinct from that from which the cells of the first (or other prior) dose are derived.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

X. Compositions and Formulations

Also provided are compositions including the cells, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

XI. Articles of Manufacture

Also provided are articles of manufacture, such as kits and devices, for the administration of the cells to subjects in according to the provided methods for adoptive cell therapy, and for storage and administration of the cells and compositions.

The articles of manufacture include one or more containers, typically a plurality of containers, packaging material, and a label or package insert on or associated with the container or containers and/or packaging, generally including instructions for administration of the cells to a subject.

The containers generally contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or subsequent dose(s). It may be the lowest dose or lowest possible dose of the cells that would be administered to the subject in connection with the administration method. In some embodiments, the unit dose is the minimum number of cells or number of cells that would be administered in a single dose to any subject having a particular disease or condition or any subject, according to the methods herein. For example, the unit dose in some aspects may include a minimum number of cells that would be administered to a patient of a relatively lower body weight and/or with relatively high disease burden, such that in some cases more than one unit dose is administered to a given subject as a first dose and one or more than one unit dose is administered to a given subject in one or more subsequent dose, e.g., according to the provided methods. In some embodiments, the number of cells in the unit dose is the number of cells or number of recombinant receptor-expressing or CAR-expressing cells that it is desired to administer to a particular subject in a first dose, such as a subject from which the cells have been derived. In some embodiments, the cells have been derived from the subject to be treated by methods as provided herein or in need thereof.

In some embodiments, one or more of the unit doses contains cells that express the same receptor, e.g., CAR. In some aspects, one or more of the unit doses contains cells that express a different receptor, e.g., CAR, than one or more of the other unit doses.

In some embodiments, each of the containers individually comprises a unit dose of the cells that express the first, or second, or third, and so forth, receptor, that contains the same or substantially the same number of cells. Thus in some embodiments, each of the containers comprises the same or approximately or substantially the same number of cells or number of recombinant receptor-expressing cells. In some embodiments, the unit dose includes less than about $1 \times 10^8$, less than about $5 \times 10^7$, less than about $1 \times 10^6$ or less than about $5 \times 10^5$ of the engineered cells, of total cells, of T cells, or PBMCs, per kg of the subject to be treated and/or from which the cells have been derived. In some embodiments, each unit dose contains at or about $2 \times 10^6$, $5 \times 10^6$, $1 \times 10^7$, $5 \times 10^7$, or $1 \times 10^8$ engineered cells, total cells, T cells, or PBMCs.

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 ml capacity, such as between at or about 10 and at or about 100 or between at or about 10 and at or about 500 mL capacity. In some embodiments, the containers, e.g., bags, are and/or are made from material which is stable and/or provide stable storage and/or maintenance of cells at one or more of various temperatures, such as in cold temperatures, e.g. below at or about or at or about −20° C., −80° C., −120° C., 135° C. and/or temperatures suitable for cryopreservation, and/or other temperatures, such as temperatures suitable for thawing the cells and body temperature such as at or about 37° C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more subsequent doses of the cells, e.g., according to any of the embodiments of the provided methods. In some embodiments, the instructions specify administration, in a first dose, of one unit dose, e.g., the contents of a single individual container in the article of manufacture, followed by one or more subsequent doses at a specified time point or within a specified time window and/or after the detection of the presence or absence or amount or degree of one or more factors or outcomes in the subject.

In some embodiments, the instructions specify administering a plurality of the unit doses to the subject by carrying out a first administration and a subsequent administration. In some embodiments, the first administration comprises delivering one of said unit doses containing cells expressing a first receptor, e.g., CAR, to the subject and the subsequent administration comprises administering one or a plurality of said unit doses containing cells expressing the same receptor, e.g. CAR, as the first administration to the subject.

In some aspects, the first administration comprises delivering one of said unit doses containing cells expressing a first receptor, e.g., CAR, to the subject and the subsequent administration comprises administering one or a plurality of said unit doses containing cells expressing a distinct receptor, e.g. CAR, to the subject. In some embodiments, whether the patient receives a second administration that contains cells expressing the same receptor as the first administration or receives a second administration that contains cells expressing a receptor, e.g., CAR, that is distinct from that expressed by the cells of the first administration, may be determined based on any of the parameters of the methods described herein. For example, in some aspects, e.g., where the patient has developed an immune response to the first receptor, a unit dose containing cells that express a receptor that is distinct from the first receptor may be administered.

In some embodiments, the instructions specify that the second (or other subsequent) administration is to be carried out at a time at least about 28 or at least about 35 days following the first administration, e.g., following the initiation of the first administration or the prior administration. In some embodiments, the instructions specify that the subsequent dose is to be administered at a time after which it has been determined that the subject exhibits a detectable adaptive host immune response specific for the receptor, e.g., CAR, expressed by the cells of the first (or other prior) dose.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

XII. Exemplary Embodiments

Among the provided embodiments are:
1. A method of treatment, comprising:
   (a) administering to a subject cells expressing a first chimeric antigen receptor (CAR) that specifically binds to an antigen associated with a disease or condition in the subject; and
   (b) administering to the subject cells expressing a second CAR, which is distinct from said first CAR, and not expressing the first CAR.
2. The method of embodiment 1, wherein, at the time of or immediately prior to the administration of cells expressing the second CAR:

the subject exhibits a detectable humoral and/or cell-mediated immune response specific for the first CAR;
the disease or condition persists in the subject; and/or
the disease or condition has relapsed in the subject.

3. The method of embodiment 1 or embodiment 2, wherein:
the time between the administration of cells expressing the first CAR and the administration of cells expressing the second CAR is at least about 28 days, at least about 35 days, at least about 42 days, at least about 49 days, and/or at least about 60 days.

4. The method of any of embodiments 1-3, wherein said first CAR comprises at least one immunoreactive epitope that is not present in said second CAR.

5. The method of embodiment 4, wherein:
said at least one immunoreactive epitope comprises at least one B cell epitope; and/or
said at least one immunoreactive epitope comprises at least one T cell epitope.

6. The method of any of embodiments 1-5, wherein:
said subject has not received a dose of cells expressing the first CAR prior to said administration in (a); and/or
said subject has not received a dose of cells expressing the second CAR prior to the administration in (b).

7. The method of any of embodiments 1-6, wherein the second CAR specifically binds to the same antigen as the first CAR.

8. The method of any of embodiments 1-7, wherein the disease or condition is a tumor.

9. The method of any of embodiments 1-8, wherein the disease or condition is a B cell malignancy.

10. The method of embodiment 9, wherein the first CAR and the second CAR specifically bind to the same epitope of said antigen.

11. The method of any of embodiments 7-10, wherein the first CAR competes for binding to said antigen with the second CAR.

12. The method of any of embodiments 7-9 and 11, wherein the first CAR and the second CAR specifically bind to distinct epitopes of said antigen.

13. The method of any of embodiments 1-12, wherein:
the second CAR specifically binds to another antigen associated with said disease or condition compared to the antigen bound by the first CAR; or
the second CAR does not specifically bind to the antigen specifically bound by the first CAR.

14. The method of any of embodiments 9-13, wherein the first CAR specifically binds to an antigen associated with a B cell malignancy that is selected from CD19, CD22 or CD20 and the second CAR binds to another antigen from among CD19, CD22 or CD20 that is distinct from the antigen bound by the first CAR.

15. The method of embodiment 14, wherein the first CAR specifically binds to CD19 and the second CAR specifically binds to CD22.

16. The method of any of embodiments 1-6, wherein the cells expressing the second CAR do not comprise a receptor that specifically binds to said antigen specifically bound by the first CAR.

17. The method of any of embodiments 1-16, wherein the subject does not exhibit a detectable humoral or cell-mediated immune response against the second CAR within about 30 days, within about 60 days, or within about 90 days, of the administration of cells expressing the second CAR.

18. The method of any of embodiments 1-17, wherein the second CAR comprises one or more differences in amino acid sequence compared to the first CAR.

19. The method of embodiment 18, wherein
the one or more differences comprise at least one amino acid sequence difference compared to a region of the first CAR to which a detectable immune response is generated in the subject following the administration of cells expressing the first CAR; and/or
the one or more differences comprise at least one amino acid sequence difference compared to each region of the first CAR to which a detectable immune response is generated in the subject following the administration of cells expressing the first CAR.

20. The method of any of embodiments 1-19, further comprising, prior to the administration of cells expressing the second CAR, detecting the presence of a CAR-specific immune response in the subject.

21. The method of embodiment 20, wherein the detection comprises identifying at least a region of the first CAR to which the subject exhibits a specific immune response.

22. The method of embodiment 21, wherein the second CAR contains one or more amino acid sequence differences compared to said region of the first CAR for which the immune response is specific.

23. The method of any of embodiments 19-22, wherein the region of the first CAR comprises a region within one or more CAR portions selected from the group consisting of an scFv portion, a linker portion, an amino acid sequence not endogenous to the subject, a sequence derived from a different species than that of the subject, and/or a junction between two CAR domains; and/or where the region of the first CAR is a junction region comprising amino acids on each side of a junction between two domains.

24. The method of embodiment 23, wherein:
the region comprises a framework region (FR) within the scFv portion,
the region comprises a heavy chain FR sequence
the region comprises a heavy chain CDR sequence,
the region comprises a light chain FR sequence, and/or
the region comprises a light chain CDR sequence.

25. The method of embodiment 24, wherein the region comprises a junction region, wherein the junction region comprises up to 15 contiguous amino acids directly C-terminal of a junction that joins a first domain and a second domain of the first CAR and/or up to 15 contiguous amino acids directly N-terminal of the junction, and optionally further comprises the junction.

26. The method of embodiment 25, wherein:
the first domain and/or second domain comprise a domain of a natural or endogenous human protein or a domain having 100% identity with a domain or functional portion thereof of a natural or endogenous human protein, wherein the natural or endogenous human protein optionally is expressed by the subject to be treated; and/or
the first domain and/or second domain comprises an extracellular binding domain, a hinge domain, a transmembrane domain, or an intracellular signaling domain, which intracellular signaling domain is, optionally, a costimulatory signaling domain or an activating cytoplasmic signaling domain.

27. The method of embodiment 26, wherein the first domain and second domain are not present in the same molecule in vivo in a human subject, or are not present in a single natural or endogenous human protein or polypeptide.

28. The method of embodiment 26 or embodiment 27, wherein the first domain and second domain are or comprise, respectively, an extracellular ligand binding domain and a hinge domain, a hinge domain and a transmembrane domain, a transmembrane domain and an intracellular costimulatory signaling domain, and an intracellular costimulatory signaling domain and an activating cytoplasmic signaling domain, which can include functional portions of such domains.

29. The method of any of embodiments 26-28, wherein the first domain is or comprises a transmembrane domain or a functional portion thereof and the second domain is or comprises a costimulatory signaling domain or a functional portion thereof.

30. The method of embodiment 29, wherein the transmembrane domain is a CD28 transmembrane domain or a functional portion thereof and the costimulatory signaling domain is a 4-1BB signaling domain or a functional portion thereof.

31. The method of any of embodiments 26-30, wherein the second CAR comprises:
a domain of at least 95% sequence identity to the first domain and/or a domain of at least 95% sequence identity to the second domain;
a domain identical in sequence to the first domain and a domain of at least 95% sequence identity to the second domain; or
a domain of at least 95% sequence identity to the first domain and a domain identical in sequence to the second domain,
wherein at least one or both of the domains present in the second CAR comprises at least one or more amino acid sequence differences compared to one or both of the first domain and second domain of the first CAR in the portion comprising the modified junction region.

32. The method of any of embodiments 29-31, wherein:
the first CAR comprises a CD28 transmembrane domain and a 4-1BB co-stimulatory domain that together comprise the sequence of amino acids set forth in SEQ ID NO:5 or a variant or functional portion thereof comprising a sequence of amino acids that is at least 95% identical to SEQ ID NO:5 and comprises the junction region; and
the second CAR comprises a sequence that is modified compared to the first CAR, the modification comprising at least one amino acid sequence difference in a portion comprising a sequence of between residue 13 and 42 or between 15 and 40, with reference to numbering set forth in SEQ ID NO:5.

33. The method of any of embodiments 18-32, wherein the second CAR comprises no more than 20 amino acid sequence differences compared to the first CAR or the second CAR comprises at least 95% amino acid sequence identity to the first CAR.

34. The method of any of embodiments 18-33, wherein a region of the second CAR containing at least one of the one or more sequence differences:
contains fewer 8-15 amino acid portions, as compared to the corresponding region of the first CAR, that has a binding affinity for a human leukocyte antigen (HLA) molecule of an IC50 of less than 1000 nM; or
has a binding affinity for a human leukocyte antigen (HLA) molecule that is lower than the binding affinity for the same HLA molecule of a peptide fragment having the sequence of the corresponding portion of the junction region of the reference chimeric receptor; or
has a binding affinity of at least one peptide fragment within the region, or a reduced average binding affinity of all peptide fragments having the sequence of an 8-15 amino acid portion within the region, for a human leukocyte antigen (HLA) molecule, as compared to the corresponding region of the first CAR.

35. The method of any of embodiments 18-34, wherein a reduced detectable immune response is generated in the subject following the administration of cells expressing the second CAR to the corresponding region of the second CAR that comprises at least one amino acid sequence difference compared to the immune response generated in the subject to the region in the first CAR following its administration to the subject.

36. The method of any of any of embodiments 1-17, wherein:
the first CAR comprises a CD28 transmembrane domain or a functional portion thereof and a 4-1BB costimulatory signaling domain or a function portion thereof; and
the second CAR comprises a transmembrane domain and a costimulatory signaling domain that is distinct from one or both of such domains in the first CAR.

37. The method of any of embodiments 1-36, wherein the second CAR comprises at least one region identical in amino acid sequence to a corresponding region of the first CAR.

38. The method of embodiment 37, wherein the corresponding region of the first CAR is a region to which the subject does not exhibit a detectable humoral or cell-mediated immune response at the time of the administration of the cells expressing the second CAR.

39. The method of embodiment 37 or embodiment 38, wherein the corresponding region of the first CAR comprises a region within a CAR portion selected from the group consisting of a costimulatory domain, an ITAM-containing domain, a transmembrane domain, a transduction or expression marker, a sequence endogenous to the host, and/or an antibody domain derived from the same species as the host.

40. The method of any of embodiments 1-39, wherein the maximum number of CAR-expressing cells, the area under the curve (AUC) for CAR-expressing cells over time, and/or the duration of detectable CAR-expressing cells in the subject following the administration of cells expressing the second CAR is greater as compared to that achieved via a method comprising an alternative dosing regimen comprising performing the administration of cells expressing the first CAR followed by performing a second administration of cells expressing the first CAR, said second administration being carried out at the same point in time as the administration of cells expressing the second CAR.

41. The method of any of embodiments 1-40, wherein:
the method results in a maximum concentration or number of CAR-expressing cells in the blood of the subject of at least at or about 10 CAR-expressing cells per microliter, at least 50% of the total number of peripheral blood mononuclear cells (PBMCs), at least at least about $1\times10^5$ CAR-expressing cells, or at least 1,000, or at least 2,000, or at least 3,000, or at least 4,000, or at least 5,000 copies of CAR-encoding DNA per micrograms DNA; and/or
at day 30, at day 60, or at day 90 following the initiation of the administration of cells expressing the second CAR, CAR-expressing cells are detectable in the blood or serum of the subject; and/or at day 30, at day 60, or at day 90 following the initiation of the administration of cells expressing the second CAR, the blood of the subject contains at least 20% CAR-expressing cells, at least 10 CAR-expressing cells per microliter or at least $1 \times 10^4$ CAR-expressing cells.

42. The method of any of embodiments 1-41, wherein the dose of cells expressing the first CAR and/or the dose of cells expressing the second CAR independently comprise cells in an amount sufficient for reduction in burden of a disease or condition in the subject.

43. The method of any of embodiments 1-42, wherein the administration of cells expressing the first CAR and/or the administration of cells expressing the second CAR effects a reduction in burden of the disease or condition in the subject, thereby treating the disease or condition.

44. The method of any of embodiments 1-43, wherein the cells are T cells.

45. The method of any of embodiments 1-44, wherein the T cells are autologous to the subject.

46. A method of treatment, comprising administering cells to a subject, wherein said cells do not express a first chimeric antigen receptor (CAR) and express a second CAR, wherein:
said subject has previously received an administration of cells expressing the first CAR;
said first CAR specifically binds to an antigen associated with a disease or condition in the subject; and
said second CAR specifically binds to the antigen specifically bound by the first CAR or a different antigen associated with the disease or condition in the subject.

47. The method of embodiment 46, wherein prior to administering cells expressing the second CAR, administering to the subject cells expressing the first CAR.

48. The method of any of embodiments 46-47, wherein, at the time of or immediately prior to the administration of cells expressing the second CAR:
the subject exhibits a detectable humoral and/or cell-mediated immune response specific for the first CAR;
the disease or condition persists in the subject; and/or
the disease or condition has relapsed in the subject.

49. The method of any of embodiments 46-48, wherein:
the time between the administration of cells expressing the first CAR and the administration of cells expressing the second CAR is at least about 28 days, at least about 35 days, at least about 42 days, at least about 49 days, and/or at least about 60 days.

50. The method of any of embodiments 46-49, wherein said first CAR comprises at least one immunoreactive epitope that is not present in said second CAR.

51. The method of embodiment 50, wherein:
said at least one immunoreactive epitope comprises at least one B cell epitope; and/or
said at least one immunoreactive epitope comprises at least one T cell epitope.

52. The method of any of embodiments 46-51, wherein said subject has not received a dose of cells expressing the second CAR prior to the administration.

53. The method of any of embodiments 46-52, wherein the second CAR specifically binds to the same antigen as the first CAR.

54. The method of any of embodiments 46-53, wherein the disease or condition is a tumor.

55. The method of any of embodiments 46-54, wherein the disease or condition is a B cell malignancy.

56. The method of embodiment 53, wherein the first CAR and the second CAR specifically bind to the same epitope of said antigen.

57. The method of any of embodiments 53-56, wherein the first CAR competes for binding to said antigen with the second CAR.

58. The method of any of embodiments 53-55 and 57, wherein the first CAR and the second CAR specifically bind to distinct epitopes of said antigen.

59. The method of any of embodiments 46-58, wherein:
the second CAR specifically binds to another antigen associated with said disease or condition compared to the antigen bound by the first CAR; or the second CAR does not specifically bind to the antigen specifically bound by the first CAR.

60. The method of any of embodiments 55-59, wherein the first CAR specifically binds to an antigen associated with a B cell malignancy that is selected from CD19, CD22 or CD20 and the second CAR binds to another antigen from among CD19, CD22 or CD20 that is distinct from the antigen bound by the first CAR.

61. The method of embodiment 60, wherein the first CAR specifically binds to CD19 and the second CAR specifically binds to CD22.

62. The method of any of embodiments 46-52, wherein the cells expressing the second CAR do not comprise a receptor that specifically binds to said antigen specifically bound by the first CAR.

63. The method of any of embodiments 46-62, wherein the subject does not exhibit a detectable humoral or cell-mediated immune response against the second CAR within about 30 days, within about 60 days, or within about 90 days, of the administration of cells expressing the second CAR.

64. The method of any of embodiments 46-63, wherein the second CAR comprises one or more differences in amino acid sequence compared to the first CAR.

65. The method of embodiment 64, wherein
the one or more differences comprise at least one amino acid sequence difference compared to a region of the first CAR to which a detectable immune response is generated in the subject following the administration of cells expressing the first CAR; and/or
the one or more differences comprise at least one amino acid sequence difference compared to each region of the first CAR to which a detectable immune response is generated in the subject following the administration of cells expressing the first CAR.

66. The method of any of embodiments 46-65, further comprising, prior to the administration of cells expressing the second CAR, detecting the presence of a CAR-specific immune response in the subject.

67. The method of embodiment 66, wherein the detection comprises identifying at least a region of the first CAR to which the subject exhibits a specific immune response.

68. The method of embodiment 67, wherein the second CAR contains one or more amino acid sequence differences compared to said region of the first CAR for which the immune response is specific.

69. The method of any of embodiments 65-68, wherein the region of the first CAR comprises a region within one or more CAR portions selected from the group consisting of an scFv portion, a linker portion, an amino acid sequence not endogenous to the subject, a sequence derived from a different species than that of the subject, and/or a junction between two CAR domains; and/or where the region of the first CAR is a junction region comprising amino acids on each side of a junction between two domains.
70. The method of embodiment 69, wherein:
the region comprises a framework region (FR) within the scFv portion,
the region comprises a heavy chain FR sequence
the region comprises a heavy chain CDR sequence,
the region comprises a light chain FR sequence, and/or
the region comprises a light chain CDR sequence.
71. The method of embodiment 69, wherein the region comprises a junction region, wherein the junction region comprises up to 15 contiguous amino acids directly C-terminal of a junction that joins a first domain and a second domain of the first CAR and/or up to 15 contiguous amino acids directly N-terminal of the junction, and optionally further comprises the junction.
72. The method of embodiment 71, wherein:
the first domain and/or second domain comprise a domain of a natural or endogenous human protein or a domain having 100% identity with a domain or functional portion thereof of a natural or endogenous human protein, wherein the natural or endogenous human protein optionally is expressed by the subject to be treated; and/or
the first domain and/or second domain comprises an extracellular binding domain, a hinge domain, a transmembrane domain, or an intracellular signaling domain, which intracellular signaling domain is, optionally, a costimulatory signaling domain or an activating cytoplasmic signaling domain.
73. The method of embodiment 72, wherein the first domain and second domain are not present in the same molecule in vivo in a human subject, or are not present in a single natural or endogenous human protein or polypeptide.
74. The method of embodiment 72 or embodiment 73, wherein the first domain and second domain are or comprise, respectively, an extracellular ligand binding domain and a hinge domain, a hinge domain and a transmembrane domain, a transmembrane domain and an intracellular costimulatory signaling domain, and an intracellular costimulatory signaling domain and an activating cytoplasmic signaling domain, which can include functional portions of such domains.
75. The method of any of embodiments 72-74, wherein the first domain is or comprises a transmembrane domain or a functional portion thereof and the second domain is or comprises a costimulatory signaling domain or a functional portion thereof.
76. The method of embodiment 75, wherein the transmembrane domain is a CD28 transmembrane domain or a functional portion thereof and the costimulatory signaling domain is a 4-1BB signaling domain or a functional portion thereof.
77. The method of any of embodiments 72-76, wherein the second CAR comprises:
a domain of at least 95% sequence identity to the first domain and/or a domain of at least 95% sequence identity to the second domain;
a domain identical in sequence to the first domain and a domain of at least 95% sequence identity to the second domain; or
a domain of at least 95% sequence identity to the first domain and a domain identical in sequence to the second domain,
wherein at least one or both of the domains present in the second CAR comprises at least one or more amino acid sequence differences compared to one or both of the first domain and second domain of the first CAR in the portion comprising the modified junction region.
78. The method of any of embodiments 75-77, wherein:
the first CAR comprises a CD28 transmembrane domain and a 4-1BB co-stimulatory domain that together comprise the sequence of amino acids set forth in SEQ ID NO:5 or a variant or functional portion thereof comprising a sequence of amino acids that is at least 95% identical to SEQ ID NO:5 and comprises the junction region; and
the second CAR comprises a sequence that is modified compared to the first CAR, the modification comprising at least one amino acid sequence difference in a portion comprising a sequence of between residue 13 and 42 or between 15 and 40, with reference to numbering set forth in SEQ ID NO:5.
79. The method of any of embodiments 64-78, wherein the second CAR comprises no more than 20 amino acid sequence differences compared to the first CAR or the second CAR comprises at least 95% amino acid sequence identity to the first CAR.
80. The method of any of embodiments 64-79, wherein a region of the second CAR containing at least one of the one or more sequence differences:
contains fewer 8-15 amino acid portions, as compared to the corresponding region of the first CAR, that has a binding affinity for a human leukocyte antigen (HLA) molecule of an 1050 of less than 1000 nM; or
has a binding affinity for a human leukocyte antigen (HLA) molecule that is lower than the binding affinity for the same HLA molecule of a peptide fragment having the sequence of the corresponding portion of the junction region of the reference chimeric receptor; or
has a binding affinity of at least one peptide fragment within the region, or a reduced average binding affinity of all peptide fragments having the sequence of an 8-15 amino acid portion within the region, for a human leukocyte antigen (HLA) molecule, as compared to the corresponding region of the first CAR.
81. The method of any of embodiments 64-80, wherein a reduced detectable immune response is generated in the subject following the administration of cells expressing the second CAR to the corresponding region of the second CAR that comprises at least one amino acid sequence difference compared to the immune response generated in the subject to the region in the first CAR following its administration to the subject.
82. The method of any of any of embodiments 46-63, wherein:
the first CAR comprises a CD28 transmembrane domain or a functional portion thereof and a 4-1BB costimulatory signaling domain or a function portion thereof; and
the second CAR comprises a transmembrane domain and a costimulatory signaling domain that is distinct from one or both of such domains in the first CAR.
83. The method of any of embodiments 46-82, wherein the second CAR comprises at least one region identical in amino acid sequence to a corresponding region of the first CAR.
84. The method of embodiment 83, wherein the corresponding region of the first CAR is a region to which the subject does not exhibit a detectable humoral or cell-mediated immune response at the time of the administration of the cells expressing the second CAR.

85. The method of embodiment 83 or embodiment 84, wherein the corresponding region of the first CAR comprises a region within a CAR portion selected from the group consisting of a costimulatory domain, an ITAM-containing domain, a transmembrane domain, a transduction or expression marker, a sequence endogenous to the host, and/or an antibody domain derived from the same species as the host.

86. The method of any of embodiments 46-85, wherein the maximum number of CAR-expressing cells, the area under the curve (AUC) for CAR-expressing cells over time, and/or the duration of detectable CAR-expressing cells in the subject following the administration of cells expressing the second CAR is greater as compared to that achieved via a method comprising an alternative dosing regimen comprising performing the administration of cells expressing the first CAR followed by performing a second administration of cells expressing the first CAR, said second administration being carried out at the same point in time as the administration of cells expressing the second CAR.

87. The method of any of embodiments 46-86, wherein:
the method results in a maximum concentration or number of CAR-expressing cells in the blood of the subject of at least at or about 10 CAR-expressing cells per microliter, at least 50% of the total number of peripheral blood mononuclear cells (PBMCs), at least at least about $1 \times 10^5$ CAR-expressing cells, or at least 1,000, or at least 2,000, or at least 3,000, or at least 4,000, or at least 5,000 copies of CAR-encoding DNA per micrograms DNA; and/or
at day 30, at day 60, or at day 90 following the initiation of the administration of cells expressing the second CAR, CAR-expressing cells are detectable in the blood or serum of the subject; and/or
at day 30, at day 60, or at day 90 following the initiation of the administration of cells expressing the second CAR, the blood of the subject contains at least 20% CAR-expressing cells, at least 10 CAR-expressing cells per microliter or at least $1 \times 10^4$ CAR-expressing cells.

88. The method of any of embodiments 46-87, wherein the dose of cells expressing the first CAR and/or the dose of cells expressing the second CAR independently comprise cells in an amount sufficient for reduction in burden of a disease or condition in the subject.

89. The method of any of embodiments 46-88, wherein the administration of cells expressing the first CAR and/or the administration of cells expressing the second CAR effects a reduction in burden of the disease or condition in the subject, thereby treating the disease or condition.

90. The method of any of embodiments 46-89, wherein the cells are T cells.

91. The method of any of embodiments 46-90, wherein the T cells are autologous to the subject.

XIII. EXAMPLES

The following examples are included for illustrative purposes only and are not intended to limit the scope of the invention.

Example 1

Analysis of Transgene Product-Specific Host Immune Responses

Pre- and post-treatment peripheral blood mononuclear cells (PBMC) samples were obtained from four (4) subjects with B cell malignancies treated with autologous T cells expressing a CD19-specific CAR. The CAR included an anti-CD19 scFv derived from murine antibody, a hinge domain, a CD28 transmembrane domain, a 4-1BB intracellular signaling domain, a CD3-zeta intracellular signaling domain, a T2A domain, and a truncated EGFR (EGFRt) portion.

Pre- and post (day 42)-infusion PBMCs obtained from the subjects were assessed to detect the presence or absence of specific anti-CAR immune responses essentially as described by Berger et al. Blood. 2006 March; 107(6): 2294-2302, Berger et al. J Virol. 2001 January 75(2): 799-808, Riddell et al. Nature Medicine. 1996 February 2(2): 216-223, Berger et al. Blood. 2005 February 105(4): 1640-1647. Briefly, PBMCs (responders) were stimulated in vitro with autologous gamma-irradiated cells transduced with the CAR expressed by the administered cells (stimulators at a 1:1 or 2:1 responder-to-stimulator ratio). The cultures then were assessed in a chromium release assay for cytotoxicity against autologous $^{51}$Cr-labeled CAR-transduced ("CD19 CAR") and non-transduced ("Mock") T cells (targets) at various effector-to-target (E/T) ratios. Following co-incubation, release of chromium was quantified and the percentage of maximum achievable lysis in each sample determined.

The results for samples derived from one exemplary patient are shown in FIG. 1, which depicts the cytolytic activity of PBMCs pre-infusion and post-infusion at day 42. Whereas no cytolytic activity specific for CAR-transduced target cells was detected in any pre-infusion PBMC-derived cultures, in two of the four subjects assessed, CAR-specific lytic activity was detected in cultures derived from post-infusion PBMC samples. These results indicate that CAR-specific immune responses can develop following a single infusion of CAR-expressing T cells.

Epitope mapping was carried out to assess region(s) of the CAR recognized by the specific immune responses. Pre- and post-infusion PBMC samples were stimulated in the presence of individual pools of multiple 15-mer peptides, with sequences representing overlapping portions (11 amino acid overlap) of the entire length of an approximately 500 amino acid sequence of the CAR expressed by the administered cells. Cells were stained with antibodies to detect CD8 and CD4 surface expression and intracellular expression of cytokine. Twenty-three (23) pools were assessed, each containing ten (10) peptides each and collectively including 125 individual overlapping peptides, with each peptide represented in at least two of the pools.

This design permitted the generation of an analytic grid to assess responses specific for individual peptides, whereby a peptide present in more than one pool detected as hits in this assay was deemed a potentially immunogenic peptide hit. For the two patients in whom a CAR-specific immune response had been detected, six and three peptide hits, respectively, were identified.

Figure 2:
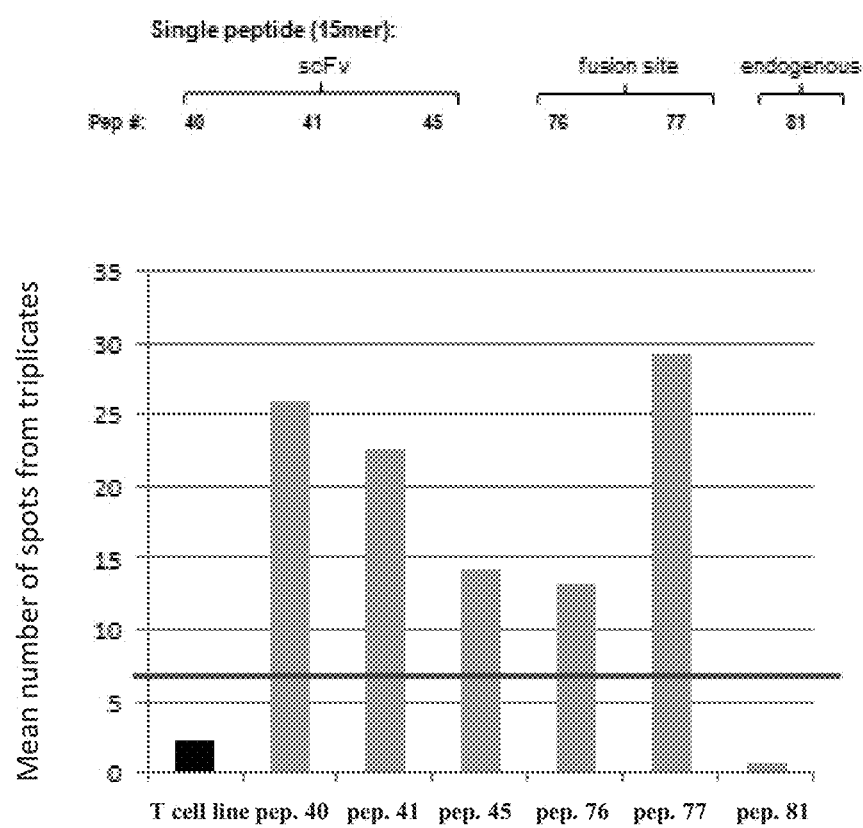
FIG. 2 shows results from an exemplary ELISpot analysis confirming immune responses to certain overlapping peptides representing particular regions of a CAR in an exemplary human subject. Numbers labeled with "pep" represent various overlapping peptides along the length of the CAR sequence, with corresponding regions indicated above the chart.

Individual ELISpot assays were performed using an anti-cytokine capture antibody to assess the presence or absence of a specific immune response for each of these individual hits (see Berger et al. (2006); Berger et al. (2001); Riddell et al. (1996); and Berger et al. (2005), supra). The results of an exemplary assay for one patient are shown in FIG. 2. Specific immune responses against peptides with sequences within the $V_H$ portion of the scFv of the CAR were detected in both patients assessed (including regions within the FR1, CDR1, and FR2 regions for one patient and within the FR3 for the other). For the first patient, specific immune responses also were detected against two overlapping 15-mer peptides, each containing the junction between the transmembrane domain and costimulatory domain of the CAR (labeled "fusion site" in FIG. 2). These two overlapping 15-mer peptides had the amino acid sequences AFIIFWVKRGRKKLL (SEQ ID NO: 8) and FWVKR-GRKKLLYIFK (SEQ ID NO: 9), respectively. In another study following administration with a different CAR having a murine scFv, CD28 transmembrane and costimulatory domains and a CD3 zeta domain, using similar methods, an immune response also was detected for one subject against a pool containing $V_H$ portions of an anti-CD19 scFv and for another subject in a pool containing junction portions.

No specific immune responses were detected in the patients by this assay against peptides within other regions. For example, in this assay, no specific responses were detected against peptides having sequences within other CDRs or framework regions of the scFv, peptides within regions of costimulatory or transmembrane domain but not spanning the junction between the two, or peptides within the EGFRt or CD3-t region of the CAR. Specific immune responses were not detected against endogenous sequences.

Example 2

In Silico Analysis of Peptides Derived from Junction Regions of a CAR for Binding to HLA Class I and HLA Class II T cell epitope prediction tools, available from the Immune Epitope Database and analysis resource (IEDB), were used for in silico analysis to predict MHC-binding affinities and other properties related to potential immunogenicity for each of a series of overlapping peptide sequences within a portion of an exemplary CAR sequence. The portion included a spacer having an immunoglobulin-derived hinge domain, a human CD28 transmembrane domain, a human 4-1BB costimulatory domain, and a human CD3zeta signaling domain. In the portion assessed, the hinge domain was a human IgG4 hinge domain, the CD28 transmembrane domain comprised a sequence set forth in SEQ ID NO:2 and the 4-1BB costimulatory domain contained the sequence set forth in SEQ ID NO:3. This portion thus contained three junctions between different domains derived from human sequences (which junctions may have represented sites of potential immunogenicity against a CAR upon administration to a human subject): the junction between the spacer region and transmembrane domain, the junction between the transmembrane domain and costimulatory domain, and the junction between the costimulatory domain and intracellular signaling domain (see FIGS. 3A and 3B).

To identify portions of the sequence that may have particular properties making them more likely to be presented to T cells, affinities for binding to 27 individual HLA class I alleles and 56 individual HLA class II alleles were predicted for overlapping peptides along the length of the portion, of 8-14 amino acids in length and of 15 amino acids in length (containing 9-mer binding core), respectively. These alleles, collectively representing HLA alleles present in greater than 99% of the worldwide population, and their approximate frequency in the United States population are listed in Tables 1A and 1B.

TABLE 1A

HLA class I

| Class I | allele | Frequency in population |
|---|---|---|
| 1 | HLA-A*01:01 | 12.94 |
| 2 | HLA-A*02:01 | 42.88 |
| 3 | HLA-A*02:03 | 0.19 |

TABLE 1A-continued

HLA class I

| Class I | allele | Frequency in population |
|---|---|---|
| 4 | HLA-A*02:06 | 1.55 |
| 5 | HLA-A*03:01 | 13.50 |
| 6 | HLA-A*11:01 | 11.60 |
| 7 | HLA-A*23:01 | 8.30 |
| 8 | HLA-A*24:02 | 22.56 |
| 9 | HLA-A*26:01 | 5.36 |
| 10 | HLA-A*30:01 | 6.29 |
| 11 | HLA-A*30:02 | 5.21 |
| 12 | HLA-A*31:01 | 6.87 |
| 13 | HLA-A*32:01 | 3.71 |
| 14 | HLA-A*33:01 | 2.62 |
| 15 | HLA-A*68:01 | 6.36 |
| 16 | HLA-A*68:02 | 4.79 |
| 17 | HLA-B*07:02 | 12.96 |
| 18 | HLA-B*08:01 | 9.23 |
| 19 | HLA-B*15:01 | 6.54 |
| 20 | HLA-B*35:01 | 13.03 |
| 21 | HLA-B*40:01 | 9.79 |
| 22 | HLA-B*44:02 | 7.22 |
| 23 | HLA-B*44:03 | 8.96 |
| 24 | HLA-B*51:01 | 8.51 |
| 25 | HLA-B*53:01 | 7.26 |
| 26 | HLA-B*57:01 | 3.49 |
| 27 | HLA-B*58:01 | 4.82 |

TABLE 1B

HLA class II

| Class II | allele | Frequency in population |
|---|---|---|
| 1 | HLA-DRB1*01:01 | 13.62 |
| 2 | HLA-DRB1*15:01 | 22.86 |
| 3 | HLA-DRB1*03:01 | 21.82 |
| 4 | HLA-DRB1*04:01 | 15.54 |
| 5 | HLA-DRB1*11:01 | 10.92 |
| 6 | HLA-DRB1*13:01 | 9.86 |
| 7 | HLA-DRB1*07:01 | 19.84 |
| 8 | HLA-DRB1*01:01 | 4.06 |
| 9 | HLA-DRB1*01:02 | 1.85 |
| 10 | HLA-DRB1*04:02 | 6.28 |
| 11 | HLA-DRB1*04:05 | 1.22 |
| 12 | HLA-DRB1*04:07 | 2.78 |
| 13 | HLA-DRB1*04:08 | 1.26 |
| 14 | HLA-DRB1*08:04 | 0.86 |
| 15 | HLA-DRB1*09:01 | 5.33 |
| 16 | HLA-DRB1*10:01 | 2.78 |
| 17 | HLA-DRB1*11:02 | 0.94 |
| 18 | HLA-DRB1*11:03 | 0.74 |
| 19 | HLA-DRB1*11:04 | 4.76 |
| 20 | HLA-DRB1*15:02 | 0.78 |
| 21 | HLA-DRB1*15:03 | 1.22 |
| 22 | HLA-DRB1*16:01 | 4.06 |
| 23 | HLA-DRB1*16:02 | 0.84 |
| 24 | HLA-DRB3*02:02 | 0.00 |
| 25 | HLA-DRB3*03:01 | 0.00 |
| 26 | HLA-DRB5*01:01 | 0.00 |
| 27 | HLA-DQA1*01:01/DQB1*05:01 | 30.57 |
| 28 | HLA-DQA1*05:01/DQB1*02:01 | 76.17 |
| 29 | HLA-DQA1*01:02/DQB1*05:02 | 21.13 |
| 30 | HLA-DQA1*01:02/DQB1*06:02 | 30.74 |
| 31 | HLA-DQA1*03:01/DQB1*03:02 | 31.56 |
| 32 | HLA-DQA1*01:02/DQB1*06:04 | 19.00 |
| 33 | HLA-DQA1*05:01/DQB1*03:01 | 80.58 |
| 34 | HLA-DQA1*02:01/DQB1*02:02 | 27.99 |
| 35 | HLA-DQA1*03:01/DQB1*03:01 | 49.92 |
| 36 | HLA-DQA1*02:01/DQB1*03:03 | 23.32 |

TABLE 1B-continued

HLA class II

| Class II | allele | Frequency in population |
|---|---|---|
| 37 | HLA-DQA1*03:03/DQB1*03:03 | 20.22 |
| 38 | HLA-DPA1*01:03/DPB1*01:01 | 99.83 |
| 39 | HLA-DPA1*01:03/DPB1*02:01 | 99.83 |
| 40 | HLA-DPA1*01:03/DPB1*03:01 | 99.82 |
| 41 | HLA-DPA1*01:03/DPB1*04:01 | 99.88 |
| 42 | HLA-DPA1*01:03/DPB1*04:02 | 99.86 |
| 43 | HLA-DPA1*01:03/DPB1*05:01 | 99.81 |
| 44 | HLA-DPA1*02:01/DPB1*01:01 | 23.54 |
| 45 | HLA-DPA1*02:01/DPB1*02:01 | 24.11 |
| 46 | HLA-DPA1*02:01/DPB1*03:01 | 17.63 |
| 47 | HLA-DPA1*02:01/DPB1*04:01 | 46.73 |
| 48 | HLA-DPA1*02:01/DPB1*04:02 | 38.04 |
| 49 | HLA-DPA1*02:01/DPB1*05:01 | 13.24 |
| 50 | HLA-DPA1*02:01/DPB1*06:01 | 8.59 |
| 51 | HLA-DPA1*02:01/DPB1*09:01 | 7.26 |
| 52 | HLA-DPA1*02:01/DPB1*11:01 | 9.98 |
| 53 | HLA-DPA1*02:01/DPB1*13:01 | 11.55 |
| 54 | HLA-DPA1*02:01/DPB1*14:01 | 7.98 |
| 55 | HLA-DPA1*02:01/DPB1*15:01 | 7.73 |
| 56 | HLA-DPA1*02:01/DPB1*17:01 | 10.40 |

Figure 4A:
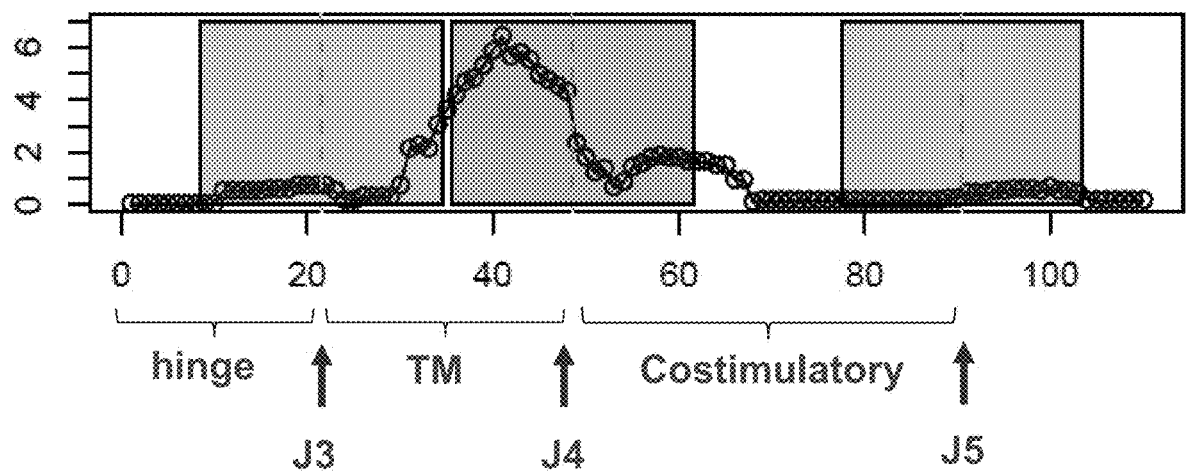
FIG. 4A and FIG. 4B depict algorithm-based T cell epitope predictions for HLA class I and HLA class II alleles, respectively, showing the total number of sequences in the dataset including each position along the length of the sequence with a predicted IC50 of less than 50 nm weighted according to the frequency of the individual HLA alleles in the population.

Algorithm-based T cell epitope prediction tools available from the IEDB were used to predict IC50 values for binding to HLA class I molecules for each 8-14 amino acid peptide in the dataset using ANN (Nielsen et al. (2003) Protein Sci., 12:1007-1017 and Lundegaard et al. (2008) NAR, 36:W509-512) and, in some cases, one or more additional prediction using SMM (Peters and Sette (2005) BMC Bioinformatics, 6:132) and comblib (Sidney et al. (2008) Immunome Res. 4:2, or the Consensus tool (see Kim, et al. (2012) Immune epitope database analysis resource, NAR (combining predictions from any of the foregoing). Predictions for IC50 values for binding to HLA class II for each 15 amino acid peptide in the dataset was made using the NetMHCIIpan method (Karosiene et al. (2013) Immunogenetics 65(10): 711; Nielsen et al. (2008) PLoS Comput Biol. 4(7) e1000107). For each individual position within the portion of the CAR amino acid sequence, the total number of sequences in the dataset that included the position and was predicted to bind to any of the class I or class II alleles with a predicted IC50 of less than 50 nm was determined. FIGS. 4A (HLA class I) and 4B (HLA class II), depict the results for class I and class II alleles, respectively, showing positional coverage along the length of the sequence, based on the determined total number, weighted according to the frequency of the individual HLA alleles in the population. The area under the curve (AUC) across the entire assessed region was approximately 1321 for HLA class I binding and 2943 for HLA class II binding. The AUC for the transmembrane-costimulatory domain region was approximately 931 for HLA class I binding and 2212 for HLA class II binding.

Figure 4B:
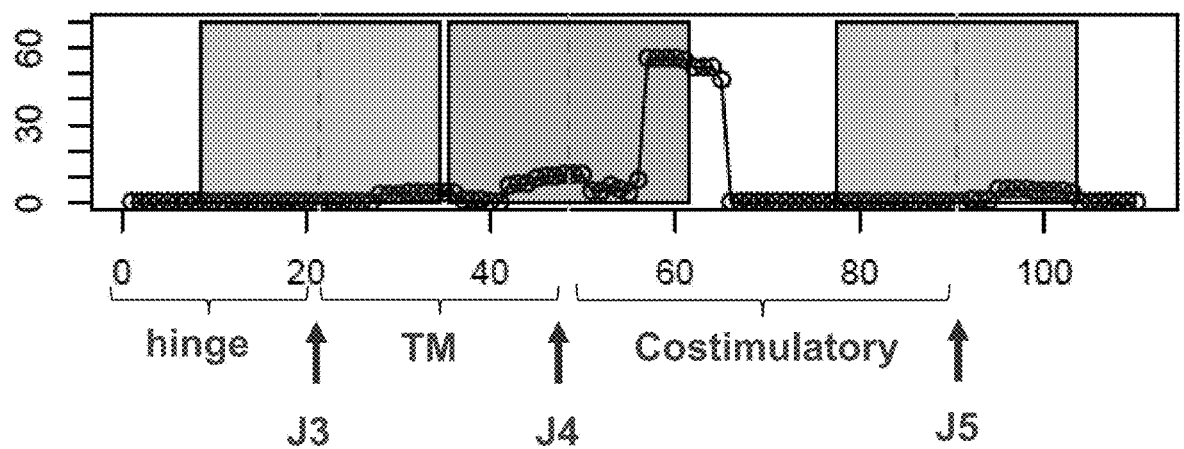

As shown in FIGS. 4A and 4B, certain portions of the sequence were predicted by this method to contain fragments more likely to bind well in MHC complexes and thus be presented as epitopes for potential recognition by T cells. Binding affinity for HLA alleles alone does not necessarily predict immunogenicity. Given that the individual domains (e.g., transmembrane, costimulatory) in this exemplary CAR were human-derived, upon administration to a human subject, immunogenic responses were less likely to develop against an epitope within any one of these individual regions alone (as opposed to an epitope spanning multiple regions not ordinarily associated with one another, and/or including a junction between such regions). For example, even for a peptide predicted to bind well to and be presented in the context of an MHC molecule, if the peptide was derived entirely from an endogenous protein, it may be recognized as "self" and thus may fail to induce a productive immune response. For example, whereas certain regions entirely within a single transmembrane or cytoplasmic domain scored highly on the HLA-binding affinity prediction, in the results described in Example 1, no immune responses were detected against peptide sequences solely within either one of these domains of a similar CAR sequence. Accordingly, while various "hot spots" were observed with respect to predicted HLA-binding affinity, subsequent assessment and alteration focused on those areas that not only had higher predicted IC50 values, but also included potential epitopes that spanned the junction between different domains derived from two different proteins.

In particular, a junction region that includes one or more potential peptide epitopes spanning the junction of the CD28 transmembrane domain and 4-1BB signaling domain of the exemplary CAR was further assessed. With respect to the sequence set forth in SEQ ID NO:5, which includes the exemplary human CD28 transmembrane domain (SEQ ID NO:2) and exemplary human 4-1BB costimulatory domain (SEQ ID NO:3), the assessed junction region contained 13 amino acids on either side of the junction spanning the CD28 transmembrane and 4-1BB costimulatory domains as follows: FWVLVVVGGVLACYSLLVTVAFIIFWV<u>K</u>RGRK<u>K</u>LLYIFKQPFMRPVQTTQEEDGCSCRFPEEEEGGCEL (SEQ ID NO:5), in which a 26 amino acid junction region is indicated by bold, and the two amino acids just C' and N' of the junction between the domains is indicated by underline. The assessed 26 amino acid junction region is set forth in SEQ ID NO:137 and corresponds to amino acid residues 15 to 40 of the sequence of amino acids set forth in SEQ ID NO:5.

In silico modeling was carried out to identify one or more amino acid modifications (mutations) within the 26-amino acid junction region set forth in SEQ ID NO: 137 resulting in peptide fragments that were predicted to bind with high IC50 values to class I and class II alleles, and thus that were likely to reduce the potential for inducing immunogenicity against a CAR containing this region. Specifically, predictions were made for variant peptide fragments of the junction region containing one or more mutations at amino acid residue positions corresponding to positions 14, 17 and 20 with numbering with reference to SEQ ID NO:137 (which correspond to one or more mutations at amino acid positions corresponding to positions 28, 31 and 34 with numbering with reference to SEQ ID NO:5). In this exemplary study, these residues were chosen for further analysis following in silico mutagenesis and binding predictions of all high affinity epitopes in which all possible single amino acid replacements across that epitope were surveyed for their impact on the predicted IC50 values. Residues that resulted in greater IC50 predictions (decrease in the binding) were identified, which identified the above residues as being sensitive to replacements.

A series of different variant junction regions were assessed, each containing one or more amino acid replacement at the assessed position(s), as compared to the non-mutated junction region within the exemplary CAR sequence. An exemplary subset of amino acid replacements at the identified positions were chosen that may be less disruptive to the structure or function of either the transmembrane region of the costimulatory signaling domain. Also, replacements were chosen that may be able to impact more than one epitope at a time, since the epitopes overlap.

Specifically, individual variant junction regions contained the following modifications (amino acid replacements): K28A, K28H, K28L, K28Q, K28S, R32A, R31H, R31L, R31N, L34A, L34S, K28Q/R31A, K28Q/R31N, K28Q/R31S, K28Q/L34A, K28Q/L34S, R31N/L34A, R31N/L34S, K28Q/R31N/L34A, K28Q/R31N/L34S, with numbering with reference to SEQ ID NO:5.

For the non-variant and variant junction regions, weighted immunogenicity scores were obtained for class I and class II alleles, using the T cell epitope prediction tools available from IEDB. Scores were derived using predicted IC50 values for each of a series of 8-mer to 14-mer overlapping peptides (for each of the 27 HLA class I alleles, individually) and a series of 15-mer overlapping peptides (for each of the 56 HLA class II alleles, individually) within the respective (variant or non-variant) 26-amino acid junction region, and were weighted based on relative frequency in the population of the individual HLA class I and class II alleles. A higher relative score is indicative of a higher degree of predicted binding.

Figure 5:
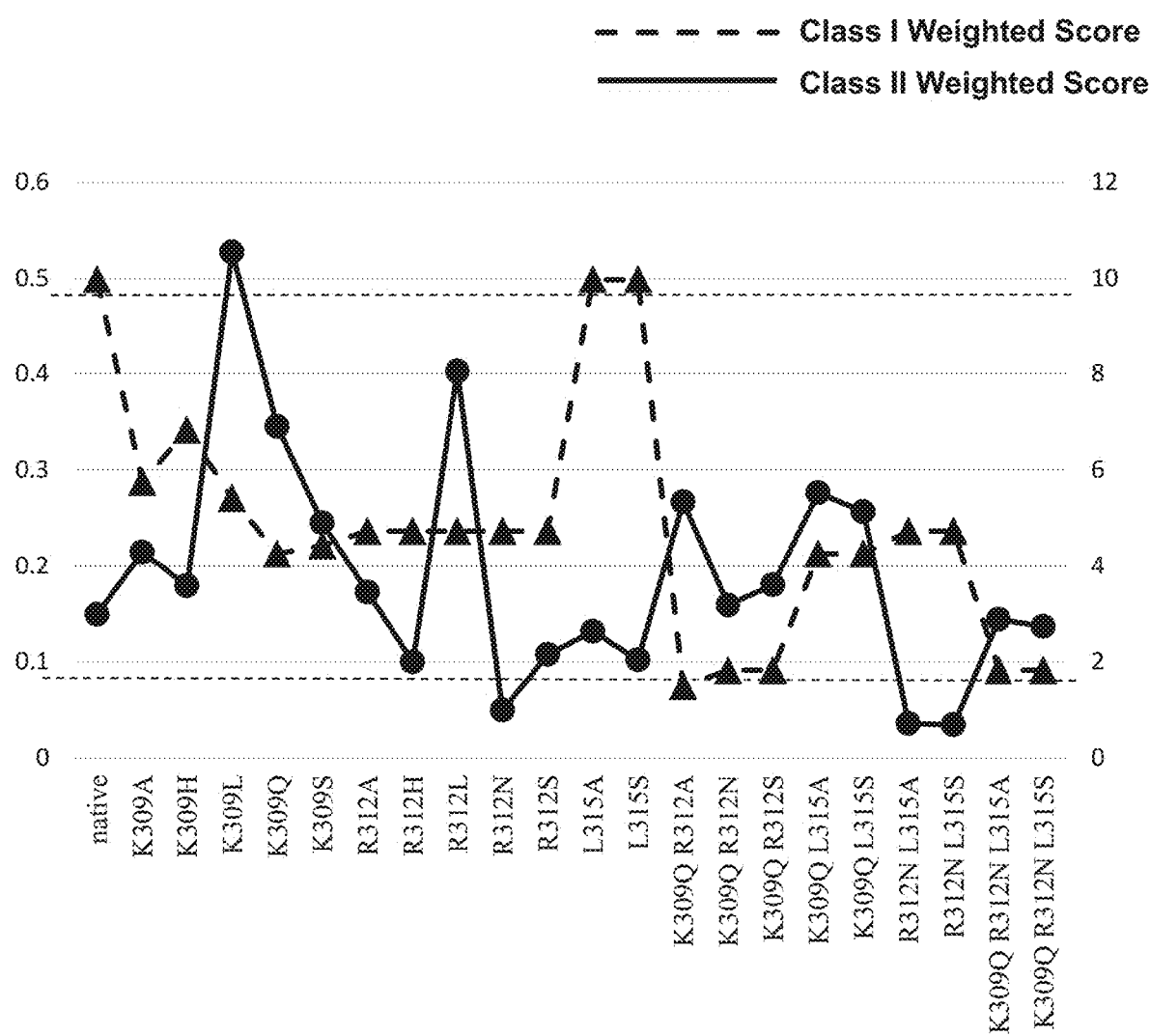
FIG. 5 depicts algorithm-based T cell epitope predictions for HLA class I and HLA class II alleles of a series of variant peptides. Scores were determined and weighted as described in Example 2. Triangles and a dotted line indicated class I weighted scores. Circles and a solid line indicate class II weighted scores.

The results are set forth in FIG. 5. The results demonstrate the ability to decrease in the overall predicted HLA class I immunogenicity score within a CAR junction region by modifying amino acids within the region. The results also confirm the ability to reduce predicted HLA class I binding affinity (and hence reduced predicted immunogenicity score) without resulting in a substantial increase in the predicted immunogenicity score for HLA class II binding. Thus, in general, the results showed that amino acid modification(s) within a region spanning a junction between a CD28 transmembrane domain and a 4-1BB costimulatory domain of a CAR could be made and effect an overall reduction in the predicted affinity for human HLA binding, which would be consistent with a reduction in potential for immunogenicity, upon administration to a human subject, of a chimeric receptor identical to a receptor having this region, but containing the modification or combination of modifications in this region.

Example 3

Comparison of In Silico Analysis and In Vitro Binding of Peptides Derived from Junction Regions of a CAR for Binding to HLA Class I Actual binding affinities for certain HLA class I alleles (A*02:01, A*03:01, A*11:01, and B*08:01) were assessed in vitro for exemplary overlapping 9 amino acid peptide sequences within a portion of the 26 amino acid junction region spanning the CD28 and 4-1BB junction. Specifically, assessment was of a series of overlapping 9-mer peptides derived from the sequence VAFIIFWVKRGRKKLL (set forth in SEQ ID NO: 7), which contains a portion of the CD28 transmembrane domain and 4-1BB costimulatory domain spanning the junction between the domains (bond joining the two amino acids noted in underline). In addition, a series of overlapping 9-mer peptides of each of a number of different variants of this portion also were assessed, each variant containing a mutation or mutations in this region as described in Example 2.

The various 9-mer overlapping peptides were synthesized and their purity tested by MALDI-TOF Mass Spectrometry. The synthetic peptides were then incubated with recombinant MHC molecules to assess binding properties using the REVEAL Epitope Discovery System, which is a high-throughput binding assay that measures the degree to which each peptide is able to stabilize a ternary MHC-peptide complex (ProImmune, Oxford, United Kingdom). Each peptide was separately tested for this ability with respect to each of the HLA class I alleles, normalized to the degree observed for a positive control (known T cell epitope for the relevant allele). The results are reported as a score, in which the binding was normalized to the positive control peptide set at 100%. In this analysis, a score of greater than 50 generally was considered to represent good or high affinity binding.

The results were compared to predicted binding (IC50) values obtained for binding of the same peptide:MHC complex, using the in silico prediction methods as described in Example 2. Since the maximum IC50 value predicted was about 50,000, the IC50 values were log transformed, subtracted from LOG(50000) and divided by LOG(50000) to obtain a normalized in silico score ((Log(50000)−log IC50)/Log(50000)). In this analysis, an in silico binding prediction score of greater than 2.0 generally was considered to represent predicted good or high affinity binding.

The results are set forth in Table 2A (HLA-A*02:01 and HLA-A*03:01) and Table 2B (HLA-A*11:01 and HLA-B*08:01). In general, the in silico binding predictions were predictive of the actual in vitro binding results. In some cases, a relatively higher binding was predicted in silico, but not observed in the in vitro assay.

The results also were consistent with predicted binding affinity being generally predictive of affinity as measured in the in vitro assay. Additionally, the results demonstrated successful reduction of binding affinity to an HLA by modifications within a junction region, and that it was possible to modify the sequence in a way that resulted in a lower predicted or actual binding affinity or score of one of the overlapping potential epitopes, without increasing (or while also reducing) binding affinity or score for another of the overlapping epitopes containing the same residue. In some embodiments, such mutations or modifications may be particularly advantageous. As a non-limiting example of the results, modifications K29L, R31H, L34S and/or L34A, with reference to numbering set forth in SEQ ID NO:5, generally resulted in a reduced predicted or actual binding affinity or score for at least one HLA allele and/or for at least one peptide within the region assessed, without resulting in a higher binding affinity to another HLA allele and/or without resulting in a higher binding affinity for another peptide.

TABLE 2A

In Silico and In Vitro MHC binding of Variant Peptides

| Overlapping Reference Peptide | Peptide Sequence | Mutation | A*02:01 | | | A*03:01 | | | SEQ ID NO. |
|---|---|---|---|---|---|---|---|---|---|
| | | | IEDB IC50 | In Silico Score | In Vitro Score | IEDB IC50 | In Silico | In Vitro | |
| 1 | VAFIIFWVK | none | 19617 | 0.41 | 0.70 | 262 | 2.28 | 1.50 | 16 |
| 2 | AFIIFWVKR | none | 25314 | 0.30 | 0.50 | 17846 | 0.45 | 5.70 | 17 |

TABLE 2A -continued

In Silico and In Vitro MHC binding of Variant Peptides

| Over-lapping Reference Peptide | Peptide Sequence | Mutation | A*02:01 IEDB IC50 | A*02:01 In Silico Score | A*02:01 In Vitro Score | A*03:01 IEDB IC50 | A*03:01 In Silico | A*03:01 In Vitro | SEQ ID NO. |
|---|---|---|---|---|---|---|---|---|---|
| 3 | FIIFWVKRG | none | 7967 | 0.80 | 10.10 | 23693 | 0.32 | 1.40 | 18 |
| 4 | IIFWVKRGR | none | 24769 | 0.31 | 1.70 | 406 | 2.09 | 24.30 | 19 |
| 5 | IFWVKRGRK | none | 30463 | 0.22 | 4.50 | 3482 | 1.16 | 20.50 | 20 |
| 6 | FWVKRGRKK | none | 28878 | 0.24 | 3.50 | 17327 | 0.46 | 2.20 | 21 |
| 7 | WVKRGRKKL | none | 27956 | 0.25 | 1.40 | 22961 | 0.34 | 13.10 | 22 |
| 1 | VAFIIFWVS | K29S | 12273 | 0.61 | 70.60 | 22660 | 0.34 | 0.70 | 23 |
| 2 | AFIIFWVSR | K29S | 23924 | 0.32 | 4.50 | 18157 | 0.44 | 0.30 | 24 |
| 3 | FIIFWVSRG | K29S | 3382 | 1.17 | 0.20 | 21751 | 0.36 | 0.10 | 25 |
| 4 | IIFWVSRGR | K29S | 21442 | 0.37 | 2.60 | 155 | 2.51 | 25.30 | 26 |
| 5 | IFWVSRGRK | K29S | 30615 | 0.21 | 1.30 | 1880 | 1.42 | 39.20 | 27 |
| 6 | FWVSRGRKK | K29S | 28679 | 0.24 | 1.50 | 17832 | 0.45 | 2.90 | 28 |
| 7 | WVSRGRKKL | K29S | 23551 | 0.33 | 2.30 | 22394 | 0.35 | 2.10 | 29 |
| 1 | VAFIIFWVL | K29L | 1336 | 1.57 | 0.20 | 20145 | 0.39 | 0.00 | 30 |
| 2 | AFIIFWVLR | K29L | 22444 | 0.35 | 5.70 | 15583 | 0.51 | 0.30 | 31 |
| 3 | FIIFWVLRG | K29L | 2037 | 1.39 | 7.20 | 20853 | 0.38 | 0.10 | 32 |
| 4 | IIFWVLRGR | K29L | 17613 | 0.45 | 8.40 | 238 | 2.32 | 2.80 | 33 |
| 5 | IFWVLRGRK | K29L | 30293 | 0.22 | 2.90 | 3675 | 1.13 | 19.50 | 34 |
| 6 | FWVLRGRKK | K29L | 28857 | 0.24 | 3.30 | 16996 | 0.47 | 0.40 | 35 |
| 7 | WVLRGRKKL | K29L | 19522 | 0.41 | 2.40 | 23063 | 0.34 | 0.70 | 36 |
| 1 | VAFIIFWVH | K29H | 23252 | 0.33 | 3.10 | 10359 | 0.68 | 0.30 | 37 |
| 2 | AFIIFWVHR | K29H | 22819 | 0.34 | 0.30 | 18506 | 0.43 | 0.30 | 38 |
| 3 | FIIFWVHRG | K29H | 1691 | 1.47 | 37.30 | 22930 | 0.34 | 0.00 | 39 |
| 4 | IIFWVHRGR | K29H | 23573 | 0.33 | 4.70 | 326 | 2.19 | 30.10 | 40 |
| 5 | IFWVHRGRK | K29H | 29930 | 0.22 | 7.10 | 1062 | 1.67 | 37.80 | 41 |
| 6 | FWVHRGRKK | K29H | 28189 | 0.25 | 1.60 | 17052 | 0.47 | 3.60 | 42 |
| 7 | WVHRGRKKL | K29H | 25035 | 0.30 | 1.60 | 22278 | 0.35 | 3.40 | 43 |
| 1 | VAFIIFWVA | K29A | 2733 | 1.26 | 28.50 | 21010 | 0.38 | 0.00 | 44 |
| 2 | AFIIFWVAR | K29A | 23072 | 0.34 | 2.20 | 17755 | 0.45 | 0.50 | 45 |
| 3 | FIIFWVARG | K29A | 1902 | 1.42 | | 22486 | 0.35 | | 102 |
| 4 | IIFWVARGR | K29A | 22077 | 0.36 | 9.60 | 206 | 2.39 | 18.60 | 46 |
| 5 | IFWVARGRK | K29A | 30251 | 0.22 | 1.00 | 3893 | 1.11 | 53.70 | 47 |
| 6 | FWVARGRKK | K29A | 28353 | 0.25 | 13.50 | 16210 | 0.49 | 5.00 | 48 |
| 7 | WVARGRKKL | K29A | 22630 | 0.34 | 8.80 | 22548 | 0.35 | 1.30 | 49 |
| 1 | VAFIIFWVQ | K29Q | 17921 | 0.45 | 5.30 | 22927 | 0.34 | 0.20 | 50 |
| 2 | AFIIFWVQR | K29Q | 24165 | 0.32 | 0.40 | 19279 | 0.41 | 0.20 | 51 |
| 3 | FIIFWVQRG | K29Q | 4152 | 1.08 | 16.80 | 23136 | 0.33 | 0.40 | 52 |

TABLE 2A-continued

In Silico and In Vitro MHC binding of Variant Peptides

| Over-lapping Reference Peptide | Peptide Sequence | Mutation | A*02:01 | | | A*03:01 | | | SEQ ID NO. |
|---|---|---|---|---|---|---|---|---|---|
| | | | IEDB IC50 | In Silico Score | In Vitro Score | IEDB IC50 | In Silico | In Vitro | |
| 4 | IIFWVQRGR | K29Q | 21783 | 0.36 | 5.80 | 231 | 2.34 | 18.00 | 53 |
| 5 | IFWVQRGRK | K29Q | 30704 | 0.21 | 6.10 | 3177 | 1.20 | 36.70 | 54 |
| 6 | FWVQRGRKK | K29Q | 29501 | 0.23 | 5.20 | 18619 | 0.43 | 6.40 | 55 |
| 7 | WVQRGRKKL | K29Q | 24480 | 0.31 | 8.10 | 23630 | 0.33 | 4.90 | 56 |
| 4 | IIFWVKRGS | R32S | 18902 | 0.42 | 13.60 | 19450 | 0.41 | 16.20 | 57 |
| 5 | IFWVKRGSK | R32S | 29391 | 0.23 | 2.40 | 3348 | 1.17 | 10.40 | 58 |
| 6 | FWVKRGSKK | R32S | 28317 | 0.25 | 1.90 | 14227 | 0.55 | 5.90 | 59 |
| 7 | WVKRGSKKL | R32S | 23485 | 0.33 | 3.00 | 22637 | 0.34 | 1.90 | 60 |
| 4 | IIFWVKRGL | R32L | 2692 | 1.27 | 82.20 | 16661 | 0.48 | 15.90 | 61 |
| 5 | IFWVKRGLK | R32L | 29250 | 0.23 | 2.40 | 1973 | 1.40 | 26.90 | 62 |
| 6 | FWVKRGLKK | R32L | 27554 | 0.26 | 9.40 | 14434 | 0.54 | 2.70 | 63 |
| 7 | WVKRGLKKL | R32L | 20709 | 0.38 | 24.50 | 22985 | 0.34 | 10.00 | 64 |
| 4 | IIFWVKRGH | R32H | 27453 | 0.26 | 5.30 | 1665 | 1.48 | 26.60 | 65 |
| 5 | IFWVKRGHK | R32H | 29806 | 0.22 | 2.20 | 3806 | 1.12 | 9.00 | 66 |
| 6 | FWVKRGHKK | R32H | 27689 | 0.26 | 2.60 | 16743 | 0.48 | 4.10 | 67 |
| 7 | WVKRGHKKL | R32H | 25923 | 0.29 | 3.90 | 22313 | 0.35 | 1.40 | 68 |
| 4 | IIFWVKRGA | R32A | 6107 | 0.91 | 85.90 | 16069 | 0.49 | 42.90 | 69 |
| 5 | IFWVKRGAK | R32A | 29354 | 0.23 | 13.80 | 3470 | 1.16 | 22.00 | 70 |
| 6 | FWVKRGAKK | R32A | 28151 | 0.25 | 4.30 | 17066 | 0.47 | 4.70 | 71 |
| 7 | WVKRGAKKL | R32A | 24746 | 0.31 | 4.70 | 22982 | 0.34 | 4.10 | 72 |
| 4 | IIFWVKRGN | R32N | 25979 | 0.28 | 9.30 | 18552 | 0.43 | 4.30 | 73 |
| 5 | IFWVKRGNK | R32N | 29978 | 0.22 | 3.50 | 2669 | 1.27 | 8.00 | 74 |
| 6 | FWVKRGNKK | R32N | 28430 | 0.25 | 8.70 | 17713 | 0.45 | 3.60 | 75 |
| 7 | WVKRGNKKL | R32N | 24790 | 0.30 | 2.40 | 22813 | 0.34 | 0.90 | 76 |
| 4 | IIFWVQRGS | K29Q/R32S | 14326 | 0.54 | 22.40 | 17741 | 0.45 | 4.50 | 77 |
| 5 | IFWVQRGSK | K29Q/R32S | 29540 | 0.23 | 33.50 | 3052 | 1.212 | 0.30 | 78 |
| 6 | FWVQRGSKK | K29Q/R32S | 28907 | 0.24 | 0.80 | 15992 | 0.50 | 1.90 | 79 |
| 7 | WVQRGSKKL | K29Q/R32S | 18121 | 0.44 | 4.40 | 23279 | 0.33 | 1.20 | 80 |
| 4 | IIFWVQRGA | K29Q/R32A | 2658 | 1.27 | 95.30 | 13467 | 0.57 | 2.70 | 81 |
| 5 | IFWVQRGAK | K29Q/R32A | 29482 | 0.23 | 11.70 | 3205 | 1.191 | 7.00 | 82 |
| 6 | FWVQRGAKK | K29Q/R32A | 28792 | 0.24 | 2.20 | 18649 | 0.43 | 2.70 | 83 |
| 7 | WVQRGAKKL | K29Q/R32A | 20217 | 0.39 | 3.00 | 23651 | 0.33 | 2.00 | 84 |
| 4 | IIFWVQRGN | K29Q/R32N | 23103 | 0.34 | 13.00 | 16590 | 0.48 | 3.60 | 85 |
| 5 | IFWVQRGNK | K29Q/R32N | 30164 | 0.22 | 16.10 | 2438 | 1.31 | 23.20 | 86 |
| 6 | FWVQRGNKK | K29Q/R32N | 29113 | 0.23 | 3.10 | 19165 | 0.42 | 1.30 | 87 |
| 7 | WVQRGNKKL | K29Q/R32N | 19790 | 0.40 | 4.30 | 23457 | 0.33 | 1.50 | 88 |

TABLE 2A-continued

In Silico and In Vitro MHC binding of Variant Peptides

| Overlapping Reference Peptide | Peptide Sequence | Mutation | A*02:01 | | | A*03:01 | | | SEQ ID NO. |
|---|---|---|---|---|---|---|---|---|---|
| | | | IEDB IC50 | In Silico Score | In Vitro Score | IEDB IC50 | In Silico | In Vitro | |
| 7 | WVKRGRKKS | L35S | 30812 | 0.21 | 3.90 | 25365 | 0.29 | 0.90 | 89 |
| 7 | WVKRGRKKA | L35A | 28556 | 0.24 | 4.50 | 24086 | 0.32 | 0.90 | 90 |
| 7 | WVQRGNKKS | K29Q/L35S | 26883 | 0.27 | 1.20 | 25680 | 0.29 | 0.70 | 91 |
| 7 | WVQRGNKKA | K29Q/L35A | 21998 | 0.36 | 1.90 | 24564 | 0.31 | 1.20 | 92 |
| 1 | VAFIIFWVR | K29R | 20045 | 0.40 | 1.20 | 5746 | 0.94 | 0.70 | 100 |

TABLE 2B-continued

In Silico and In Vitro MHC binding of Variant Peptides

| Overlapping Reference Peptide | Peptide Sequence | Mutation | A*11:01 IEDB IC50 | A*11:01 In Silico Score | A*11:01 In Vitro Score | B*08:01 IEDB IC50 | B*08:01 In Silico Score | B*08:01 In Vitro Score | SEQ ID NO. |
|---|---|---|---|---|---|---|---|---|---|
| 3 | FIIFWVHRG | K29H | 19850 | 0.40 | 0.90 | 17464 | 0.46 | 0.20 | 39 |
| 4 | IIFWVHRGR | K29H | 196 | 2.41 | 77.50 | 22662 | 0.34 | 0.20 | 40 |
| 5 | IFWVHRGRK | K29H | 7133 | 0.85 | 36.60 | 22030 | 0.36 | 0.10 | 41 |
| 6 | FWVHRGRKK | K29H | 22214 | 0.35 | 5.60 | 23778 | 0.32 | 0.00 | 42 |
| 7 | WVHRGRKKL | K29H | 23844 | 0.32 | 5.60 | 814 | 1.79 | 19.20 | 43 |
| 1 | VAFIIFWVA | K29A | 12499 | 0.60 | 2.80 | 5131 | 0.99 | 0.00 | 44 |
| 2 | AFIIFWVAR | K29A | 2784 | 1.25 | 51.80 | 21850 | 0.36 | 0.20 | 45 |
| 3 | FIIFWVARG | K29A | 20922 | 0.38 |  | 18463 | 0.43 |  | 102 |
| 4 | IIFWVARGR | K29A | 239 | 2.32 | 70.60 | 23580 | 0.33 | 0.30 | 46 |
| 5 | IFWVARGRK | K29A | 8772 | 0.76 | 34.90 | 23612 | 0.33 | 0.00 | 47 |
| 6 | FWVARGRKK | K29A | 20762 | 0.38 | 8.90 | 23035 | 0.34 | 0.00 | 48 |
| 7 | WVARGRKKL | K29A | 23920 | 0.32 | 13.80 | 2821 | 1.25 | 32.40 | 49 |
| 1 | VAFIIFWVQ | K29Q | 15477 | 0.51 | 3.90 | 14875 | 0.53 | 0.20 | 50 |
| 2 | AFIIFWVQR | K29Q | 2174 | 1.36 | 15.00 | 23016 | 0.34 | 0.00 | 51 |
| 3 | FIIFWVQRG | K29Q | 22161 | 0.35 | 1.50 | 17653 | 0.45 | 0.60 | 52 |
| 4 | IIFWVQRGR | K29Q | 361 | 2.14 | 72.80 | 23548 | 0.33 | 0.10 | 53 |
| 5 | IFWVQRGRK | K29Q | 9561 | 0.72 | 128.50 | 23670 | 0.32 | 0.00 | 54 |
| 6 | FWVQRGRKK | K29Q | 22394 | 0.35 | 5.70 | 22604 | 0.34 | 1.90 | 55 |
| 7 | WVQRGRKKL | K29Q | 23688 | 0.32 | 12.80 | 2512 | 1.30 | 45.10 | 56 |
| 4 | IIFWVKRGS | R32S | 18923 | 0.42 | 100.00 | 22325 | 0.35 | 0.40 | 57 |
| 5 | IFWVKRGSK | R32S | 7476 | 0.83 | 47.90 | 21691 | 0.36 | 1.20 | 58 |
| 6 | FWVKRGSKK | R32S | 19910 | 0.40 | 5.60 | 20823 | 0.38 | 0.10 | 59 |
| 7 | WVKRGSKKL | R32S | 24090 | 0.32 | 11.80 | 585 | 1.93 | 56.10 | 60 |
| 4 | IIFWVKRGL | R32L | 20182 | 0.39 | 32.40 | 17368 | 0.46 | 1.70 | 61 |
| 5 | IFWVKRGLK | R32L | 4201 | 1.08 | 61.10 | 23537 | 0.33 | 58.30 | 62 |
| 6 | FWVKRGLKK | R32L | 17309 | 0.46 | 25.30 | 20839 | 0.38 | 6.30 | 63 |
| 7 | WVKRGLKKL | R32L | 24095 | 0.32 | 22.10 | 765 | 1.82 | 65.70 | 64 |
| 4 | IIFWVKRGH | R32H | 7117 | 0.85 | 19.50 | 23227 | 0.33 | 0.10 | 65 |
| 5 | IFWVKRGHK | R32H | 10783 | 0.67 | 30.90 | 23461 | 0.33 | 3.20 | 66 |
| 6 | FWVKRGHKK | R32H | 17635 | 0.45 | 27.60 | 20754 | 0.38 | 0.40 | 67 |
| 7 | WVKRGHKKL | R32H | 23924 | 0.32 | 2.80 | 269 | 2.27 | 47.60 | 68 |
| 4 | IIFWVKRGA | R32A | 19134 | 0.42 | 22.60 | 19585 | 0.41 | 0.90 | 69 |
| 5 | IFWVKRGAK | R32A | 8311 | 0.78 | 69.70 | 21592 | 0.36 | 2.20 | 70 |
| 6 | FWVKRGAKK | R32A | 20234 | 0.39 | 13.20 | 21762 | 0.36 | 0.30 | 71 |
| 7 | WVKRGAKKL | R32A | 23857 | 0.32 | 4.60 | 1366 | 1.56 | 34.10 | 72 |
| 4 | IIFWVKRGN | R32N | 19351 | 0.41 | 42.10 | 22864 | 0.34 | 0.90 | 73 |

TABLE 2B-continued

In Silico and In Vitro MHC binding of Variant Peptides

| Overlapping Reference Peptide | Peptide Sequence | Mutation | A*11:01 IEDB IC50 | A*11:01 In Silico Score | A*11:01 In Vitro Score | B*08:01 IEDB IC50 | B*08:01 In Silico Score | B*08:01 In Vitro Score | SEQ ID NO. |
|---|---|---|---|---|---|---|---|---|---|
| 5 | IFWVKRGNK | R32N | 6780 | 0.87 | 45.90 | 24238 | 0.31 | 0.10 | 74 |
| 6 | FWVKRGNKK | R32N | 20732 | 0.38 | 7.30 | 21565 | 0.37 | 0.10 | 75 |
| 7 | WVKRGNKKL | R32N | 24036 | 0.32 | 4.10 | 1181 | 1.63 | 65.90 | 76 |
| 4 | IIFWVQRGS | K29Q/R32S | 18031 | 0.44 | 16.90 | 22961 | 0.34 | 0.10 | 77 |
| 5 | IFWVQRGSK | K29Q/R32S | 7300 | 0.84 | 103.30 | 22846 | 0.34 | 0.00 | 78 |
| 6 | FWVQRGSKK | K29Q/R32S | 20419 | 0.39 | 6.80 | 21853 | 0.36 | 0.00 | 79 |
| 7 | WVQRGSKKL | K29Q/R32S | 23740 | 0.32 | 5.90 | 5230 | 0.98 | 6.80 | 80 |
| 4 | IIFWVQRGA | K29Q/R32A | 18055 | 0.44 | 56.50 | 20759 | 0.38 | 0.20 | 81 |
| 5 | IFWVQRGAK | K29Q/R32A | 8237 | 0.78 | 61.30 | 22801 | 0.34 | 0.20 | 82 |
| 6 | FWVQRGAKK | K29Q/R32A | 20696 | 0.38 | 18.30 | 22612 | 0.34 | 0.00 | 83 |
| 7 | WVQRGAKKL | K29Q/R32A | 23552 | 0.33 | 3.80 | 8314 | 0.78 | 11.40 | 84 |
| 4 | IIFWVQRGN | K29Q/R32N | 18437 | 0.43 | 29.00 | 23425 | 0.33 | 0.00 | 85 |
| 5 | IFWVQRGNK | K29Q/R32N | 6566 | 0.88 | 67.50 | 24059 | 0.32 | 0.10 | 86 |
| 6 | FWVQRGNKK | K29Q/R32N | 21228 | 0.37 | 5.90 | 22436 | 0.35 | 0.00 | 87 |
| 7 | WVQRGNKKL | K29Q/R32N | 23751 | 0.32 | 10.70 | 7869 | 0.80 | 32.00 | 88 |
| 7 | WVKRGRKKS | L35S | 23906 | 0.32 | 6.70 | 10345 | 0.68 | 4.30 | 89 |
| 7 | WVKRGRKKA | L35A | 23864 | 0.32 | 3.10 | 1225 | 1.61 | 3.10 | 90 |
| 7 | WVQRGNKKS | K29Q/L35S | 23612 | 0.33 | 5.00 | 21235 | 0.37 | 0.00 | 91 |
| 7 | WVQRGNKKA | K29Q/L35A | 23576 | 0.33 | 0.80 | 14247 | 0.55 | 0.70 | 92 |
| 1 | VAFIIFWVR | K29R | 108 | 2.67 | 34.60 | 16290 | 0.49 | 0.10 | 100 |
| 2 | AFIIFWVRR | K29R | 3387 | 1.17 | 1.50 | 22717 | 0.34 | 0.30 | 101 |

Example 4

Analysis of Peptides Derived from Junction Region of a CAR for Binding to HLA-A2:01

In order to identify CAR-derived peptides potentially capable of inducing immunogenic responses, a series of overlapping peptides within the non-variant (reference) sequence containing the junction between the CD28 transmembrane domain and 4-1BB costimulatory domain of a CAR were assessed in silico. Algorithms were used to predict binding affinities for the peptide groove of a common human MHC class I molecule (HLA-A2:01) using in silico analysis to predict affinity for binding. As set forth in FIG. 3, the assessed portion of the CAR had the sequence CYSLLVTVAFIIFWVKRGRKKLLYIFKQPF (set forth in SEQ ID NO: 6), which contains a portion of the of the CD28 transmembrane domain (set forth in SEQ ID NO:2) and a portion of the 4-1BB costimulatory domain (set forth in SEQ ID NO:3), with the residues spanning the junction of the domains shown by underline. Predicted HLA-A2:01 binding affinity was assessed in silico for a series of 140 overlapping peptides of 8-14 amino acids of the sequence set forth in SEQ ID NO:6. Thirty-five (35) of the peptides contained only sequence from the transmembrane domain portion; 35 of the peptides contained only from the costimulatory domain portion, and 70 of the peptides had a junction or fusion region sequence, containing amino acid residues bridging the junction between the domains. For this assessment, peptide fragments predicted to bind to HLA-A2:01 with a dissociation constant of 0 nM to 50 nM were considered predicted to bind with high affinity. Peptide fragments predicted to bind with a dissociation constant of 51 nM to 1000 nM were considered predicted to bind with low affinity. Peptide fragments predicted to bind with a predicted affinity of 1000 nM to 5000 nM were considered predicted to bind with rare affinity. The results are presented in FIG. 3.

Figure 3:
FIG. 3 shows an epitope affinity map for predicted binding affinities of peptides of an exemplary region of a chimeric receptor for binding to HLA-A2:01, including a series of overlapping 8mer to 14mer peptides of an exemplary junction region having an amino acid sequence CYS-LLVTVAFIIFWVKRGRKKLLYIFKQPF (SEQ ID NO: 6) where residues 1-15 correspond to an exemplary CD28 transmembrane domain and residues 16-30 correspond to an exemplary 4-1BB costimulatory domain. The figure also depicts predicted binding affinities of a series of overlapping 8mer to 14mer peptides of a variant junction region having an amino acid sequence CYSLLVTVAFIIFWNNVKR-GRKKLLYIFKQPF (SEQ ID NO: 13), containing inserted asparagine residues between the CD28 transmembrane domain and 4-1BB costimulatory domain.

As shown in FIG. 3, two of the peptides derived from the reference sequence in this region, each containing a sequence with an overlapping region spanning the junction between the domains were predicted to exhibit low binding affinity for HLA-A2:01. Specifically, a 14-mer peptide having the sequence FIIFWVKRGRKKLL (SEQ ID NO: 10), was predicted to bind with a dissociation constant of 294 nM, and a 13-mer peptide having the sequence of FIIFWVKRGRKKL (SEQ ID NO: 11) was predicted to bind with a dissociation constant of 618 nM. These peptides each included a portion of the 15-mer peptide set forth in SEQ ID NO:1 and identified in Example 1. Shorter 8-mer to 12-mer peptides within this sequence were not predicted to exhibit binding to HLA-A2:01. Another 13-mer peptide containing the amino acid sequence IIFWVKRGRKKLL (SEQ ID NO: 12) was predicted to have a rare binding affinity with a predicted dissociation constant of approximately 3000 nM. None of the remaining fragments that bridged the junction between the two domains were predicted by this assay to exhibit binding affinity for HLA-A2:01 (all had a predicted dissociation constant of far greater than 5000 nM, and in most cases higher than 14,000 nm or 20,000 nM or greater). In each of the peptides predicted to bind to HLA-A2:01, neither of the two junction-spanning residues (VK) themselves was predicted to be an anchor residue; rather, such peptides contained these residues in non-flanking positions.

Approximately 15 of the peptides containing sequence derived only from the transmembrane domain were predicted to have a dissociation constant for HLA-A2:01 of less than 5000 nM. Two peptides containing sequence only from the co-stimulatory domain were predicted to have a dissociation constant for HLA-A2:01 binding of less than 5000 nM. The costimulatory domain and transmembrane domain in the assessed sequence are derived from endogenous human sequences, which generally are less likely to be immunogenic to a human subject. For example, in the study described in Example 1, no immune responses were detected that were specific for peptide sequences solely within either one of these domains of the CAR. Accordingly, variants of peptides containing sequence spanning the junction region were assessed.

To generate variant peptides predicted to have reduced binding affinities to HLA-A2:01 and/or reduced immunogenicity in a human subject having this HLA allele, a variant sequence was generated in silico, containing mutations in the junction region as compared to the sequence set forth in SEQ ID NO:6. Given that peptides containing the junction-spanning "VK" residues (at non-anchor positions) were predicted to exhibit high binding affinities for HLA-A2:01, two asparagine residues were inserted in the junction between the CD28 transmembrane and 4-1BB co-stimulatory domains. The variant contained the sequence CYSLLVTVAFIIFWVNNKRGRKKLLYIFKQPF (set forth in SEQ ID NO: 13, the sequence flanking the junction that was generated by insertion of the asparagine residues is shown in underline). The exemplary variant sequence of SEQ ID NO: 13 was assessed by the same predictive methods. To assess predicted binding affinities for this variant sequence, a series of 154 overlapping fragments of 8-14 amino acids of the sequence set forth in SEQ ID NO: 13 were assessed by in silico analysis as described above, whereby 35 peptides had a sequence only in the transmembrane portion, 35 peptides had a sequence only in the costimulatory domain portion and 84 peptides contained a junction region sequence containing amino acids bridging the domains, including one or both of the inserted asparagine residues.

The results are depicted in FIG. 3. As shown, overall, the HLA-A2:01 binding affinities of overlapping peptides within the variant region containing the junction, collectively, were substantially reduced as compared to the non-variant sequence. In particular, the predicted dissociation constant for binding to HLA-A2:01 of peptides in the portion of the junction region previously predicted to be immunogenic was substantially reduced. For example, peptide variants IIFWVNNKRGRKKL (SEQ ID NO: 14) and IIFWVNNKRGRKK (SEQ ID NO: 15), which included altered flanking residues compared to peptides identified as set forth in SEQ ID NOS:10 and 11, respectively, were predicted to exhibit no detectable binding affinity to HLA-A2:01. Two 14-mer peptides, FIIFWVNNKRGRKK (SEQ ID NO:11) and IFWVNNKRGRKKLL (SEQ ID NO:12), were predicted to exhibit a dissociation constant for binding to this HLA indicating a rare binding affinity, within the range of 1000 nM to 5000 nM. All other peptides containing the modified junction region sequence were predicted to exhibit a dissociation constant of greater than 5000 nM, and in most cases higher than 14,000 nM or 20,000 nM or greater, and thus were not predicted to exhibit binding affinity for HLA-A2:01 by this assessment. Additionally, the modification of the junction region sequence did not create any new peptides predicted to have higher binding affinities for HLA-A2:01 within the costimulatory or transmembrane domain regions.

Example 5

Administration of Anti-CD22 CAR-Expressing Cells to Subjects Previously Treated with Anti-CD19 CAR Six subjects with relapsed/refractory CD22$^+$ B cell acute lymphoblastic leukemia (ALL) were administered autologous T cells expressing an anti-CD22 chimeric antigen receptor (CAR). The CAR included a human anti-CD22 scFv antibody, a CD8alpha transmembrane domain, a 4-1BB intracellular signaling domain, and a CD3zeta intracellular signaling domain.

All subjects had previously undergone at least one prior allogeneic hematopoietic stem cell transplant and had received treatment with one of various CD19-directed CAR-T cell therapies. Five of the subjects had relapsed with ALL on which CD19 was not detected ("CD19 neg") and one subject was otherwise a non-responder to the prior CD19 CAR therapy.

Table 3 summarizes the characteristics of the treated patients.

TABLE 3

Patient Characteristics

| ID | Age/Sex | Prior HCT | Prior anti-CD19 CAR | CD19 neg relapse | CD22 site density | Pre-HCT disease burden (% leukemia in aspirate) |
| --- | --- | --- | --- | --- | --- | --- |
| 1 | 22/M | Y | Y | Y | 2084 | >95% |
| 2 | 20/F | Y (2) | Y | Y | 13452 | 5% |
| 3 | 22/M | Y | Y | Y | 846 | >90% |
| 4 | 22/M | Y | Y | N | 2589 | 95% |
| 5 | 7/F | Y | Y | Y | 2839 | 32% |
| 6 | 17/F | Y | Y | Y | 2185 | 1% |

HCT: hematopoietic cell transplantation.

Prior to administration of the cells, patients underwent autologous leukapheresis to harvest peripheral blood mononuclear cells (PBMCs). T cells were isolated from the harvested PBMCs by immunoaffinity-based enrichment for CD3 expression and cultured in the presence of anti-CD3/-CD28 beads, followed by transduction with a lentiviral vector encoding the anti-CD22 CAR. The cells were cultured for 7-10 days. Subjects received induction chemotherapy with 25 mg/m$^2$ fludarabine on Days −4, −3 and −2 and 900 mg/m² cyclophosphamide on day −2 (cell infusion on Day 0). Each patient received an initial CAR T cell dose of 3×10⁵ transduced T-cells/recipient weight (kg) by intravenous infusion. The second subject enrolled developed grade 3 diarrhea, meeting the criteria for dose-limiting toxicity (DLT), which led to dose expansion at the first dose-level to treat a total of 6 subjects. No subsequent DLTs were seen at this dosage. Two subjects developed grade 1 cytokine release syndrome (CRS), one subject developed grade 2 CRS, and in two subjects CRS was not present.

The number of CAR-T cells in peripheral blood, bone marrow or cerebrospinal fluid was determined at certain timepoints post-treatment by incubating cells with CD22-Fc. For patients in which expansion was observed, evidence for CAR-T cell expansion was seen in peripheral blood, bone marrow and cerebrospinal fluid, beginning at about day 7. The maximum or peak CAR-T cell expansion was generally observed between about day 12 and about day 15 post-infusion. Table 7 sets forth the maximum or peak percentage of anti-CD22 CAR-T cells observed in this assessment period as a percentage of total T cells in each sample for the treated subjects. Clinical responses were evaluated at day 28 (+/−4 days) post-infusion.

As shown in Table 4, the results were consistent with responses being generally correlated to degree of CAR-T cell expansion. For three subjects that exhibited no or low CAR-T cell expansion also showed evidence of disease progression. Two other subjects had stable disease, and one was observed with complete remission with no MRD. Flow cytometric CAR persistence was detected out to 47 days post-infusion in this subject, with remission maintained for 3 months post-infusion. The results demonstrate safe, feasible, and clinically active anti-CD22 CAR T-cell therapy in subjects having undergone (and having become non-responsive to, e.g., due to epitope/antigen loss) previous anti-CD19 CAR therapy.

TABLE 4

Treatment response

| ID | Maximum CAR expansion (flow) | | | CRS | Best Response |
| | PB | Marrow | CSF | | |
|---|---|---|---|---|---|
| 1 | 0 | 0 | n/a | None | PD |
| 2 | 52.3% | 19.5% | 0% | Gr 1 | MRD neg CR |
| 3 | 73% | 36% | 32% | Gr 1 | SD |
| 4 | 6% | 1% | 0% | Gr 2 | SD |
| 5 | 0% | 1.3% | 0% | None | PD |
| 6 | 1.8% | 2% | 0% | None | PD |

PB: peripheral blood;
CSF: cerebrospinal fluid;
CRS: cytokine release syndrome;
PD: progressive disease;
MRD: minimal residual disease;
CR: complete remission;
SD: stable disease.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 5

Sequences

| SEQ ID NO | Sequence | Note |
|---|---|---|
| 1 | ESKYGPPCPPCP | IgG4 hinge |
| 2 | FWVLVVVGGVLACYSLLVTVAFIIFWV | CD28 transmembrane domain |
| 3 | KRGRKKLLYIFKQPFMRPVQTTQEEDGCSCRFPEEEEGGCEL | 4-1BB costimulatory domain (amino acids 214-255 of Q07011.1) Homo sapien |
| 4 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3-zeta intracellular signaling domain |
| 5 | FWVLVVVGGVLACYSLLVTVAFIIFWV<u>KR</u>GRKKLLYIFKQPFMRPVQTTQEEDGCSCRFPEEEEGGCEL | CD28-4-1BB |
| 6 | CYSLLVTVAFIIFWVKRGRKKLLYIFKQPF | Peptide |
| 7 | VAFIIFWVKRGRKKLL | Peptide |
| 8 | AFIIFWVKRGRKKLL | Peptide |
| 9 | FWVKRGRKKLLYIFK | Peptide |
| 10 | FIIFWVKRGRKKLL | Peptide |
| 11 | FIIFWVKRGRKKL | Peptide |
| 12 | IIFWVKRGRKKLL | Peptide |

TABLE 5 -continued

Sequences

| SEQ ID NO | Sequence | Note |
|---|---|---|
| 13 | CYSLLVTVAFIIFWVNNKRGRKKLLYIFKQPF | Variant junction region |
| 14 | IIFWVNNKRGRKKL | Variant peptide |
| 15 | IIFWVNNKRGRKK | Variant peptide |
| 16 | VAFIIFWVK | Synthetic peptide |
| 17 | AFIIFWVKR | Synthetic peptide |
| 18 | FIIFWVKRG | Synthetic peptide |
| 19 | IIFWVKRGR | Synthetic peptide |
| 20 | IFWVKRGRK | Synthetic peptide |
| 21 | FWVKRGRKK | Synthetic peptide |
| 22 | WVKRGRKKL | Synthetic peptide |
| 23 | VAFIIFWVS | Synthetic peptide K28S |
| 24 | AFIIFWVSR | Synthetic peptide K28S |
| 25 | FIIFWVSRG | Synthetic peptide K28S |
| 26 | IIFWVSRGR | Synthetic peptide K28S |
| 27 | IFWVSRGRK | Synthetic peptide K28S |
| 28 | FWVSRGRKK | Synthetic peptide K28S |
| 29 | WVSRGRKKL | Synthetic peptide K28S |
| 30 | VAFIIFWVL | Synthetic peptide K28L |
| 31 | AFIIFWVLR | Synthetic peptide K28L |
| 32 | FIIFWVLRG | Synthetic peptide K28L |
| 33 | IIFWVLRGR | Synthetic peptide K28L |
| 34 | IFWVLRGRK | Synthetic peptide K28L |
| 35 | FWVLRGRKK | Synthetic peptide K28L |
| 36 | WVLRGRKKL | Synthetic peptide K28L |
| 37 | VAFIIFWVH | Synthetic peptide K28H |
| 38 | AFIIFWVHR | Synthetic peptide K28H |
| 39 | FIIFWVHRG | Synthetic peptide K28H |
| 40 | IIFWVHRGR | Synthetic peptide K28H |

TABLE 5-continued

Sequences

| SEQ ID NO | Sequence | Note |
|---|---|---|
| 41 | IFWVHRGRK | Synthetic peptide K28H |
| 42 | FWVHRGRKK | Synthetic peptide K28H |
| 43 | WVHRGRKKL | Synthetic peptide K28H |
| 44 | VAFIIFWVA | Synthetic peptide K28A |
| 45 | AFIIFWVAR | Synthetic peptide K28A |
| 46 | IIFWVARGR | Synthetic peptide K28A |
| 47 | IFWVARGRK | Synthetic peptide K28A |
| 48 | FWVARGRKK | Synthetic peptide K28A |
| 49 | WVARGRKKL | Synthetic peptide K28A |
| 50 | VAFIIFWVQ | Synthetic peptide K28Q |
| 51 | AFIIFWVQR | Synthetic peptide K28Q |
| 52 | FIIFWVQRG | Synthetic peptide K28Q |
| 53 | IIFWVQRGR | Synthetic peptide K28Q |
| 54 | IFWVQRGRK | Synthetic peptide K28Q |
| 55 | FWVQRGRKK | Synthetic peptide K28Q |
| 56 | WVQRGRKKL | Synthetic peptide K28Q |
| 57 | IIFWVKRGS | Synthetic peptide R31S |
| 58 | IFWVKRGSK | Synthetic peptide R31S |
| 59 | FWVKRGSKK | Synthetic peptide R31S |
| 60 | WVKRGSKKL | Synthetic peptide R31S |
| 61 | IIFWVKRGL | Synthetic peptide R31L |
| 62 | IFWVKRGLK | Synthetic peptide R31L |
| 63 | FWVKRGLKK | Synthetic peptide R31L |
| 64 | WVKRGLKKL | Synthetic peptide R31L |
| 65 | IIFWVKRGH | Synthetic peptide R31H |

TABLE 5-continued

Sequences

| SEQ ID NO | Sequence | Note |
|---|---|---|
| 66 | IFWVKRGHK | Synthetic peptide R31H |
| 67 | FWVKRGHKK | Synthetic peptide R31H |
| 68 | WVKRGHKKL | Synthetic peptide R31H |
| 69 | IIFWVKRGA | Synthetic peptide R31A |
| 70 | IFWVKRGAK | Synthetic peptide R31A |
| 71 | FWVKRGAKK | Synthetic peptide R31A |
| 72 | WVKRGAKKL | Synthetic peptide R31A |
| 73 | IIFWVKRGN | Synthetic peptide R31N |
| 74 | IFWVKRGNK | Synthetic peptide R31N |
| 75 | FWVKRGNKK | Synthetic peptide R31N |
| 76 | WVKRGNKKL | Synthetic peptide R31N |
| 77 | IIFWVQRGS | Synthetic peptide K28Q/R31S |
| 78 | IFWVQRGSK | Synthetic peptide K28Q/R31S |
| 79 | FWVQRGSKK | Synthetic peptide K28Q/R31S |
| 80 | WVQRGSKKL | Synthetic peptide K28Q/R31S |
| 81 | IIFWVQRGA | Synthetic peptide K28Q/R31A |
| 82 | IFWVQRGAK | Synthetic peptide K28Q/R31A |
| 83 | FWVQRGAKK | Synthetic peptide K28Q/R31A |
| 84 | WVQRGAKKL | Synthetic peptide K28Q/R31A |
| 85 | IIFWVQRGN | Synthetic peptide K28Q/R31N |
| 86 | IFWVQRGNK | Synthetic peptide K28Q/R31N |
| 87 | FWVQRGNKK | Synthetic peptide K28Q/R31N |
| 88 | WVQRGNKKL | Synthetic peptide K28Q/R31N |
| 89 | WVKRGRKKS | Synthetic peptide L34S |
| 90 | WVKRGRKKA | Synthetic peptide L34A |

TABLE 5 -continued

Sequences

| SEQ ID NO | Sequence | Note |
|---|---|---|
| 91 | WVQRGNKKS | Synthetic peptide K28Q/L34S |
| 92 | WVQRGNKKA | Synthetic peptide K28Q/L34A |
| 93 | MGNSCYNIVATLLLVLNFERTRSLQDPCSNCPAGTFCDNNRNQICSPCP PNSFSSAGGQRTCDICRQCKGVFRTRKECSSTSNAECDCTPGFHCLGAG CSMCEQDCKQGQELTKKGCKDCCFGTFNDQKRGICRPWTNCSLDGKSVL VNGTKERDVVCGPSPADLSPGASSVTPPAPAREPGHSPQIISFFLALTS TALLFLLFFLTLRFSVVKRGRKKLLYIFKQPFMRPVQTTQEEDGCSCRF PEEEEGGCEL | 4-1BB costimulatory domain (Accession No. Q07011.1) Homo sapien |
| 94 | MGNSCYNIVATLLLVLNFERTRSLQDPCSNCPAGTFCDNNRNQICSPCP PNSFSSAGGQRTCDICRQCKGVFRTRKECSSTSNAECDCTPGFHCLGAG CSMCEQDCKQGQELTKKGCKDCCFGTFNDQKRGICRPWTNCSLDGKSVL VNGTKERDVVCGPSPADLSPGASSVTPPAPAREPGHSPQIISFFLALTS TALLFLLFFLTLRFSVVKRGRKKLLYIFKQPFMRPVQTTQEEDGCSCRF PEEEEGGCEL | CD28 transmembrane domain (Accession No. P10747) Homo sapien |
| 95 | MKWKALFTAAILQAQLPITEAQSFGLLDPKLCYLLDGILFIYGVILTAL FLRVKFSRSADAPAYQQGQNQLYNELNLGRREEYDVLDKRRGRDPEMGG KPQRRKNPQEGLYNELQKDKMAEAYSEIGMKGERRRGKGHDGLYQGLST ATKDTYDALHMQALPPR | CD3 zeta chain (Accession No. P20963) Homo sapien |
| 96 | FIIFWVNNKRGRKK | Synthetic peptide |
| 97 | IFWVNNKRGRKKLL | Synthetic peptide |
| 98 | FIIFWVNNKRGRKK | Synthetic peptide |
| 99 | IFWVNNKRGRKKLL | Synthetic peptide |
| 100 | VAFIIFWVR | Synthetic peptide K28R |
| 101 | AFIIFWVRR | Synthetic peptide K28R |
| 102 | FIIFWVARG | Synthetic peptide K28A |
| 103 | MFWVLVVVGGVLACYSLLVTVAFIIFWV | CD28 transmembrane domain (amino acids 153-179 of Accession No. P10747) Homo sapien |
| 104 | IEVMYPPPYLDNEKSNGTIIHVKGKHLCPSPLFPGPSKPFWVLVVVGGV LACYSLLVTVAFIIFWV | CD28, including transmembrane (amino acids 114-179 of Accession No. P10747) Homo sapien |
| 105 | RVKFSRSAEPPAYQQGQNQLYNELNLGRREEYDVLDKRRGRDPEMGGKP RRKNPQEGLYNELQKDKMAEAYSEIGMKGERRRGKGHDGLY QGLSTATKDTYDALHMQALPPR | CD3 zeta Homo sapien |
| 106 | GAATCTAAGTACGGACCGCCCTGCCCCCCTTGCCCT | spacer (IgG4hinge) (nt) homo sapien |
| 107 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer Homo sapien |
| 108 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2-CH3 spacer Homo sapien |
| 109 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC | IgD-hinge-Fc Homo sapien |

TABLE 5 -continued

Sequences

| SEQ ID NO | Sequence | Note |
|---|---|---|
| | EVSGFSPPNILLMWLEDQREVNTSGFAPARPPPQPGSTTFWAWSVLRVP APPSPQPATYTCVVSHEDSRTLLNASRSLEVSYVTDH | |
| 110 | LEGGGEGRGSLLTCGDVEENPGPR | T2A artificial |
| 111 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR artificial |
| 112 | RSKRSRLLHSDYMNMTPRRPGPTRKHYQPYAPPRDFAAYRS | CD28 cytoplasmic domain (amino acids 180-220 of P10747) *Homo sapien* |
| 113 | RSKRSRGGHSDYMNMTPRRPGPTRKHYQPYAPPRDFAAYRS | CD28 cytoplasmic domain variant (LL to GG) *Homo sapien* |
| 114 | FWVLVVVGGVLACYSLLVTVAFIIFWVARGRKKLLYIFKQPFMRPVQTT QEEDGCSCRFPEEEEGGCEL | CD28-4-1BB K28A variant |
| 115 | FWVLVVVGGVLACYSLLVTVAFIIFWVHRGRKKLLYIFKQPFMRPVQTT QEEDGCSCRFPEEEEGGCEL | CD28-4-1BB K28H variant |
| 116 | FWVLVVVGGVLACYSLLVTVAFIIFWVLRGRKKLLYIFKQPFMRPVQTT QEEDGCSCRFPEEEEGGCEL | CD28-4-1BB K28L variant |
| 117 | FWVLVVVGGVLACYSLLVTVAFIIFWVQRGRKKLLYIFKQPFMRPVQTT QEEDGCSCRFPEEEEGGCEL | CD28-4-1BB K28Q variant |
| 118 | FWVLVVVGGVLACYSLLVTVAFIIFWVSRGRKKLLYIFKQPFMRPVQTT QEEDGCSCRFPEEEEGGCEL | CD28-4-1BB K28S variant |
| 119 | FWVLVVVGGVLACYSLLVTVAFIIFWVKRGAKKLLYIFKQPFMRPVQTT QEEDGCSCRFPEEEEGGCEL | CD28-4-1BB R31A variant |
| 120 | FWVLVVVGGVLACYSLLVTVAFIIFWVKRGHKKLLYIFKQPFMRPVQTT QEEDGCSCRFPEEEEGGCEL | CD28-4-1BB R31H variant |
| 121 | FWVLVVVGGVLACYSLLVTVAFIIFWVKRGLKKLLYIFKQPFMRPVQTT QEEDGCSCRFPEEEEGGCEL | CD28-4-1BB R31L variant |
| 122 | FWVLVVVGGVLACYSLLVTVAFIIFWVKRGNKKLLYIFKQPFMRPVQTT QEEDGCSCRFPEEEEGGCEL | CD28-4-1BB R31N variant |
| 123 | FWVLVVVGGVLACYSLLVTVAFIIFWVKRGRKKALYIFKQPFMRPVQTT QEEDGCSCRFPEEEEGGCEL | CD28-4-1BB L34A variant |
| 124 | FWVLVVVGGVLACYSLLVTVAFIIFWVKRGRKKSLYIFKQPFMRPVQTT QEEDGCSCRFPEEEEGGCEL | CD28-4-1BB L34S variant |
| 125 | FWVLVVVGGVLACYSLLVTVAFIIFWVQRGAKKLLYIFKQPFMRPVQTT QEEDGCSCRFPEEEEGGCEL | CD28-4-1BB K28Q/R31A variant |
| 126 | FWVLVVVGGVLACYSLLVTVAFIIFWVQRGNKKLLYIFKQPFMRPVQTT QEEDGCSCRFPEEEEGGCEL | CD28-4-1BB K28Q/R31N variant |
| 127 | FWVLVVVGGVLACYSLLVTVAFIIFWVQRGSKKLLYIFKQPFMRPVQTT QEEDGCSCRFPEEEEGGCEL | CD28-4-1BB K28Q/R31S variant |
| 128 | FWVLVVVGGVLACYSLLVTVAFIIFWVQRGRKKALYIFKQPFMRPVQTT QEEDGCSCRFPEEEEGGCEL | CD28-4-1BB K28Q/L34A variant |
| 129 | FWVLVVVGGVLACYSLLVTVAFIIFWVQRGRKKSLYIFKQPFMRPVQTT QEEDGCSCRFPEEEEGGCEL | CD28-4-1BB K28Q/L34S variant |

TABLE 5 -continued

Sequences

| SEQ ID NO | Sequence | Note |
|---|---|---|
| 130 | FWVLVVVGGVLACYSLLVTVAFIIFW<u>VK</u>RG<u>N</u>KK<u>A</u>LYIFKQPFMRPVQTTQEEDGCSCRFPEEEEGGCEL | CD28-4-1BB R31N/L34A variant |
| 131 | FWVLVVVGGVLACYSLLVTVAFIIFW<u>VK</u>RG<u>N</u>KK<u>S</u>LYIFKQPFMRPVQTTQEEDGCSCRFPEEEEGGCEL | CD28-4-1BB R31N/L34S variant |
| 132 | FWVLVVVGGVLACYSLLVTVAFIIFW<u>VQ</u>RG<u>N</u>KK<u>A</u>LYIFKQPFMRPVQTTQEEDGCSCRFPEEEEGGCEL | CD28-4-1BB K28Q/R31N/L34A variant |
| 133 | FWVLVVVGGVLACYSLLVTVAFIIFW<u>VQ</u>RG<u>N</u>KK<u>S</u>LYIFKQPFMRPVQTTQEEDGCSCRFPEEEEGGCEL | CD28-4-1BB K28Q/R31N/L34S variant |
| 134 | FWVLVVVGGVLACYSLLVTVAFIIFW<u>VNNK</u>RGRKKLLYIFKQPFMRPVQTTQEEDGCSCRFPEEEEGGCEL | CD28-4-1BB with variant junction region with NN insertion |
| 135 | MFWVLVVVGGVLACYSLLVTVAFIIFWVKRGRKKLLYIFKQPFMRPVQTTQEEDGCSCRFPEEEEGGCEL | CD28-4-1BB |
| 136 | IEVMYPPPYLDNEKSNGTIIHVKGKHLCPSPLFPGPSKPFWVLVVVGGVLACYSLLVTVAFIIFWVKRGRKKLLYIFKQPFMRPVQTTQEEDGCSCRFPEEEEGGCEL | CD28-4-1BB |
| 137 | SLLVTVAFIIFW<u>VK</u>RGRKKLLYIFKQ | CD28-4-1BB junction region |
| 138 | SLLVTVAFIIFW<u>VA</u>RGRKKLLYIFKQ | CD28-4-1BB junction region K14A variant |
| 139 | SLLVTVAFIIFW<u>VH</u>RGRKKLLYIFKQ | CD28-4-1BB junction region K14H variant |
| 140 | SLLVTVAFIIFW<u>VL</u>RGRKKLLYIFKQ | CD28-4-1BB junction region K14L variant |
| 141 | SLLVTVAFIIFW<u>VQ</u>RGRKKLLYIFKQ | CD28-4-1BB junction region K14Q variant |
| 142 | SLLVTVAFIIFW<u>VS</u>RGRKKLLYIFKQ | CD28-4-1BB junction region K14S variant |
| 143 | SLLVTVAFIIFW<u>VK</u>RG<u>A</u>KKLLYIFKQ | CD28-4-1BB junction region R17A variant |
| 144 | SLLVTVAFIIFW<u>VK</u>RG<u>H</u>KKLLYIFKQ | CD28-4-1BB junction region R17H variant |
| 145 | SLLVTVAFIIFW<u>VK</u>RG<u>L</u>KKLLYIFKQ | CD28-4-1BB junction region R17L variant |
| 146 | SLLVTVAFIIFW<u>VK</u>RG<u>N</u>KKLLYIFKQ | CD28-4-1BB junction region R17N variant |
| 147 | SLLVTVAFIIFW<u>VK</u>RGRKK<u>A</u>LYIFKQ | CD28-4-1BB junction region L20A variant |
| 148 | SLLVTVAFIIFW<u>VK</u>RGRKK<u>S</u>LYIFKQ | CD28-4-1BB junction region L20S variant |
| 149 | SLLVTVAFIIFW<u>VQ</u>RG<u>A</u>KKLLYIFKQ | CD28-4-1BB junction region K14Q/R17A variant |
| 150 | SLLVTVAFIIFW<u>VQ</u>RG<u>N</u>KKLLYIFKQ | CD28-4-1BB junction region K14Q/R17N variant |
| 151 | SLLVTVAFIIFW<u>VQ</u>RG<u>S</u>KKLLYIFKQ | CD28-4-1BB junction region K14Q/R17S variant |

TABLE 5 -continued

Sequences

| SEQ ID NO | Sequence | Note |
|---|---|---|
| 152 | SLLVTVAFIIFWVRGRKKALYIFKQ | CD28-4-1BB junction region K14Q/L20A variant |
| 153 | SLLVTVAFIIFWVRGRKKSLYIFKQ | CD28-4-1BB junction region K14Q/L20S variant |
| 154 | SLLVTVAFIIFWVKRGNKKALYIFKQ | CD28-4-1BB junction region R17N/L20A variant |
| 155 | SLLVTVAFIIFWVKRGNKKSLYIFKQ | CD28-4-1BB junction region R17N/L20S variant |
| 156 | SLLVTVAFIIFWVRGNKKALYIFKQ | CD28-4-1BB junction region K14Q/R17N/L20A variant |
| 157 | SLLVTVAFIIFWVRGNKKSLYIFKQ | CD28-4-1BB junction region K14Q/R17N/L20S variant |
| 158 | G A A T C T A A G T A C G G A C C G C C C T G C C C C C C T T G C C C T | spacer (IgG4hinge) (nucleotide) *homo sapien* |
| 159 | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 Zeta |

The invention claimed is:

1. A method of treatment, comprising:

(a) administering to a subject T cells expressing a first chimeric antigen receptor (CAR) that specifically binds to a first antigen associated with a disease or condition in the subject, wherein the disease or condition comprises a B cell acute lymphoblastic leukemia (B-ALL) and the first antigen is CD19; and (b) subsequently administering, to a subject in which the disease or condition has relapsed following the administration of the first CAR in (a), T cells expressing a second CAR that specifically binds to a second antigen that is CD22, wherein:

at the time of, or immediately prior to, the administration of T cells expressing the second CAR, the subject is in the relapse following the administration of T cells expressing the first CAR; and the T cells expressing the second CAR do not express the first CAR, and the second CAR comprises at least one region identical in amino acid sequence to a corresponding region of the first CAR.

2. A method of treatment, comprising administering T cells expressing a second chimeric antigen receptor (CAR) to a subject that has previously received an administration of T cells expressing a first chimeric antigen receptor (CAR) and has relapsed following the previous administration of the first CAR, wherein:

said T cells expressing the second CAR do not express the first CAR;

said first CAR specifically binds to a first antigen associated with a disease or condition in the subject, wherein the disease or condition comprises a B cell acute lymphoblastic leukemia (B-ALL) and the first antigen is CD19;

said second CAR specifically binds to a second antigen that is CD22, and said second CAR comprises at least one region identical in amino acid sequence to a corresponding region of said first CAR; and at the time of, or immediately prior to, the administration of T cells expressing the second CAR, the subject is in the relapse following the administration of T cells expressing the first CAR.

3. The method of claim 1, wherein:
the time between the initiation of administration of T cells expressing the first CAR and the initiation of administration of T cells expressing the second CAR is at least about 28 days, at least about 35 days, at least about 42 days, at least about 49 days, or at least about 60 days.

4. The method of claim 2, wherein:
the time between initiation of the administration of T cells expressing the first CAR and initiation of the administration of T cells expressing the second CAR is at least about 28 days, at least about 35 days, at least about 42 days, at least about 49 days, or at least about 60 days.

5. The method of claim 2, wherein said subject has not received a dose of T cells expressing the second CAR prior to the administration of cells expressing the second CAR.

6. The method of claim 2, wherein:
the administration of the T cells expressing the second CAR comprises administration of the cells in an amount sufficient for reduction in burden of the disease or condition in the subject; or
the administration of the T cells expressing the second CAR effects a reduction in burden of the disease or condition in the subject, thereby treating the disease or condition.

7. The method of claim 2, wherein:
the administration of the T cells expressing the first CAR comprises administration of the cells in an amount sufficient for reduction in burden of the disease or condition in the subject; or
the administration of the T cells expressing the first CAR and/or the administration of the cells expressing the second CAR effects a reduction in burden of the disease or condition in the subject, thereby treating the disease or condition.

8. The method of claim 2, wherein the T cells expressing the second CAR are autologous to the subject.

9. The method of claim 2, wherein the administration of the T cells expressing the first CAR and/or the administration of the T cells expressing the second CAR independently comprises administration of from or from about $1\times10^6$ to about $1\times10^8$ of the CAR-expressing T cells.

10. The method of claim 2, wherein administration of the T cells expressing the second CAR comprise administration of from or from about $1\times10^6$ to about $1\times10^8$ of the CAR-expressing T cells.

11. The method of claim 2, wherein the T cells expressing the first CAR are autologous to the subject.

12. The method of claim 1, wherein the T cells expressing the first CAR and the T cells expressing the second CAR are autologous to the subject.

13. The method of 1, wherein the administration of the T cells expressing the first CAR and/or the administration of the T cells expressing the second CAR independently comprises administration of from or from about $1\times10^6$ to about $1\times10^8$ of the CAR-expressing T cells.

14. The method of claim 1, wherein administration of the T cells expressing the second CAR comprise administration of from or from about $1\times10^6$ to about $1\times10^8$ of the CAR-expressing T cells.

15. The method of claim 2, wherein said subject has not received a dose of T cells expressing a CAR that binds to the second antigen prior to the administration of T cells expressing the second CAR.

16. A method of treatment, comprising:
(a) administering, to a subject having a disease or condition that is a B cell malignancy, T cells expressing a first chimeric antigen receptor (CAR) that specifically binds to a first antigen that is CD19; and
(b) subsequently administering, to a subject in which the disease or condition has relapsed following the administration of the first CAR in (a), T cells expressing a second CAR that specifically binds to a second antigen that is CD22, wherein the T cells expressing the second CAR do not express the first CAR, and the second CAR comprises at least one region identical in amino acid sequence to a corresponding region of the first CAR, wherein:
at the time of, or immediately prior to, initiation of the administration of T cells expressing the second CAR, the subject is in the relapse following the administration of T cells expressing the first CAR.

17. The method of claim 16, wherein the disease or condition is a leukemia or a lymphoma.

18. The method of claim 16, wherein the T cells expressing the first CAR and the T cells expressing the second CAR are autologous to the subject.

19. The method of claim 16, wherein the administration of the T cells expressing the first CAR and/or the administration of the cells expressing the second CAR independently comprises administration of from or from about $1\times10^6$ to about $1\times10^8$ of the CAR-expressing T cells.

20. The method of claim 16, wherein the time between the initiation of administration of the T cells expressing the first CAR and the initiation of administration of the T cells expressing the second CAR is at least about 28 days, at least about 35 days, at least about 42 days, at least about 49 days, or at least about 60 days.

21. A method of treatment, comprising administering, to a subject having a disease or condition that is a B cell malignancy, T cells expressing a second chimeric antigen receptor (CAR), wherein:
the subject has previously received an administration of T cells expressing a first chimeric antigen receptor (CAR) that specifically binds to a first antigen that is CD19 and has relapsed following the previous administration of the first CAR;
the second CAR specifically binds to a second antigen that is CD22, wherein the T cells expressing the second CAR do not express the first CAR, and the second CAR comprises at least one region identical in amino acid sequence to a corresponding region of the first CAR; and
at the time of, or immediately prior to, initiation of the administration of T cells expressing the second CAR, the subject is in the relapse following the administration of T cells expressing the first CAR.

22. The method of claim 21, wherein the T cells expressing the second CAR are autologous to the subject.

23. The method of claim 21, wherein the administration of the T cells expressing the first CAR and/or the administration of the T cells expressing the second CAR independently comprise from or from about $1\times10^6$ to about $1\times10^8$ of the CAR-expressing T cells.

24. The method of claim 21, wherein the time between the initiation of administration of T cells expressing the first CAR and the initiation of administration of T cells expressing the second CAR is at least about 28 days, at least about 35 days, at least about 42 days, at least about 49 days, or at least about 60 days.

25. The method of claim 21, wherein said subject has not received a dose of T cells expressing the second CAR prior to the administration of T cells expressing the second CAR.

26. The method of claim 21, wherein said subject has not received a dose of cells expressing a CAR that binds to the second antigen prior to the administration of cells expressing the second CAR.

27. The method of claim 16, wherein administration of the T cells expressing the second CAR comprise administration of from or from about $1\times10^6$ to about $1\times10^8$ of the CAR-expressing T cells.

28. The method of claim 21, wherein administration of the T cells expressing the second CAR comprise administration of from or from about $1\times10^6$ to about $1\times10^8$ of the CAR-expressing T cells.

29. The method of claim 1, wherein the at least one region identical in sequence is selected from the group consisting of an intracellular costimulatory signaling domain, an ITAM-containing domain, a transmembrane domain, and a combination thereof.

30. The method of claim 29, wherein the at least one region identical in amino acid sequence is an ITAM-containing domain that is a human CD3zeta signaling domain.

31. The method of claim 29, wherein the at least one region identical in amino acid sequence is a costimulatory signaling domain that is a CD28 signaling domain or a 4-1BB signaling domain.

32. The method of claim 30, wherein the at least one region identical in amino acid sequence further comprises a costimulatory signaling domain that is a 4-1BB signaling domain.

33. The method of claim 2, wherein the at least one region identical in amino acid sequence is selected from the group consisting of an intracellular costimulatory signaling domain, an ITAM-containing domain, a transmembrane domain, and a combination thereof.

34. The method of claim 33, wherein the at least one region identical in amino acid sequence is an ITAM-containing domain that is a human CD3zeta signaling domain.

35. The method of claim 33, wherein the at least one region identical in amino acid sequence is a costimulatory signaling domain that is a CD28 signaling domain or a 4-1BB signaling domain.

36. The method of claim 34, wherein the at least one region identical in amino acid sequence further comprises a costimulatory signaling domain that is a 4-1BB signaling domain.

37. The method of claim 16, wherein the at least one region identical in amino acid sequence is selected from the group consisting of an intracellular costimulatory signaling domain, an ITAM-containing domain, a transmembrane domain, and a combination thereof.

38. The method of claim 37, wherein the at least one region identical in amino acid sequence is an ITAM-containing domain that is a human CD3zeta signaling domain.

39. The method of claim 37, wherein the at least one region identical in amino acid sequence is a costimulatory signaling domain that is a CD28 signaling domain or a 4-1BB signaling domain.

40. The method of claim 38, wherein the at least one region identical in amino acid sequence further comprises a costimulatory signaling domain that is a 4-1BB signaling domain.

41. The method of claim 21, wherein the at least one region identical in amino acid sequence is selected from the group consisting of an intracellular costimulatory signaling domain, an ITAM-containing domain, a transmembrane domain, and a combination thereof.

42. The method of claim 41, wherein the at least one region identical in amino acid sequence is an ITAM-containing domain that is a human CD3zeta signaling domain.

43. The method of claim 41, wherein the at least one region identical in amino acid sequence is a costimulatory signaling domain that is a CD28 signaling domain or a 4-1BB signaling domain.

44. The method of claim 42, wherein the at least one region identical in amino acid sequence further comprises costimulatory signaling domain that is a 4-1BB signaling domain.

45. The method of claim 21, wherein the B cell malignancy is a leukemia or a lymphoma.

* * * * *

SEQUENCE LISTING

```
<160> NUMBER OF SEQ ID NOS: 159

<210> SEQ ID NO 1
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: IgG4 hinge

<400> SEQUENCE: 1

Glu Ser Lys Tyr Gly Pro Pro Cys Pro Pro Cys Pro
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Synthetic
<220> FEATURE:
<223> OTHER INFORMATION: CD28 transmembrane domain

<400> SEQUENCE: 2

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25
```

```
<210> SEQ ID NO 3
<211> LENGTH: 42
<212> TYPE: PRT
<213> ORGANISM: Homo sapiens
<220> FEATURE:
<223> OTHER INFORMATION: 4-1BB costimulatory domain

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 4
<211> LENGTH: 112
<212> TYPE: PRT
<213> ORGANISM: Artificial Sequence
<220> FEATURE:
<223> OTHER INFORMATION: Synthetic
<220> FEATURE:
<223> OTHER INFORMATION: CD3-zeta intracellular signaling domain

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 69
<212> TYPE: PRT
<213> ORGANISM: Artificial Sequence
<220> FEATURE:
<223> OTHER INFORMATION: Synthetic
<220> FEATURE:
<223> OTHER INFORMATION: CD28-4-1BB

<400> SEQUENCE: 5

Phe Trp Val Leu Val Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65
```

```
<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

Cys Tyr Ser Leu Leu Val Thr Val Ala Phe Ile Ile Phe Trp Val Lys
1               5                   10                  15

Arg Gly Arg Lys Lys Leu Leu Tyr Ile Phe Lys Gln Pro Phe
            20                  25                  30

<210> SEQ ID NO 7
<211> LENGTH: 16
<212> TYPE: PRT
<213> ORGANISM: Artificial Sequence
<220> FEATURE:
<223> OTHER INFORMATION: Synthetic

<400> SEQUENCE: 7

Val Ala Phe Ile Ile Phe Trp Val Lys Arg Gly Arg Lys Lys Leu Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Phe Ile Ile Phe Trp Val Lys Arg Gly Arg Lys Lys Leu Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Phe Trp Val Lys Arg Gly Arg Lys Lys Leu Leu Tyr Ile Phe Lys
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Phe Ile Ile Phe Trp Val Lys Arg Gly Arg Lys Lys Leu Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Phe Ile Ile Phe Trp Val Lys Arg Gly Arg Lys Lys Leu
1               5                   10
```

-continued

```
<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ile Ile Phe Trp Val Lys Arg Gly Arg Lys Lys Leu Leu
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Synthetic
<220> FEATURE:
<223> OTHER INFORMATION: Variant junction region

<400> SEQUENCE: 13

Cys Tyr Ser Leu Leu Val Thr Val Ala Phe Ile Ile Phe Trp Val Asn
1               5                   10                  15

Asn Lys Arg Gly Arg Lys Lys Leu Leu Tyr Ile Phe Lys Gln Pro Phe
            20                  25                  30

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: Variant peptide

<400> SEQUENCE: 14

Ile Ile Phe Trp Val Asn Asn Lys Arg Gly Arg Lys Lys Leu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic
<220> FEATURE:
<223> OTHER INFORMATION: Variant peptide

<400> SEQUENCE: 15

Ile Ile Phe Trp Val Asn Asn Lys Arg Gly Arg Lys Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Val Ala Phe Ile Ile Phe Trp Val Lys
1               5

<210> SEQ ID NO 17
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 17

Ala Phe Ile Ile Phe Trp Val Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Phe Ile Ile Phe Trp Val Lys Arg Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Ile Ile Phe Trp Val Lys Arg Gly Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Ile Phe Trp Val Lys Arg Gly Arg Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Phe Trp Val Lys Arg Gly Arg Lys Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Trp Val Lys Arg Gly Arg Lys Lys Leu
1               5

<210> SEQ ID NO 23
<211> LENGTH: 9
<212> TYPE: PRT
<213> ORGANISM: Artificial Sequence
```

```
<220> FEATURE:
<223> OTHER INFORMATION: Synthetic peptide K28S

<400> SEQUENCE: 23

Val Ala Phe Ile Ile Phe Trp Val Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 24

Ala Phe Ile Ile Phe Trp Val Ser Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 25

Phe Ile Ile Phe Trp Val Ser Arg Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 26

Ile Ile Phe Trp Val Ser Arg Gly Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 27

Ile Phe Trp Val Ser Arg Gly Arg Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide K28S

<400> SEQUENCE: 28

Phe Trp Val Ser Arg Gly Arg Lys Lys
1               5

<210> SEQ ID NO 29
<211> LENGTH: 9
<212> TYPE: PRT
<213> ORGANISM: Artificial Sequence
```

```
<220> FEATURE:
<223> OTHER INFORMATION: Synthetic peptide K28S

<400> SEQUENCE: 29

Trp Val Ser Arg Gly Arg Lys Lys Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 30

Val Ala Phe Ile Ile Phe Trp Val Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 31

Ala Phe Ile Ile Phe Trp Val Leu Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 32

Phe Ile Ile Phe Trp Val Leu Arg Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 33

Ile Ile Phe Trp Val Leu Arg Gly Arg
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 34

Ile Phe Trp Val Leu Arg Gly Arg Lys
1               5

<210> SEQ ID NO 35
<211> LENGTH: 9
<212> TYPE: PRT
<213> ORGANISM: Artificial Sequence
```

```
<220> FEATURE:
<223> OTHER INFORMATION: Synthetic peptide K28L

<400> SEQUENCE: 35

Phe Trp Val Leu Arg Gly Arg Lys Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide K28L

<400> SEQUENCE: 36

Trp Val Leu Arg Gly Arg Lys Lys Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 37

Val Ala Phe Ile Ile Phe Trp Val His
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 38

Ala Phe Ile Ile Phe Trp Val His Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 39

Phe Ile Ile Phe Trp Val His Arg Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 40

Ile Ile Phe Trp Val His Arg Gly Arg
1               5

<210> SEQ ID NO 41
<211> LENGTH: 9
<212> TYPE: PRT
<213> ORGANISM: Artificial Sequence
```

```
<220> FEATURE:
<223> OTHER INFORMATION: Synthetic peptide K28H

<400> SEQUENCE: 41

Ile Phe Trp Val His Arg Gly Arg Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 42

Phe Trp Val His Arg Gly Arg Lys Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide K28H

<400> SEQUENCE: 43

Trp Val His Arg Gly Arg Lys Lys Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 44

Val Ala Phe Ile Ile Phe Trp Val Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 45

Ala Phe Ile Ile Phe Trp Val Ala Arg
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 46

Ile Ile Phe Trp Val Ala Arg Gly Arg
1               5

<210> SEQ ID NO 47
<211> LENGTH: 9
<212> TYPE: PRT
<213> ORGANISM: Artificial Sequence
```

```
<220> FEATURE:
<223> OTHER INFORMATION: Synthetic peptide K28A

<400> SEQUENCE: 47

Ile Phe Trp Val Ala Arg Gly Arg Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 48

Phe Trp Val Ala Arg Gly Arg Lys Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 49

Trp Val Ala Arg Gly Arg Lys Lys Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 50

Val Ala Phe Ile Ile Phe Trp Val Gln
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 51

Ala Phe Ile Ile Phe Trp Val Gln Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 52

Phe Ile Ile Phe Trp Val Gln Arg Gly
1               5

<210> SEQ ID NO 53
<211> LENGTH: 9
<212> TYPE: PRT
<213> ORGANISM: Artificial Sequence
```

```
<220> FEATURE:
<223> OTHER INFORMATION: Synthetic peptide K28Q

<400> SEQUENCE: 53

Ile Ile Phe Trp Val Gln Arg Gly Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 54

Ile Phe Trp Val Gln Arg Gly Arg Lys
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 55

Phe Trp Val Gln Arg Gly Arg Lys Lys
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide K28Q

<400> SEQUENCE: 56

Trp Val Gln Arg Gly Arg Lys Lys Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 57

Ile Ile Phe Trp Val Lys Arg Gly Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 58

Ile Phe Trp Val Lys Arg Gly Ser Lys
1               5

<210> SEQ ID NO 59
<211> LENGTH: 9
<212> TYPE: PRT
<213> ORGANISM: Artificial Sequence
```

```
<220> FEATURE:
<223> OTHER INFORMATION: Synthetic peptide R31S

<400> SEQUENCE: 59

Phe Trp Val Lys Arg Gly Ser Lys Lys
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide R31S

<400> SEQUENCE: 60

Trp Val Lys Arg Gly Ser Lys Lys Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 61

Ile Ile Phe Trp Val Lys Arg Gly Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 62

Ile Phe Trp Val Lys Arg Gly Leu Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 63

Phe Trp Val Lys Arg Gly Leu Lys Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide R31L

<400> SEQUENCE: 64

Trp Val Lys Arg Gly Leu Lys Lys Leu
1               5

<210> SEQ ID NO 65
<211> LENGTH: 9
<212> TYPE: PRT
<213> ORGANISM: Artificial Sequence
```

```
<220> FEATURE:
<223> OTHER INFORMATION: Synthetic peptide R31H

<400> SEQUENCE: 65

Ile Ile Phe Trp Val Lys Arg Gly His
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 66

Ile Phe Trp Val Lys Arg Gly His Lys
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 67

Phe Trp Val Lys Arg Gly His Lys Lys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide R31H

<400> SEQUENCE: 68

Trp Val Lys Arg Gly His Lys Lys Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 69

Ile Ile Phe Trp Val Lys Arg Gly Ala
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 70

Ile Phe Trp Val Lys Arg Gly Ala Lys
1               5

<210> SEQ ID NO 71
<211> LENGTH: 9
<212> TYPE: PRT
<213> ORGANISM: Artificial Sequence
```

<220> FEATURE:
<223> OTHER INFORMATION: Synthetic peptide R31A

<400> SEQUENCE: 71

Phe Trp Val Lys Arg Gly Ala Lys Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide R31A

<400> SEQUENCE: 72

Trp Val Lys Arg Gly Ala Lys Lys Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 73

Ile Ile Phe Trp Val Lys Arg Gly Asn
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 74

Ile Phe Trp Val Lys Arg Gly Asn Lys
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 75

Phe Trp Val Lys Arg Gly Asn Lys Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide R31N

<400> SEQUENCE: 76

Trp Val Lys Arg Gly Asn Lys Lys Leu
1               5

<210> SEQ ID NO 77
<211> LENGTH: 9
<212> TYPE: PRT
<213> ORGANISM: Artificial Sequence

```
<220> FEATURE:
<223> OTHER INFORMATION: Synthetic peptide K28Q/R31S

<400> SEQUENCE: 77

Ile Ile Phe Trp Val Gln Arg Gly Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 78

Ile Phe Trp Val Gln Arg Gly Ser Lys
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 79

Phe Trp Val Gln Arg Gly Ser Lys Lys
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide K28Q/R31S

<400> SEQUENCE: 80

Trp Val Gln Arg Gly Ser Lys Lys Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 81

Ile Ile Phe Trp Val Gln Arg Gly Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 82

Ile Phe Trp Val Gln Arg Gly Ala Lys
1               5

<210> SEQ ID NO 83
<211> LENGTH: 9
<212> TYPE: PRT
<213> ORGANISM: Artificial Sequence
```

```
<220> FEATURE:
<223> OTHER INFORMATION: Synthetic peptide K28Q/R31A

<400> SEQUENCE: 83

Phe Trp Val Gln Arg Gly Ala Lys Lys
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide K28Q/R31A

<400> SEQUENCE: 84

Trp Val Gln Arg Gly Ala Lys Lys Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 85

Ile Ile Phe Trp Val Gln Arg Gly Asn
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 86

Ile Phe Trp Val Gln Arg Gly Asn Lys
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 87

Phe Trp Val Gln Arg Gly Asn Lys Lys
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide K28Q/R31N

<400> SEQUENCE: 88

Trp Val Gln Arg Gly Asn Lys Lys Leu
1               5

<210> SEQ ID NO 89
<211> LENGTH: 9
<212> TYPE: PRT
<213> ORGANISM: Artificial Sequence
```

```
<220> FEATURE:
<223> OTHER INFORMATION: Synthetic peptide L34S

<400> SEQUENCE: 89

Trp Val Lys Arg Gly Arg Lys Lys Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide L34A

<400> SEQUENCE: 90

Trp Val Lys Arg Gly Arg Lys Lys Ala
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide K28Q/L34S

<400> SEQUENCE: 91

Trp Val Gln Arg Gly Asn Lys Lys Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide K28Q/L34A

<400> SEQUENCE: 92

Trp Val Gln Arg Gly Asn Lys Lys Ala
1               5

<210> SEQ ID NO 93
<211> LENGTH: 255
<212> TYPE: PRT
<213> ORGANISM: Homo sapiens
<220> FEATURE:
<223> OTHER INFORMATION: 4-1BB

<400> SEQUENCE: 93

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110
```

```
Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 94
<211> LENGTH: 255
<212> TYPE: PRT
<213> ORGANISM: Homo sapiens
<220> FEATURE:
<223> OTHER INFORMATION: CD28

<400> SEQUENCE: 94

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220
```

```
Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 95
<211> LENGTH: 164
<212> TYPE: PRT
<213> ORGANISM: Homo sapiens
<220> FEATURE:
<223> OTHER INFORMATION: CD3 zeta chain

<400> SEQUENCE: 95

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 96
<211> LENGTH: 14
<212> TYPE: PRT
<213> ORGANISM: Artificial Sequence
<220> FEATURE:
<223> OTHER INFORMATION: Synthetic

<400> SEQUENCE: 96

Phe Ile Ile Phe Trp Val Asn Asn Lys Arg Gly Arg Lys Lys
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic

<400> SEQUENCE: 97

Ile Phe Trp Val Asn Asn Lys Arg Gly Arg Lys Lys Leu Leu
1               5                   10

<210> SEQ ID NO 98
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 98

Phe Ile Ile Phe Trp Val Asn Asn Lys Arg Gly Arg Lys Lys
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Ile Phe Trp Val Asn Asn Lys Arg Gly Arg Lys Lys Leu Leu
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide K28R

<400> SEQUENCE: 100

Val Ala Phe Ile Ile Phe Trp Val Arg
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide K28R

<400> SEQUENCE: 101

Ala Phe Ile Ile Phe Trp Val Arg Arg
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide K28A

<400> SEQUENCE: 102

Phe Ile Ile Phe Trp Val Ala Arg Gly
1               5

<210> SEQ ID NO 103
<211> LENGTH: 28
<212> TYPE: PRT
<213> ORGANISM: Homo sapiens
<220> FEATURE:
<223> OTHER INFORMATION: CD28 transmembrane domain

<400> SEQUENCE: 103

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

```
<210> SEQ ID NO 104
<211> LENGTH: 66
<212> TYPE: PRT
<213> ORGANISM: Homo sapiens
<220> FEATURE:
<223> OTHER INFORMATION: CD28

<400> SEQUENCE: 104

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 105
<211> LENGTH: 112
<212> TYPE: PRT
<213> ORGANISM: Homo sapiens
<220> FEATURE:
<223> OTHER INFORMATION: CD3 zeta

<400> SEQUENCE: 105

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 106
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 106
gaatctaagt acggaccgcc ctgcccccct tgccct                           36

<210> SEQ ID NO 107
<211> LENGTH: 119
<212> TYPE: PRT
<213> ORGANISM: Homo sapiens
<220> FEATURE:
<223> OTHER INFORMATION: Hinge-CH3 spacer
```

```
<400> SEQUENCE: 107

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
            115

<210> SEQ ID NO 108
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 108

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

```
Val Met His Glu Ala Leu His Asn His Tyr Thr Gln Lys Ser Leu Ser
    210                 215                 220
Leu Ser Leu Gly Lys
225

<210> SEQ ID NO 109
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 109

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 110
<211> LENGTH: 24
<212> TYPE: PRT
<213> ORGANISM: Artificial Sequence
<220> FEATURE:
<223> OTHER INFORMATION: Synthetic
<220> FEATURE:
<223> OTHER INFORMATION: T2A
```

<400> SEQUENCE: 110

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 111
<211> LENGTH: 357
<212> TYPE: PRT
<213> ORGANISM: Artificial Sequence
<220> FEATURE:
<223> OTHER INFORMATION: Synthetic
<220> FEATURE:
<223> OTHER INFORMATION: tEGFR

<400> SEQUENCE: 111

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

```
Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
        340                 345                 350

Ile Gly Leu Phe Met
        355

<210> SEQ ID NO 112
<211> LENGTH: 41
<212> TYPE: PRT
<213> ORGANISM: Homo sapiens
<220> FEATURE:
<223> OTHER INFORMATION: CD28 cytoplasmic domain

<400> SEQUENCE: 112

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 113
<211> LENGTH: 41
<212> TYPE: PRT
<213> ORGANISM: Homo sapiens
<220> FEATURE:
<223> OTHER INFORMATION: CD28 cytoplasmic domain

<400> SEQUENCE: 113

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 114
<211> LENGTH: 69
<212> TYPE: PRT
<213> ORGANISM: Artificial Sequence
<220> FEATURE:
<223> OTHER INFORMATION: Synthetic K28A

<400> SEQUENCE: 114

Phe Trp Val Leu Val Val Val Gly Gly Val Leu Ala Cys Tyr Ser Leu
1               5                   10                  15

Leu Val Thr Val Ala Phe Ile Ile Phe Trp Val Ala Arg Gly Arg Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 115
<211> LENGTH: 69
<212> TYPE: PRT
<213> ORGANISM: Artificial Sequence
<220> FEATURE:
<223> OTHER INFORMATION: Synthetic K28H
```

<400> SEQUENCE: 115

Phe Trp Val Leu Val Val Gly Gly Val Leu Ala Cys Tyr Ser Leu
1               5                   10                  15

Leu Val Thr Val Ala Phe Ile Ile Phe Trp Val His Arg Gly Arg Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 116
<211> LENGTH: 69
<212> TYPE: PRT
<213> ORGANISM: Artificial Sequence
<220> FEATURE:
<223> OTHER INFORMATION: Synthetic K28L

<400> SEQUENCE: 116

Phe Trp Val Leu Val Val Gly Gly Val Leu Ala Cys Tyr Ser Leu
1               5                   10                  15

Leu Val Thr Val Ala Phe Ile Ile Phe Trp Val Leu Arg Gly Arg Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 117
<211> LENGTH: 69
<212> TYPE: PRT
<213> ORGANISM: Artificial Sequence
<220> FEATURE:
<223> OTHER INFORMATION: Synthetic K28Q

<400> SEQUENCE: 117

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Arg Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 118
<211> LENGTH: 69
<212> TYPE: PRT
<213> ORGANISM: Artificial Sequence
<220> FEATURE:
<223> OTHER INFORMATION: Synthetic K28S -continued

```
<400> SEQUENCE: 118

Phe Trp Val Leu Val Val Gly Gly Val Leu Ala Cys Tyr Ser Leu
1               5                   10                  15

Leu Val Thr Val Ala Phe Ile Ile Phe Trp Val Ser Arg Gly Arg Lys
                20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 119
<211> LENGTH: 69
<212> TYPE: PRT
<213> ORGANISM: Artificial Sequence
<220> FEATURE:
<223> OTHER INFORMATION: Synthetic R31A

<400> SEQUENCE: 119

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Ala Lys
                20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 120
<211> LENGTH: 69
<212> TYPE: PRT
<213> ORGANISM: Artificial Sequence
<220> FEATURE:
<223> OTHER INFORMATION: Synthetic R31H

<400> SEQUENCE: 120

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly His Lys
                20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 121
<211> LENGTH: 69
<212> TYPE: PRT
<213> ORGANISM: Artificial Sequence
<220> FEATURE:
<223> OTHER INFORMATION: Synthetic R31L
```

-continued

```
<400> SEQUENCE: 121

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Leu Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 122
<211> LENGTH: 69
<212> TYPE: PRT
<213> ORGANISM: Artificial Sequence
<220> FEATURE:
<223> OTHER INFORMATION: Synthetic R31N

<400> SEQUENCE: 122

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
            20                  25                  30

Lys Leu Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 123
<211> LENGTH: 69
<212> TYPE: PRT
<213> ORGANISM: Artificial Sequence
<220> FEATURE:
<223> OTHER INFORMATION: Synthetic L34A

<400> SEQUENCE: 123

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Ala Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 124
<211> LENGTH: 69
<212> TYPE: PRT
<213> ORGANISM: Artificial Sequence
<220> FEATURE:
<223> OTHER INFORMATION: Synthetic L34S
```

<400> SEQUENCE: 124

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Arg Lys
            20                  25                  30

Lys Ser Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 125
<211> LENGTH: 69
<212> TYPE: PRT
<213> ORGANISM: Artificial Sequence
<220> FEATURE:
<223> OTHER INFORMATION: Synthetic K28Q/R31A

<400> SEQUENCE: 125

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Ala Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 126
<211> LENGTH: 69
<212> TYPE: PRT
<213> ORGANISM: Artificial Sequence
<220> FEATURE:
<223> OTHER INFORMATION: Synthetic K28Q/R31N

<400> SEQUENCE: 126

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 127
<211> LENGTH: 69
<212> TYPE: PRT
<213> ORGANISM: Artificial Sequence
<220> FEATURE:
<223> OTHER INFORMATION: Synthetic K28Q/R31S

```
<400> SEQUENCE: 127

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Ser Lys
            20                  25                  30

Lys Leu Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 128
<211> LENGTH: 69
<212> TYPE: PRT
<213> ORGANISM: Artificial Sequence
<220> FEATURE:
<223> OTHER INFORMATION: Synthetic K28Q/L34A

<400> SEQUENCE: 128

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Arg Lys
            20                  25                  30

Lys Ala Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 129
<211> LENGTH: 69
<212> TYPE: PRT
<213> ORGANISM: Artificial Sequence
<220> FEATURE:
<223> OTHER INFORMATION: Synthetic K28Q/L34S

<400> SEQUENCE: 129

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Arg Lys
            20                  25                  30

Lys Ser Leu Tyr Ile Phe Lys Gln Pro Phe Met Arg Pro Val Gln Thr
            35                  40                  45

Thr Gln Glu Glu Asp Gly Cys Ser Cys Arg Phe Pro Glu Glu Glu Glu
        50                  55                  60

Gly Gly Cys Glu Leu
65

<210> SEQ ID NO 130
<211> LENGTH: 69
<212> TYPE: PRT
<213> ORGANISM: Artificial Sequence
<220> FEATURE:
<223> OTHER INFORMATION: Synthetic R31N/L34A
```

-continued

```
<400> SEQUENCE: 130

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
            20                  25                  30

Lys Ala Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 131
<211> LENGTH: 69
<212> TYPE: PRT
<213> ORGANISM: Artificial Sequence
<220> FEATURE:
<223> OTHER INFORMATION: Synthetic R31N/L34S

<400> SEQUENCE: 131

Phe Trp Val Leu Val Val Gly Gly Val Leu Ala Cys Tyr Ser Leu
1               5                   10                  15

Leu Val Thr Val Ala Phe Ile Ile Phe Trp Val Lys Arg Gly Asn Lys
            20                  25                  30

Lys Ser Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 132
<211> LENGTH: 69
<212> TYPE: PRT
<213> ORGANISM: Artificial Sequence
<220> FEATURE:
<223> OTHER INFORMATION: Synthetic K28Q/R31N/L34A

<400> SEQUENCE: 132

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
            20                  25                  30

Lys Ala Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu Glu
    50                  55                  60

Gly Gly Cys Glu Leu
65

<210> SEQ ID NO 133
<211> LENGTH: 69
<212> TYPE: PRT
<213> ORGANISM: Artificial Sequence
<220> FEATURE:
<223> OTHER INFORMATION: Synthetic K28Q/R31N/L34S
```

<400> SEQUENCE: 133

Phe Trp Val Leu Val Val Gly Gly Val Leu Ala Cys Tyr Ser Leu
1               5                   10                  15

Leu Val Thr Val Ala Phe Ile Ile Phe Trp Val Gln Arg Gly Asn Lys
            20                  25                  30

Lys Ser Leu Tyr Ile Phe Lys Gln Pro Phe Met Arg Pro Val Gln Thr
        35                  40                  45

Thr Gln Glu Glu Asp Gly Cys Ser Cys Arg Phe Pro Glu Glu Glu
    50                  55                  60

Gly Gly Cys Glu Leu
65

<210> SEQ ID NO 134
<211> LENGTH: 71
<212> TYPE: PRT
<213> ORGANISM: Artificial Sequence
<220> FEATURE:
<223> OTHER INFORMATION: Synthetic
<220> FEATURE:
<223> OTHER INFORMATION: NN Insertion

<400> SEQUENCE: 134

Phe Trp Val Leu Val Val Gly Gly Val Leu Ala Cys Tyr Ser Leu
1               5                   10                  15

Leu Val Thr Val Ala Phe Ile Ile Phe Trp Val Asn Asn Lys Arg Gly
            20                  25                  30

Arg Lys Lys Leu Leu Tyr Ile Phe Lys Gln Pro Phe Met Arg Pro Val
        35                  40                  45

Gln Thr Thr Gln Glu Glu Asp Gly Cys Ser Cys Arg Phe Pro Glu Glu
    50                  55                  60

Glu Glu Gly Gly Cys Glu Leu
65                  70

<210> SEQ ID NO 135
<211> LENGTH: 70
<212> TYPE: PRT
<213> ORGANISM: Artificial Sequence
<220> FEATURE:
<223> OTHER INFORMATION: Synthetic

<400> SEQUENCE: 135

Met Phe Trp Val Leu Val Val Gly Gly Val Leu Ala Cys Tyr Ser
1               5                   10                  15

Leu Leu Val Thr Val Ala Phe Ile Ile Phe Trp Val Lys Arg Gly Arg
            20                  25                  30

Lys Lys Leu Leu Tyr Ile Phe Lys Gln Pro Phe Met Arg Pro Val Gln
        35                  40                  45

Thr Thr Gln Glu Glu Asp Gly Cys Ser Cys Arg Phe Pro Glu Glu Glu
    50                  55                  60

Glu Gly Gly Cys Glu Leu
65                  70

<210> SEQ ID NO 136
<211> LENGTH: 108
<212> TYPE: PRT
<213> ORGANISM: Artificial Sequence
<220> FEATURE:
<223> OTHER INFORMATION: Synthetic -continued

<400> SEQUENCE: 136

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Gly Gly
        35                  40                  45

Val Leu Ala Cys Tyr Ser Leu Leu Val Thr Val Ala Phe Ile Ile Phe
    50                  55                  60

Trp Val Lys Arg Gly Arg Lys Lys Leu Leu Tyr Ile Phe Lys Gln Pro
65                  70                  75                  80

Phe Met Arg Pro Val Gln Thr Thr Gln Glu Asp Gly Cys Ser Cys
                85                  90                  95

Arg Phe Pro Glu Glu Glu Glu Gly Gly Cys Glu Leu
                100                 105

<210> SEQ ID NO 137
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region

<400> SEQUENCE: 137

Ser Leu Leu Val Thr Val Ala Phe Ile Ile Phe Trp Val Lys Arg Gly
1               5                   10                  15

Arg Lys Lys Leu Leu Tyr Ile Phe Lys Gln
            20                  25

<210> SEQ ID NO 138
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14A

<400> SEQUENCE: 138

Ser Leu Leu Val Thr Val Ala Phe Ile Ile Phe Trp Val Ala Arg Gly
1               5                   10                  15

Arg Lys Lys Leu Leu Tyr Ile Phe Lys Gln
            20                  25

<210> SEQ ID NO 139
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14H

<400> SEQUENCE: 139

Ser Leu Leu Val Thr Val Ala Phe Ile Ile Phe Trp Val His Arg Gly
1               5                   10                  15

Arg Lys Lys Leu Leu Tyr Ile Phe Lys Gln
            20                  25

```
<210> SEQ ID NO 140
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14L

<400> SEQUENCE: 140

Ser Leu Leu Val Thr Val Ala Phe Ile Ile Phe Trp Val Leu Arg Gly
1               5                   10                  15

Arg Lys Lys Leu Leu Tyr Ile Phe Lys Gln
            20                  25

<210> SEQ ID NO 141
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q

<400> SEQUENCE: 141

Ser Leu Leu Val Thr Val Ala Phe Ile Ile Phe Trp Val Gln Arg Gly
1               5                   10                  15

Arg Lys Lys Leu Leu Tyr Ile Phe Lys Gln
            20                  25

<210> SEQ ID NO 142
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14S

<400> SEQUENCE: 142

Ser Leu Leu Val Thr Val Ala Phe Ile Ile Phe Trp Val Ser Arg Gly
1               5                   10                  15

Arg Lys Lys Leu Leu Tyr Ile Phe Lys Gln
            20                  25

<210> SEQ ID NO 143
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17A

<400> SEQUENCE: 143

Ser Leu Leu Val Thr Val Ala Phe Ile Ile Phe Trp Val Lys Arg Gly
1               5                   10                  15

Ala Lys Lys Leu Leu Tyr Ile Phe Lys Gln
            20                  25

<210> SEQ ID NO 144
<211> LENGTH: 26
<212> TYPE: PRT
<213> ORGANISM: Artificial Sequence
<220> FEATURE:
<223> OTHER INFORMATION: Synthetic
```

```
<220> FEATURE:
<223> OTHER INFORMATION: junction region R17H

<400> SEQUENCE: 144

Ser Leu Leu Val Thr Val Ala Phe Ile Ile Phe Trp Val Lys Arg Gly
1               5                   10                  15

His Lys Lys Leu Leu Tyr Ile Phe Lys Gln
            20                  25

<210> SEQ ID NO 145
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17L

<400> SEQUENCE: 145

Ser Leu Leu Val Thr Val Ala Phe Ile Ile Phe Trp Val Lys Arg Gly
1               5                   10                  15

Leu Lys Lys Leu Leu Tyr Ile Phe Lys Gln
            20                  25

<210> SEQ ID NO 146
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17N

<400> SEQUENCE: 146

Ser Leu Leu Val Thr Val Ala Phe Ile Ile Phe Trp Val Lys Arg Gly
1               5                   10                  15

Asn Lys Lys Leu Leu Tyr Ile Phe Lys Gln
            20                  25

<210> SEQ ID NO 147
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region L20A

<400> SEQUENCE: 147

Ser Leu Leu Val Thr Val Ala Phe Ile Ile Phe Trp Val Lys Arg Gly
1               5                   10                  15

Arg Lys Lys Ala Leu Tyr Ile Phe Lys Gln
            20                  25

<210> SEQ ID NO 148
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region L20S
```

```
<400> SEQUENCE: 148

Ser Leu Leu Val Thr Val Ala Phe Ile Ile Phe Trp Val Lys Arg Gly
1               5                   10                  15

Arg Lys Lys Ser Leu Tyr Ile Phe Lys Gln
            20                  25

<210> SEQ ID NO 149
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17A

<400> SEQUENCE: 149

Ser Leu Leu Val Thr Val Ala Phe Ile Ile Phe Trp Val Gln Arg Gly
1               5                   10                  15

Ala Lys Lys Leu Leu Tyr Ile Phe Lys Gln
            20                  25

<210> SEQ ID NO 150
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17N

<400> SEQUENCE: 150

Ser Leu Leu Val Thr Val Ala Phe Ile Ile Phe Trp Val Gln Arg Gly
1               5                   10                  15

Asn Lys Lys Leu Leu Tyr Ile Phe Lys Gln
            20                  25

<210> SEQ ID NO 151
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17S

<400> SEQUENCE: 151

Ser Leu Leu Val Thr Val Ala Phe Ile Ile Phe Trp Val Gln Arg Gly
1               5                   10                  15

Ser Lys Lys Leu Leu Tyr Ile Phe Lys Gln
            20                  25

<210> SEQ ID NO 152
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/L20A

<400> SEQUENCE: 152

Ser Leu Leu Val Thr Val Ala Phe Ile Ile Phe Trp Val Gln Arg Gly
1               5                   10                  15

Arg Lys Lys Ala Leu Tyr Ile Phe Lys Gln
            20                  25
```

-continued

```
<210> SEQ ID NO 153
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/L20S

<400> SEQUENCE: 153

Ser Leu Leu Val Thr Val Ala Phe Ile Ile Phe Trp Val Gln Arg Gly
1               5                   10                  15

Arg Lys Lys Ser Leu Tyr Ile Phe Lys Gln
            20                  25

<210> SEQ ID NO 154
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17N/L20A

<400> SEQUENCE: 154

Ser Leu Leu Val Thr Val Ala Phe Ile Ile Phe Trp Val Lys Arg Gly
1               5                   10                  15

Asn Lys Lys Ala Leu Tyr Ile Phe Lys Gln
            20                  25

<210> SEQ ID NO 155
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region R17N/L20S

<400> SEQUENCE: 155

Ser Leu Leu Val Thr Val Ala Phe Ile Ile Phe Trp Val Lys Arg Gly
1               5                   10                  15

Asn Lys Lys Ser Leu Tyr Ile Phe Lys Gln
            20                  25

<210> SEQ ID NO 156
<211> LENGTH: 26
<212> TYPE: PRT
<213> ORGANISM: Artificial Sequence
<220> FEATURE:
<223> OTHER INFORMATION: Synthetic
<220> FEATURE:
<223> OTHER INFORMATION: junction region K14Q/R17N/L20A

<400> SEQUENCE: 156

Ser Leu Leu Val Thr Val Ala Phe Ile Ile Phe Trp Val Gln Arg Gly
1               5                   10                  15

Asn Lys Lys Ala Leu Tyr Ile Phe Lys Gln
            20                  25

<210> SEQ ID NO 157
<211> LENGTH: 26
<212> TYPE: PRT
<213> ORGANISM: Artificial Sequence
<220> FEATURE:
<223> OTHER INFORMATION: Synthetic
```

```
<220> FEATURE:
<223> OTHER INFORMATION: junction region K14Q/R17N/L20S

<400> SEQUENCE: 157

Ser Leu Leu Val Thr Val Ala Phe Ile Ile Phe Trp Val Gln Arg Gly
1               5                   10                  15

Asn Lys Lys Ser Leu Tyr Ile Phe Lys Gln
            20                  25

<210> SEQ ID NO 158
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 158
gaatctaagt acggaccgcc ctgccccct tgccct                                  36

<210> SEQ ID NO 159
<211> LENGTH: 112
<212> TYPE: PRT
<213> ORGANISM: Artificial Sequence
<220> FEATURE:
<223> OTHER INFORMATION: Synthetic
<220> FEATURE:
<223> OTHER INFORMATION: CD3 Zeta

<400> SEQUENCE: 159

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```